(12) United States Patent
Castro et al.

(10) Patent No.: US 8,778,619 B2
(45) Date of Patent: Jul. 15, 2014

(54) OXIDIZED CARDIOLIPIN AND USES TO DETECT CARDIOLIPIN ANTIBODIES

(71) Applicants: The United States of America as Represented by the Secretary of the Department of Health and Human Services, Centers for Disease Control and Prevention, Washington, DC (US); Arlington Scientific, Inc., Springville, UT (US)

(72) Inventors: Arnold R. Castro, Monroe, GA (US); Himanshu Champaklal Mody, Springville, UT (US)

(73) Assignees: The United States of America as represented by the Secretary of the Department of Health and Human Services, Washington, DC (US); Arlington Scientific Inc., Springville, UT (US)

( * ) Notice: Subject to any disclaimer, the term of this patent is extended or adjusted under 35 U.S.C. 154(b) by 0 days.

(21) Appl. No.: 14/079,634

(22) Filed: Nov. 13, 2013

(65) Prior Publication Data
US 2014/0087398 A1    Mar. 27, 2014

Related U.S. Application Data

(63) Continuation-in-part of application No. 13/027,224, filed on Feb. 14, 2011, which is a continuation of application No. 12/094,144, filed as application No. PCT/US2006/044572 on Nov. 17, 2006, now Pat. No. 7,888,043.

(60) Provisional application No. 60/737,901, filed on Nov. 18, 2005.

(51) Int. Cl.
*G01N 33/53* (2006.01)
*G01N 33/554* (2006.01)
*G01N 33/567* (2006.01)

(52) U.S. Cl.
USPC ............................. 435/7.1; 435/7.2; 435/7.32

(58) Field of Classification Search
None
See application file for complete search history.

(56) References Cited

U.S. PATENT DOCUMENTS

| | | |
|---|---|---|
| 3,564,089 A | 2/1971 | Kiddy |
| 4,081,334 A | 3/1978 | Suzuki et al. |
| 4,738,932 A | 4/1988 | Yabusaki |
| 4,740,467 A | 4/1988 | Kettman et al. |
| 4,894,328 A | 1/1990 | Alderete et al. |
| 5,780,319 A | 7/1998 | Wilson et al. |
| 5,798,273 A | 8/1998 | Shuler et al. |
| 5,840,587 A | 11/1998 | Stewart et al. |
| 5,900,359 A | 5/1999 | Matsuura et al. |
| 6,214,629 B1 | 4/2001 | Freitag et al. |
| 6,258,548 B1 | 7/2001 | Buck |
| 6,261,792 B1 | 7/2001 | Janoff et al. |
| 6,372,516 B1 | 4/2002 | Sun |
| 6,815,173 B1 | 11/2004 | Pope et al. |
| 7,691,581 B2 | 4/2010 | Kintrup et al. |
| 2009/0263825 A1 | 10/2009 | Castro |
| 2010/6221740 | 9/2010 | Castro et al. |
| 2011/0136143 A1 | 6/2011 | Castro et al. |

FOREIGN PATENT DOCUMENTS

| | | |
|---|---|---|
| JP | Hei 4-503865 | 7/1992 |
| JP | 11-258236 | 9/1999 |
| JP | 2001-228156 | 8/2001 |
| JP | 2003-344413 | 12/2003 |
| WO | WO 90/10227 A | 9/1990 |
| WO | WO 91/10138 A1 | 7/1991 |
| WO | WO 99/08113 A | 2/1999 |
| WO | WO 00/75666 | 12/2000 |
| WO | WO 02/066990 A2 | 8/2002 |
| WO | WO 2004/040311 A1 | 5/2004 |
| WO | WO 2007/002178 A2 | 1/2007 |

OTHER PUBLICATIONS

Borovyagin et al., "Model Membrane Morphology and Crosslinking of Oxidized Lipids with Proteins," *J. Ultrastruct. Res.* 89:261-273, 1984.
Castro et al., "Use of synthetic cardiolipin and lecithin in the antigen used by the venereal disease research laboratory test for serodiagnosis of syphilis," *American Society for Microbiology*, 7(4):658-661 (2000).
Costello et al., "The Structural Requirements for Anti-Cardiolipin Antibody Binding in Sera from Patients with Syphilis and SLE," *Clin. Immunol. Immunopathol.* 56:393-400, 1990.
Egglestone et al., "Serological diagnosis of syphilis," *Communicable Disease and Public Health*, 3(3):158-162 (2000).
Horkko et al., "Antiphospholipid antibodies are directed against epitopes of oxidized phospholipids," *The Journal of Clinical Investigation*, 93(3):815-825 (1996).
Larsen et al., "Laboratory Diagnosis and Interpretation of Test for Syphilis," *Clinical Microbiology Reviews*, 8(1):1-21 (1995).
Pope et al., "Comparison of the Serodia *Treponema pallidum* Particle Agglutination, Captia Syphilis-G, and SpiroTek Reagin II Tests with Standard Test Techniques for Diagnosis of Syphilis," *Journal of Clinical Microbiology*, 38(7):2543-2545 (2000).
Practico et al., "Circulating autoantibodies to oxidized cardiolipin correlate with isoprostane F(2alpha)-VI levels and the extent of atherosclerosis in ApoE-deficient mice: modulation by vitamin E." *Blood*, 97(2):459-464 (2001).
Shlame et al., Effect of Cardiolipin Oxidation on Solid-Phase Immunoassay for Antiphospholipid Antibodies, *Thromb Haemost*,86:1475-82 (2001).
World Health Organization, Serological Diagnosis of Syphilis, Technical Report Series 674, 1982, Geneva, CH.

*Primary Examiner* — Albert Navarro
(74) *Attorney, Agent, or Firm* — Klarquist Sparkman, LLP

(57) ABSTRACT

Compositions, methods and devices for the detection of anti-lipoidal antibodies and the diagnosis of disease, for example, syphilis, are described. In particular, oxidized cardiolipins, which may be conjugated with a variety of attachment molecules, such as BSA, KLH, biotin, synthetic protein MAPS, IgY, streptavidin, or avidin, are described. Such oxidized cardiolipin, alone or complexed with one or more attachment molecules, are useful to detect anti-lipoidal antibodies (such as IgG and IgM antibodies) in subjects, for example, when used in ELISA plates. ELISA plates are described that permit the detection of anti-lipoidal antibodies and that permit the co-detection of nontreponemal and treponemal antibodies in biological samples.

12 Claims, 13 Drawing Sheets

| | Lane No. | | | | | |
|---|---|---|---|---|---|---|
| Preparation | 1 | 2 | 3 | 4 | 5 | 6 |
| 1:1 BSA | 12 µg | 6 µg | 3 µg | 1.5 µg | 750 ng | 375 ng |
| 1:1 KLH | 21 µg | 10.5 µg | 5.2 µg | 2.6 µg | 1.3 µg | 656 ng |
| 1:3 BSA | 10.5 µg | 5.25 µg | 2.6 µg | 1.3 µg | 656 ng | 328 ng |
| 1:3 KLH | 3 µg | 1.5 µg | 750 ng | 375 ng | 187 ng | 93 ng |
| 1:5 BSA | 9.9 µg | 4.9 µg | 2.47 µg | 1.23 µg | 618 ng | 309 ng |
| 1:5 KLH | 3 µg | 1.5 µg | 750 ng | 375 ng | 187 ng | 93 ng |
| BSA Control | 15 µg | 7.5 µg | 3.7 µg | 1.87 µg | 937 ng | 468 ng |
| Blank | 0 | 0 | 0 | 0 | 0 | 0 |

OXIDIZED CARDIOLIPIN AND USES TO DETECT CARDIOLIPIN ANTIBODIES

CROSS REFERENCE TO RELATED APPLICATIONS

This is a continuation-in-part application of U.S. application Ser. No. 13/027,224 filed Feb. 15, 2011, pending, which is a continuation of U.S. application Ser. No. 12/094,144 filed May 16, 2008, now U.S. Pat. No. 7,888,043, which was the U.S. National Stage of International Application No. PCT/US2006/044572, filed Nov. 17, 2006, which was published in English under PCT Article 21(2), which in turn application claims the benefit of U.S. Provisional Application No. 60/737,901, filed Nov. 18, 2005, which is incorporated herein by reference in its entirety.

ACKNOWLEDGMENT OF GOVERNMENT SUPPORT

This invention was made by the National Center for HIV, STD, and TB Prevention, Division of AIDS, STD, and TB Laboratory Research, Laboratory Reference and Research Branch, Centers for Disease Control and Prevention, an agency of the United States Government.

JOINT RESEARCH AGREEMENT

There is a joint research agreement in place between the Centers for Disease Control and Prevention and Arlington Scientific, Inc.

FIELD

This disclosure relates to oxidized cardiolipin compositions and uses therefor; in particular, to methods of immobilizing oxidized cardiolipin to a solid support, and related immunoassays (such as ELISA), which assays and devices are useful, for example, for detection of anti-lipoidal IgG and IgM antibodies and/or diagnosis of disease (such as syphilis).

BACKGROUND

Syphilis is a sexually transmitted disease (STD) caused by the spirochete bacterium *Treponema pallidum*. Over 100,000 cases of adult syphilis are reported worldwide each year. In addition, the disease is transmitted congenitally and affects 3000 or more infants annually. The course of syphilis infection spans many years and may lead to a variety of clinical presentations, which are characterized by four stages.

The primary stage of syphilis infection occurs 10-100 days after bacterial infection, and is characterized by the appearance of one or more chancres (red, bloodless, painless ulcers typically less than 1 cm in diameter). The chancres may appear on the genitalia or elsewhere on the body. A chancre lasts 3-6 weeks and heals without treatment, leaving a small scar. Infected persons are contagious during this stage.

The secondary stage of syphilis infection is characterized by rash-like skin lesions that can cover part or all of the body. The skin lesions are generally painless and appear 1-6 months after the onset of the initial chancre(s). The skin lesions can resemble warts, pustules, or ulcers. Left untreated, they heal in 2-12 weeks without scarring. Fever, sore throat, weakness, weight loss, swelling of the lymph nodes, and loss of the eyelashes and/or part of the eyebrows can also occur during this stage of infection. In addition, the symptoms may progress to meningovascular syphilis, which is characterized by inflammation of the covering of the brain and spinal cord and/or changes in the vasculature of the brain. Infected persons are also contagious in the secondary phase.

The next stage of this disease is latent syphilis or the hidden stage. During this stage, the infected person appears to have recovered and is asymptomatic. This stage lasts for life in approximately two thirds of persons who are not treated for syphilis. During the first year of latency, relapses of secondary stage symptoms may occur. Except during a relapse, infected persons are not contagious during this latent stage; however, children born to latently infected mothers within four years of the appearance of the primary chancre may contract congenital syphilis.

Tertiary or late syphilis is the final stage of untreated infection. This stage may occur as early as one year after infection or anytime thereafter with 10 to 20 years being most common. Benign syphilis, characterized by lesions called gummas, can occur in the bone, skin, and internal organs. Death is rare, but severe disfigurement and pain can occur. Cardiovascular syphilis is characterized by aortic aneurysms as well as other cardiovascular problems and frequently results in death. Neurologic involvement may occur in the early stages of syphilis as well as manifest as late stage symptoms. In the late stage disease, neurosyphilis may be asymptomatic or the patient may have severe neurologic problems such as possible dementia, insanity, impairment of mobility, blindness, deafness, or even death.

The immune response in syphilis involves production of (i) treponemal antibodies, which are specific for *T. pallidum* antigens, and (ii) anti-lipoidal antibodies, which recognize lipoidal material released from damaged host cells, lipoprotein-like material and possibly cardiolipin released from the treponemes. The mainstay of syphilis screening and diagnosis is serological testing for either or both of these two types of antibodies. The nontreponemal or heterophile antibodies (reagin) directed against cardiolipin are released from damaged host cells and from the treponemes themselves. These antibodies can also be present in other diseases and human conditions such as lupus, malaria, HIV, IV drug users, etc. The presence of nontreponemal antibodies is indicative of active infection; thus a reduction in titer can suggest a successful antibiotic therapy, and a significant increase can indicate a possible relapse or reinfection. The treponemal antibodies are primarily directed against specific lipoprotein antigens of the bacterium. Even after treatment or time, these antibodies usually remain present for life. Thus, a positive treponemal test cannot distinguish between active, treated, and old case of syphilis.

Tests for anti-lipoidal antibodies (often called "non-treponemal tests") are typically based on an antigen composed of naturally occurring cardiolipin, cholesterol and lecithin. The widely used non-treponemal tests (e.g., Venereal Disease Research Laboratory (VDRL) test and Rapid Plasma Reagin (RPR) test) monitor, either microscopically (e.g., VDRL test) or macroscopically (e.g., RPR test), the formation of a flocculent comprised of antigen-antibody complexes. Non-treponemal tests have the advantage of being widely available, inexpensive and convenient to perform on large numbers of specimens. Moreover, because anti-lipoidal antibody titers decrease with successful treatment for syphilis, eventually disappearing in most patients, while treponemal antibodies titers remain high for years or even a lifetime, non-treponemal tests are considered the better choice for monitoring treatment or testing for reinfection.

Treponemal tests are based on antigens derived from *T. pallidum* and include the *T. pallidum* particle agglutination (TP-PA), the fluorescent treponemal antibody-absorbed test (FTA-ABS) and enzyme immunoassays. Treponemal tests are used primarily to verify reactivity in non-treponemal tests. The treponemal test may also be used to confirm a clinical impression of syphilis in which the non-treponemal test is nonreactive. Treponemal tests are technically more difficult, time consuming, and expensive to perform and cannot be used to monitor treatment because the test will remain reactive for years or a lifetime in approximately 85% of persons successfully treated for syphilis.

Each of the above-described antibody tests is performed using a serum sample that is obtained in a clinical setting and sent to a laboratory for analysis. Therefore, test results are typically not available for several days after the sample is collected. Because of the frequent difficulty of tracing patients with STDs, the development of a rapid, point-of-care test is needed to aid the clinician in making a judgment, preferably on the day of testing.

Immunoassay devices, which offer rapid, on-site results, are available to qualitatively test serum levels of treponemal antibodies (e.g., DiaSys Corporation; ACON Laboratories, Inc.; Biokit, S. A.; Genix Technology; Standard Diagnostics; Cortez Diagnostics, Inc.; and Phoenix Bio-Tech Corp). However, analogous tests for anti-lipoidal antibodies have been more difficult to develop at least in part because the hydrophobic antigens of the anti-lipoidal antibodies (e.g., cardiolipin) resist attachment to solid supports, which is one element of an immunoassay device. In addition, methods that permit quantitative detection of non-treponemal IgG and IgM antibodies using enzyme immunoassays (EIAs) are not commercially available.

According to some experts, syphilis detection would be further aided by a combination of a non-treponemal test and a treponemal test for screening and diagnostic purposes. This is an approach advocated by the World Health Organization, Treponemal Infections, Technical Report Series 674, Geneva: WHO, 1982. An easy-to-use, rapid, point-of-care test capable of concurrently detecting both non-treponemal and treponemal antibodies would help address this long-felt need.

SUMMARY

The present disclosure provides an assay for the detection of non-treponemal antibodies (NTA), or both NTA and TA. In some examples, such a method can be used instead of the currently available conventional test (RPR or VDRL) for the detection of NTA. In some examples, the disclosed methods are automated, free from interpretational error and permit efficacy of treatment to be monitored.

Efforts to develop non-solution immunoassays for non-treponemal testing (or combined non-treponemal and treponemal testing) have been frustrated by the difficulty of attaching antigens specifically recognized by anti-lipoidal antibodies, such as cardiolipin, to a solid substrate, such as an ELISA plate. The very small size of the cardiolipin molecule has resulted in poor localization of the molecule on the substrate. The nonpolar nature of the fatty acid side chains of cardiolipin also imparts a high degree of hydrophobicity to the molecule that makes it difficult to bind cardiolipin to polar surfaces, such as nitrocellulose, latex beads, or the plastic of immunoassay plates. Although the size of the molecule could be increased by conjugating the cardiolipin to larger molecules (such as proteins), such conjugations have resulted in the loss of antigenicity of the cardiolipin.

A method that permits attachment of cardiolipin (or lipoidal antigens comprising cardiolipin modified as described herein, phosphatidylcholine (also referred to as "lecithin"), and cholesterol) to a solid substrate (such as a multi-well plate) while maintaining the antigenicity and specificity of the antigen for anti-lipoidal antibodies was previously described (see e.g., U.S. Pat. No. 7,888,043). Using methods described herein, it is possible to create cardiolipin-attachment molecule complexes, which can be attached to a variety of solid supports. Oxidized and activated cardiolipin can be conjugated to macromolecules (e.g., BSA, KLH, chicken IgY antibody, or avidin), thus permitting attachment to a solid substrate. In other examples, oxidized and activated cardiolipin can be attached to a solid substrate containing amine groups. The ability to attach the immunogenic cardiolipin complex in this manner allows it to be used in non-solution-based immunoassays, such as ELISAs and immunoassay devices for testing of non-treponemal antibodies. In certain embodiments, disclosed immunoassay devices also incorporate treponemal antigens that are recognized by *T. pallidum*, such that the device conveniently concurrently detects both non-treponemal and treponemal antibodies.

In one particular example, fatty acid side-chains of cardiolipin are oxidized to provide at least one terminal carboxyl group, which is then cross-linked to a polypeptide (such as BSA) that is readily attachable (or already attached) to a solid support (such as the permeable substrate of a multi-well plate).

Thus, the disclosure provides method of making oxidized cardiolipin and solid supports, such as a multi-well plate, that include the oxidized cardiolipin that is immunoreactive with anti-lipoidal antibodies, wherein the oxidized cardiolipin includes a central glycerol moiety and fatty acid side chains. In one example, the oxidized cardiolipin is generated by a method that includes reacting the cardiolipin with a periodate salt and a permanganate salt to oxidize fatty acid side chains of the cardiolipin to provide terminal carboxyl groups on one or more of the side chains, adding a reducing agent to the cardiolipin suspension after reacting the cardiolipin with the periodate salt and the permanganate salt to quench oxidation of the cardiolipin and to reduce a β-ketone formed in the central glycerol moiety to a β-hydroxyl group so as to retain immunogenicity of the central glycerol moiety, and activating the carboxyl groups of the oxidized cardiolipin to covalently attach a protein carrier (e.g., BSA, KLH, avidin, or IgY) to at least one of the carboxyl groups or to permit attachment of the oxidized cardiolipin to an amine. In some examples, such a solid support also includes a treponemal antigen that reacts with antibodies to *T. pallidum*, thus permitting detection of TAs and NTAs in a sample.

Methods of using the solid supports, such as an enzyme-linked immunosorbent assay (ELISA) multi-well plate, are also provided. In some examples, such methods permit diagnosis of syphilis, determine the stage of syphilis infection (such as monitoring the progression of the disease), permit monitoring of syphilis therapy, or combinations thereof. In some examples, the methods permit detection of NTA IgM and IgG antibody content in a sample (such as a qualitative or quantitative measurement). In some examples the methods include contacting or adding a biological sample from a subject with or to the disclosed solid supports and then detecting formation of a complex among an anti-lipoidal antibody (e.g., IgG, IgA, and/or IgM) in the biological sample and the oxidized cardiolipin on the solid support. Detection of the complex can diagnose syphilis, determine an amount of IgG, IgA, and/or IgM present, determine the stage of syphilis infection, determine whether a treatment is working in a patient, or combinations thereof. In some examples, the method also includes contacting with or adding to the solid support a labeled anti-human antibody, such as a labeled goat-anti human IgG, labeled goat-anti human IgM, or both. In some examples, the method also includes contacting with or adding to the solid support a labeled cardiolipin molecule (such as a biotin-labeled cardiolipin, which can be detected using labeled streptavidin), which can bind to the anti-lipoidal antibody/oxidized complex on the solid support (if present).

In some examples, the method further includes detecting treponemal antigens (TAs) in the sample (or determining if TAs are present in the sample). Any method to detect TA can be used, such as an EIA, *Treponema pallidum* particle agglutination assay (TPPA), or the Rapid Test assay. In some example, TAs are detected in the same multiwell plate as NTAs are detected, and in some examples in the same well (wherein detection of NTAs and TA occurs using different detectable labels.

The foregoing and other features will become more apparent from the following detailed description of several embodiments, which proceeds with reference to the accompanying drawings.

DETAILED DESCRIPTION

I. Introduction

Figure 3:
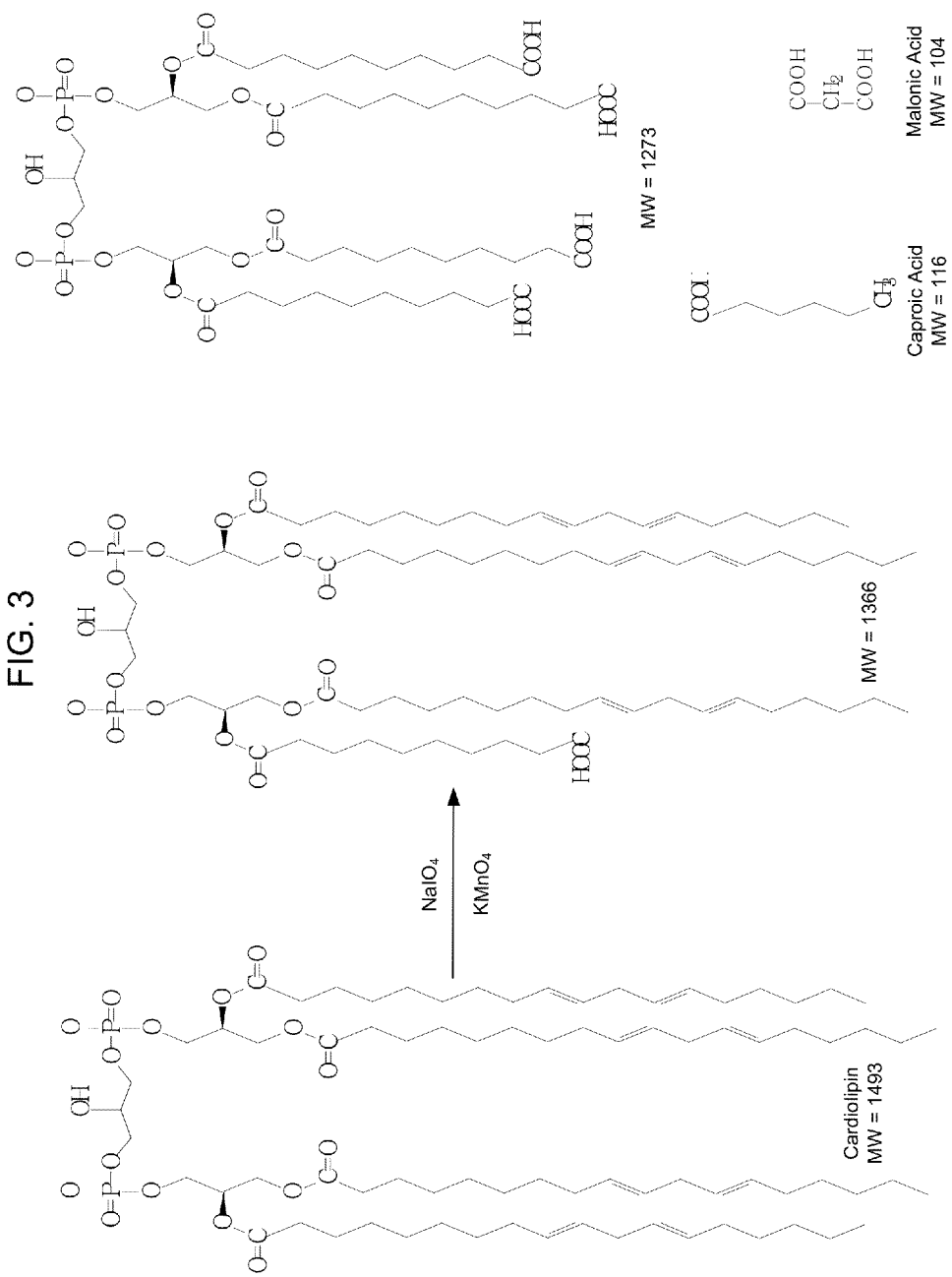
FIG. 3 shows a schematic oxidation reaction of an exemplary cardiolipin molecule that contains four 18-carbon, di-unsaturated fatty acid chains. The illustrated cardiolipin reaction products have either one or four oxidized fatty acid side chains. In practice, the oxidation reaction products would also include oxidized cardiolipin species where any two or three of the fatty acid chains were oxidized to carboxyl groups.

As shown in FIG. 3, cardiolipin includes a central immunogenic glycerol moiety with fatty acid side chains. This specification discloses methods for preparing oxidized cardiolipin that is capable of being attached to a substrate (for example via an amine group or via a protein carrier), while retaining the ability of the central glycerol moiety to be immunoreactive with anti-lipoidal antibodies. Also provided are solid substrates, such as a multi-well plate, which includes the oxidized cardiolipin attached thereto. In some examples, cardiolipin is reacted with a periodate salt (such as sodium m-periodate) and a permanganate salt (such as potassium permanganate) to oxidize at least one of the fatty acid side chains of the cardiolipin to provide terminal carboxyl groups on one or more of the side chains, then a reducing agent (such as a bisulfite salt) is added to quench oxidation of the cardiolipin and to reduce a β-ketone formed in the central glycerol moiety to a β-hydroxyl group so as to retain immunogenicity of the central glycerol moiety. The carboxyl groups of the oxidized cardiolipin are activated to covalently attach a protein carrier to at least one of the carboxyl groups or to permit attachment of the oxidized cardiolipin to an amine (such as a protein carrier or an amine present in one or more wells of a multi-well plate). Activating the carboxyl groups is achieved in particular examples by reacting the oxidized cardiolipin with a carbodiimide, such as 1-ethyl-3-(3-dimethylamino propyl)carbodiimide (EDC) and a succinimide such as N-hydroxysuccinimide (NHS). A protein carrier (such as, bovine serum albumin (BSA), keyhole limpet hemocyanin (KLH), IgY, or avidin), or biotin, is then covalently attached to at least one of the activated carboxyl groups.

The cardiolipin can be reacted with the periodate salt before the cardiolipin is reacted with the permanganate salt. In particular embodiments, the oxidation reaction with the cardiolipin occurs in an alcohol solvent, under an argon atmosphere. Examples of suitable alcohol solvents are one or more of t-butanol, ethanol, propanol, or methanol. The molar ratio of sodium m-periodate to cardiolipin is about 4:1 to about 5:1, and the molar ratio of potassium permanganate to cardiolipin is about 0.5:1 to about 1:1. In some examples, the bisulfite salt is sodium bisulfite.

Also disclosed herein are methods for preparing oxidized cardiolipin that is immunoreactive with anti-lipoidal antibodies, and capable of linking to a polypeptide for attachment to a substrate. Such methods include reacting the cardiolipin with sodium m-periodate and potassium permanganate in a t-butanol solvent under an argon atmosphere to oxidize the cardiolipin and provide terminal carboxyl groups on one or more of the side chains. Sodium bisulfite in aqueous solution is then added to the cardiolipin suspension to quench oxidation of the cardiolipin and to reduce a β-ketone formed in the central glycerol moeity to a β-hydroxyl group so as to retain immunogenicity of the central glycerol moiety. The terminal carboxyl groups of the oxidized cardiolipin are then activated by reacting the oxidized cardiolipin with EDC and then NHS, followed by covalently conjugating a protein carrier to at least one of the carboxyl groups.

The oxidized cardiolipins can then be attached to a substrate. For example, the terminal carboxyl groups can be used to attach the cardiolipin to polypeptide carriers or amino groups present on a solid substrate, such as in the wells of a multi-well plate (such as an ELISA plate), or to a lateral flow substrate (such as a nitrocellulose strip). The ability to provide the oxidized cardiolipin permits the cardiolipin to be reliably attached to a solid substrate. Such solid substrates can also include a treponemal antigen that reacts with antibodies to *T. pallidum*. The presence of both a cardiolipin-polypeptide conjugate and a treponemal antigen on (or in) the same solid support conveniently allows rapid clinical testing for both anti-lipoidal and anti-treponemal antibodies in the same biological specimen.

Also disclosed herein are immunoassay devices (such as multi-well plates, lateral flow or flow-through devices) for determining the presence and/or amount of an anti-lipoidal antibody in a fluid sample. In one example, the multi-well plate, such as an ELISA plate, includes attached to the wells thereof amino groups or carrier proteins, to which the oxidized cardiolipin can be attached using routine methods.

In one example a lateral flow device typically include a sample application area and a separate cardiolipin capture area in which an immobilized cardiolipin-polypeptide conjugate is provided which conjugate has a specific binding affinity for a mobile-phase anti-lipoidal antibody. Any liquid (such as a fluid biological sample) applied in the sample application area flows along a path of flow from the sample application area to the cardiolipin capture area. The path of flow may continue to a downstream absorbent pad associated with the immunoassay device, which acts, at least in part, as a liquid reservoir. Formation of a complex between the anti-lipoidal antibody and the immobilized oxidized cardiolipin can be detected to determine the presence and/or amount of the anti-lipoidal antibody in a fluid sample. In some embodiments of a lateral flow device, a conjugate pad is placed in the path of flow from the sample application area to the cardiolipin capture area. The conjugate pad includes a mobile or mobilizable detector reagent for an anti-lipoidal antibody, such that flow of liquid through the pad moves the detector reagent to the cardiolipin capture area. Formation of a complex including the detector reagent, anti-lipoidal antibody (analyte), and immobilized cardiolipin provides a visible or otherwise detectable indicator of the presence of the anti-lipoidal antibody in a biological specimen. In alternative embodiments (including lateral flow or flow-through devices), the detector reagent is not supplied in a conjugate pad, but is instead applied to the substrate or sample, for example from a developer bottle.

Examples of detector reagents include labeled oxidized cardiolipin or labeled anti-human antibody, in which the label is one or more of an enzyme, colloidal gold particle, colored latex particle, protein-adsorbed silver particle, protein-adsorbed iron particle, protein-adsorbed copper particle, protein-adsorbed selenium particle, protein-adsorbed sulfur particle, protein-adsorbed tellurium particle, protein-adsorbed carbon particle, or protein-coupled dye sac.

Certain immunoassay device embodiments (such as multi-well plates, lateral flow or flow-through devices) also include a treponemal capture area (e.g., in particular wells of the multi-well plate or in the flow path from the sample application area). Such treponemal capture area may include, for example, an immobilized treponemal antigen having a specific binding affinity for an anti-*T. pallidum* antibody or an immobilized anti-*T. pallidum* antibody having a specific binding affinity for a *T. pallidum* organism or *T. pallidum* antigen. The captured *T. pallidum* antibody, organism or antigen can be detected by a detector reagent specific for the treponemal antibody, organism, or antigen. Thus, a lateral flow device may also have a mobile or mobilizable detector reagent specific for the treponemal antibody or antigen in the conjugate pad. A detector reagent for the treponemal antibody or antigen may be in the same or a different pad than the detector reagent for the anti-lipoidal antibody. In particular embodiments, a detector reagent specific for an anti-*T. pallidum* antibody includes labeled (e.g., gold-conjugated) Protein A, labeled (e.g., gold-conjugated) Protein G, or labeled (e.g., gold-conjugated) anti-human antibody. In other embodiments, detector reagent for a treponemal antigen can be a labeled (e.g., gold-conjugated) anti-treponemal antigen antibody.

The disclosed immunoassay devices can be used in methods for diagnosing syphilis in a subject by analyzing a biological sample from the subject, by applying the biological sample to the device (e.g., contacting the sample with the device, for example by introducing the sample into wells of a multi-well plate) and detecting formation of a complex between the anti-lipoidal antibody (e.g., IgG, IgA, and/or IgM) in the sample and the oxidized cardiolipin attached to the solid support. In some examples the complex further includes a detector reagent (e.g., a labeled anti-human antibody, such as a labeled goat-anti human IgG, a labeled goat-anti human IgM, or both). For example, the multi-well plate can be contacted with a mixture containing both a labeled goat-anti human IgG and a labeled goat-anti human IgM, or can be contacted separately with a labeled goat-anti human IgG or a labeled goat-anti human IgM (e.g., a first multi-well plate or particular wells of the plate can be contacted with labeled goat-anti human IgG and a second multi-well plate or particular wells of the plate can be contacted with labeled goat-anti human IgM). In some examples, the e label is horseradish peroxidase (HRP) and the method further includes contacting the solid support (e.g., multi-well plate) with tetramethyl benzidine (TMB) and wherein detecting comprises detecting a signal spectrophotometrically at 450 nm. Detection of the formation of the complex detects an anti-lipoidal antibody associated with infection with syphilis. In those embodiments in which the device includes a conjugate pad in the path of flow from the sample application area to the cardiolipin capture area, the detected complex includes the mobile or mobilizable detector reagent. In other embodiments in which the detector reagent is applied to the device from an external source, the detected complex includes the externally applied detector.

In one embodiment of the method, the solid support (e.g., multi-well plate or lateral flow device) is capable of detecting both the anti-lipoidal antibodies (that are an indicator of active infection) and anti-treponemal antibodies (that verify reactivity of the non-treponemal test). In those embodiments of the device which include the treponemal antigen, the method includes detecting formation of a complex between the anti-$T.$ $pallidum$ antibody, the immobilized treponemal antigen (for example immobilized in the same or a different well as the oxidized cardiolipin), and a detector reagent. As with the detector reagent used for the cardiolipin, the detector reagent for the treponemal antigen can be applied from an external source.

Also disclosed herein are kits for the diagnosis of syphilis. These kits include a disclosed immunoassay device and instructions for applying the biological sample to the sample application area or the multi-well plate. The kit may also include instructions for interpreting results of the test. In some examples the kits include controls (such as a negative and positive control), labeled anti-human antibody, such as a labeled goat-anti human IgG, a labeled goat-anti human IgM, or both. In some examples the label is HRP. The kit can include detection reagents (such as TMB) stopping reagents, (such as 2 N sulfuric acid solution), wash solutions, diluents, or combinations thereof. In some examples the kit includes a calibration curve for non-treponemal IgG and/or IgM.

The disclosed immunoassay devices can be also used in methods for diagnosing other disorders, such as an anti-cardiolipin autoimmune disease, such as lupus, in a subject by analyzing a biological sample from the subject, by applying the biological sample to the device and detecting formation of a complex among the anti-lipoidal antibody, the oxidized cardiolipin, and a detector reagent in the capture area. Detection of the formation of the complex in the capture area detects an anti-lipoidal antibody associated with lupus. In some instances, one or more co-factors (such as $\beta_2$-glycoprotein I) are present (such as added to a sample) for the detection of lupus.

II. Abbreviations and Terms

BSA Bovine serum albumin
EDC 1-ethyl-3-(3-dimethylamino propyl)carbodiimide
EIA Enzyme Immuno-Assay
ELISA Enzyme-Linked Immunosorbent Assay
HPLC High pressure liquid chromatograph
KLH Keyhole limpet hemocyanin
LFD Lateral flow device
MES N-morpholinoethane sulfonic acid
NHS N-hydroxysulfosuccinimide
NMR Nuclear magnetic resonance
NTA: Non-treponemal antigen
PEG Polyethylene glycol
PVA Polyvinyl alcohol
PVP Polyvinyl pyrrolidone
SDS Sodium dodecyl sulfate
TA: Treponemal antigen
TLC Thin layer chromatography Unless otherwise noted, technical terms are used according to conventional usage. Definitions of common terms in molecular biology may be found in Benjamin Lewin, $Genes$ $V$, published by Oxford University Press, 1994 (ISBN 0-19-854287-9); Kendrew et al. (eds.), $The$ $Encyclopedia$ $of$ $Molecular$ $Biology$, published by Blackwell Science Ltd., 1994 (ISBN 0-632-02182-9); and Robert A. Meyers (ed.), $Molecular$ $Biology$ $and$ $Biotechnology:$ $a$ $Comprehensive$ $Desk$ $Reference$, published by VCH Publishers, Inc., 1995 (ISBN 1-56081-569-8).

In order to facilitate review of the various embodiments of the disclosure, the following explanations of specific terms are provided:

Activating Carboxyl Groups:

Activation of a carboxyl group refers to the reaction of a carboxyl group with an agent (or agents), such as a carbodiimide (e.g., 1-ethyl-3-(3-dimethylamino propyl)carbodiimide), to form a nucleophile-reactive derivative, such as an O-urea derivative. The nucleophile-reactive derivative is readily reactive with nucleophiles, and can be used to form (i) ether links with alcohol groups, (ii) ester links with acid and alcohols or phenols, and (iii) peptide bonds with acid and amines.

A catalytic auxiliary nucleophile, such as 1-hydroxybenzotriazole, N-hydroxysuccinimide, N-hydroxysulfosuccinimide, and N-hydroxy-5-norbene-endo-2,3-dicarboxamide may be used to assist carbodiimide-mediated activation of carboxyl groups to reduce possible side reactions, including racemisation, and to increase reaction rate when using active esters.

For example, a terminal carboxyl group of one or more fatty acid side chains of oxidized cardiolipin may be activated by reaction with 1-ethyl-3-(3-dimethylamino propyl)carbodiimide followed, in some instances, by reaction with a catalytic auxiliary nucleophile, such as N-hydroxysuccinimide.

Analyte:

An atom, molecule, group of molecules or compound of natural or synthetic origin (e.g., drug, hormone, enzyme, growth factor antigen, antibody, hapten, lectin, apoprotein, cofactor) sought to be detected or measured that is capable of binding specifically to cardiolipin embodiments described herein. Analytes may include, but are not limited to antibodies, drugs, hormones, antigens, haptens, lectins, apoproteins, or cofactors. In some embodiments, the analyte includes antibodies, such as anti-lipoidal or anti-cardiolipin antibodies, produced in response to infection by $T.$ $pallidum$. In other embodiments, the analyte includes anti-lipoidal antibodies produced in response to any of (i) an autoimmune disease, such as lupus, (ii) various venous and arterial thrombotic disorders, including cerebral infarction, (iii) deep venous thrombosis, (iv) thrombocytopenia, (v) pulmonary embolism, or (vi) recurrent fetal loss with placental infarction.

Antibody:

A protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies are naturally produced in plants and animals in response to antigens presented to the immune system. Naturally produced antibodies may be found, for example, in the serum of an animal. For example, a person infected with *T. pallidum* will produce antibodies at least against *T. pallidum* antigens and antibodies (anti-lipoidal antibodies) against lipoidal material that results from the treponemal infection, for example, from host cells damaged by the infection.

Antibodies may exist as intact immunoglobulins or as a number of well-characterized fragments produced by digestion with various peptidases or by recombinant DNA methods. For example, pepsin digests an antibody below the disulfide linkages in the hinge region to produce F(ab)'2, a dimer of Fab which itself is a light chain joined to $V_H$-$C_H$ 1 by a disulfide bond. The F(ab)'2 may be reduced under mild conditions to break the disulfide linkage in the hinge region thereby converting the F(ab)'2 dimer into an Fab' monomer. The Fab' monomer is essentially an Fab with part of the hinge region (see *Fundamental Immunology*, W. E. Paul, ed., Raven Press, N.Y., 1993). While certain antibody fragments are defined in terms of the digestion of an intact antibody, it will be appreciated that Fab' fragments or other antibody fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Anti-lipoidal antibodies for use in some embodiments of the methods and devices disclosed herein can be of any derivation, but most often will be found in the serum of a subject.

Antibodies may be monoclonal or polyclonal. Merely by way of example, monoclonal antibodies can be prepared from murine hybridomas according to the classical method of Kohler and Milstein (*Nature* 256:495-497, 1975) or derivative methods thereof. Briefly, a mouse is repetitively inoculated with a few micrograms of the selected analyte compound (or a fragment thereof) over a period of a few weeks. In some instances, it will be beneficial to use an adjuvant or a carrier molecule to increase the immunogenicity and/or stability of the analyte in the animal system. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

Antigen:

A chemical or biochemical compound, composition, structure, determinant, antigen or portion thereof that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Anti-Lipoidal Antibody:

An antibody (such as IgM or IgG) produced by the immune system of a subject (such as a human) in response to lipoidal antigens present in a disease state, such as an infection. For example, this term contemplates anti-lipoidal antibodies produced in response to lipoidal material released from host cells as a consequence of *T. pallidum* infection, and lipoprotein-like material and possibly cardiolipin released from treponemes. Anti-lipoidal antibodies may also be produced in response to nontreponemal diseases in which lipoidal antigens are also present, including, for example (i) an autoimmune disease, such as lupus (Harris et al., *Clin. Rheum. Dis.*, 11:591-609, 1985), (ii) various venous and arterial thrombotic disorders, including cerebral infarction (Harris et al., *Clin. Exp. Rheumatol.*, 2:47-51, 1984), (iii) deep venous thrombosis (Mueh et al., *Ann. Intern. Med.*, 92:156-159, 1980), (iv) thrombocytopenia (Harris et al., *Clin. Rheum. Dis.*, 11:591-609, 1985), (v) pulmonary embolism (Anderson and Ali, *Ann. Rheum. Dis.*, 43:760-763, 1984), or (vi) recurrent fetal loss with placental infarction (Derue et al., *J. Obstet. Gynaecol.*, 5:207-209, 1985).

Cardiolipin is one commonly known specific binding partner of anti-lipoidal antibodies that are formed in response to disease states, such as infection by *T. pallidum*. Naturally occurring cardiolipin has traditionally been used, often in combination with cholesterol and lecithin, in flocculation tests to detect anti-lipoidal antibodies, for example, in the serum of *T. pallidum*-infected patients.

Argon Atmosphere:

An atmosphere substantially comprising argon gas, which is created for the purposes of performing a chemical reaction. An argon atmosphere may be created in any closed vessel useful for performing chemical reactions by flushing the reaction vessel with argon gas to displace the atmosphere then-existing inside the vessel, and thereafter maintaining a flow of argon gas sufficient to maintain an atmosphere inside the reaction vessel substantially comprising argon gas. An atmosphere substantially comprises argon gas when the atmosphere is at least about 25% argon, at least about 30% argon, at least about 40% argon, at least about 50% argon, at least about 60% argon, at least about 70% argon, at least about 75% argon, at least about 80% argon, at least about 85% argon, at least about 90% argon, at least about 92% argon, at least about 95% argon, at least about 98% argon, or at least about 99% argon.

Attachment Molecule or Protein:

A peptide or other molecule (e.g., atom, molecule, group of molecules, protein, polymer, or compound of natural or synthetic origin) that can be directly or indirectly linked to cardiolipin as described herein to facilitate attachment of the cardiolipin to a solid support. In some embodiments, the attachment molecule-cardiolipin linkage is formed via carboxyl groups in oxidized cardiolipin, and/or optionally utilizes a linking group.

Suitable attachment molecules include, but are not limited to polypeptides, proteins, or peptides such as albumin, hemocyanin, thyroglobulin and derivatives thereof, particularly bovine serum albumin (BSA), synthetic protein MAPS, IgY, streptavidin, avidin, and keyhole limpet hemocyanin (KLH). Other polypeptide-derived or non-protein derived substances are known to those skilled in the art. An attachment molecule typically has a molecular weight of at least 50,000 daltons, preferably greater than 60,000 daltons. Attachment molecules often contain a reactive group to facilitate covalent conjugation to the oxidized cardiolipin. The amine groups of amino acids are often used in this manner. Attachment molecules lacking such groups can often be reacted with an appropriate chemical to produce them.

Binding Affinity:

A term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the disclosure that these constants be measured or determined. Rather, affinities as used herein to describe interactions between molecules of the described methods and devices are generally apparent affinities (unless otherwise specified) observed in empirical studies, which can be used to compare the relative strength with which one molecule (e.g., an antibody or other specific binding partner) will bind two other molecules (e.g., an analyte and an analyte-tracer conjugate). The concepts of binding affinity, association constant, and dissociation constant are well known.

Binding Domain:

The molecular structure associated with that portion of a receptor that binds ligand. The binding domain can refer to a polypeptide, natural or synthetic, or nucleic acid encoding such a polypeptide, the amino acid sequence of which represents a specific (binding domain) region of a protein, which either alone or in combination with other domains, exhibits binding characteristics that are the same or similar to those of a desired ligand/receptor binding pair. Neither the specific sequences nor the specific boundaries of such domains are critical, as long as binding activity is exhibited. Likewise, used in this context, binding characteristics necessarily includes a range of affinities, avidities and specificities, and combinations thereof, as long as binding activity is exhibited.

Biological Sample:

Any sample that may be obtained directly or indirectly from a subject, including whole blood, plasma, serum, tears, mucus, saliva, urine, pleural fluid, spinal fluid, gastric fluid, sweat, semen, vaginal secretion, sputum, fluid from ulcers and/or other surface eruptions, blisters, abscesses, and/or extracts of tissues, cells or organs. The biological sample may also be a laboratory research sample such as a cell culture supernatant. A sample analyzed using the disclosed methods can be collected or obtained using methods well known to those skilled in the art.

Carbodiimide:

A compound of the structure $R_1$—N=C=N—$R_2$, where $R_1$ and $R_2$ are independently hydrogen or hydrocarbyl groups. Specific examples include HN=C=NH, 1-ethyl-3-(3-dimethylamino propyl)carbodiimide; N,N'-dicyclohexyl-carbodiimide; and diisopropylcarbodiimide.

Cardiolipin:

Includes both natural cardiolipin and any modified cardiolipin that has structural similarity to naturally occurring cardiolipin, and which is capable of specifically binding to an anti-lipoidal antibody.

Cardiolipin Capture Area:

An area or region wherein cardiolipin is immobilized as the capture reagent. Can be one or more wells of a multi-well plate (such as an ELISA plate) or a region of a lateral flow device.

Capture Reagent:

An unlabeled specific binding partner that is specific for (i) an analyte, as in a sandwich assay, or (ii) a detector reagent or an analyte, as in a competitive assay, or for (iii) an ancillary specific binding partner, which itself is specific for the analyte, as in an indirect assay. As used herein, an "ancillary specific binding partner" is a specific binding partner that binds to the specific binding partner of an analyte. For example, an ancillary specific binding partner may include an antibody specific for another antibody, for example, goat anti-human antibody. A "capture area" is a region of a solid support where the capture reagent is immobilized. A solid support may have more than one capture area, for example, a "primary capture area," a "secondary capture area," and so on. A different capture reagent can be immobilized in the primary, secondary, or other capture areas. Multiple capture areas, for example of a lateral flow device, may have any orientation with respect to each other on the lateral flow substrate; for example, a primary capture area may be distal or proximal to a secondary (or other) capture area and vice versa. Alternatively, a primary capture area and a secondary (or other) capture area may be oriented perpendicularly to each other such that the two (or more) capture areas form a cross or a plus sign or other symbol.

Conjugate:

When used in the verb form, the term "conjugate" means the covalent coupling of one molecule (e.g., oxidized cardiolipin) to another molecule (e.g., a protein). Such coupling may be achieved by chemical means, either with or without the use of a linking group. When used in the noun form, the term "conjugate" means a coupled molecular complex formed by conjugation.

Detecting or Detection:

Refers to quantitatively or quantitatively determining the presence of the analyte(s) under investigation (e.g., anti-lipoidal antibodies and/or anti-*T. pallidum* antibodies, such as IgG, IgM, or IgA antibodies). "Detecting Formation of a Complex" refers to detecting a complex that includes a detector reagent by any method suitable for observing the particular label associated with the detector reagent; for instance, visual observation of a colored (or otherwise visible) label, measurement or visual detection of a fluorescent, chemiluminescent or radioactive label.

Detector Reagent (or Detection Reagent):

A specific binding partner that include (e.g., is conjugated to) a label. Detector reagents include, for example, labeled analyte-specific binding members (such as gold-conjugated, oxidized cardiolipin-attachment molecule complexes), or labeled ancillary specific binding members (such as enzyme-conjugate, goat anti-human antibodies).

Immunogenicity:

The property of being able to evoke an immune response within an organism. For example, oxidized cardiolipin retains immunogenicity when an anti-lipoidal antibody has the ability to bind an epitope present in oxidized cardiolipin.

Label:

Any molecule or composition bound to an analyte, analyte analog, detector reagent, or binding partner that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149;

4,313,734; 4,373,932; and 4,954,452, each incorporated by reference herein). Additional examples of useful labels include, without limitation, radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulfur particles, protein-adsorbed tellurium particles, protein-adsorbed carbon particles, and protein-coupled dye sacs. The attachment of a compound (e.g., a detector reagent) to a label can be through covalent bonds, adsorption processes, hydrophobic and/or electrostatic bonds, as in chelates and the like, or combinations of these bonds and interactions and/or may involve a linking group.

Figure 9:
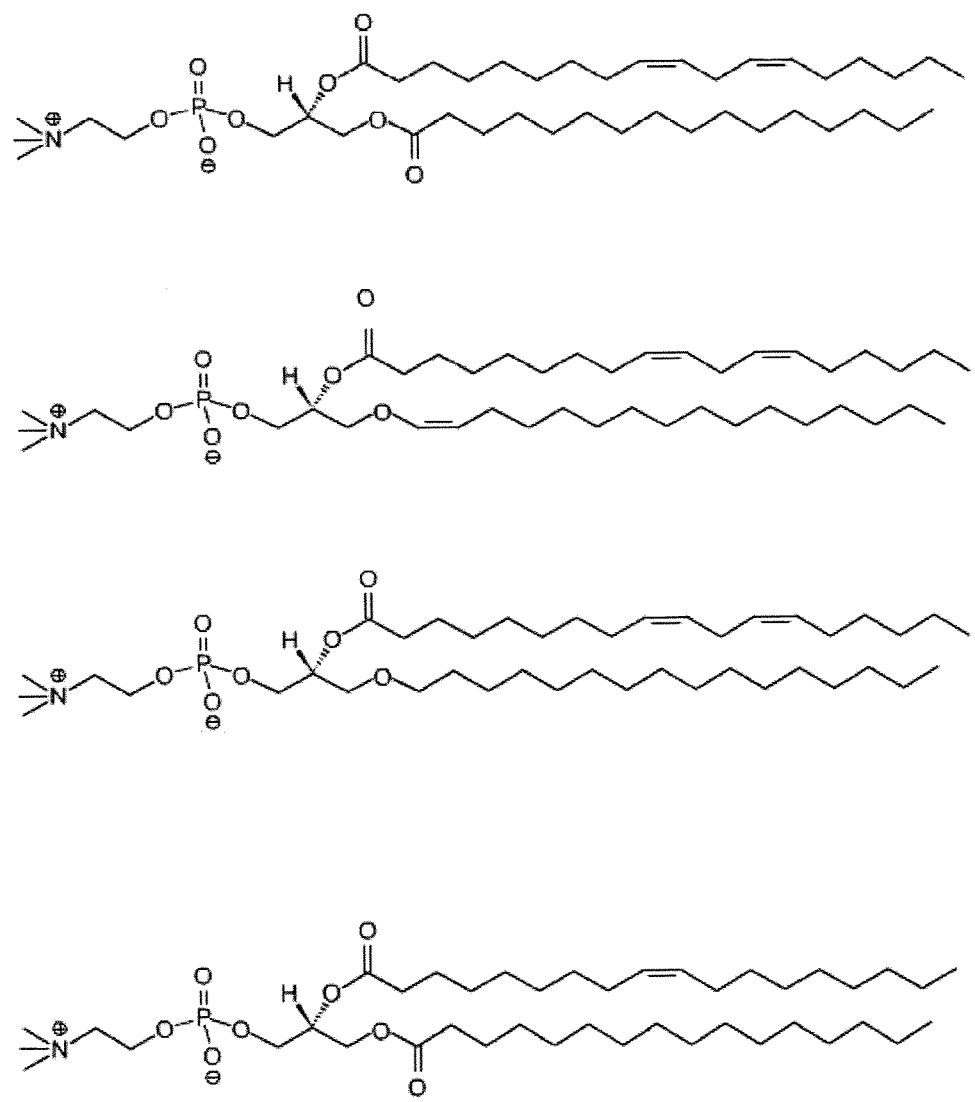
FIG. 9 shows the chemical structures of four representative naturally occurring phosphatidylcholine (lecithin) molecules. For L-α-phosphatidylcholine (heart, bovine), the molecular formula is $C_{42}H_{80}NO_8P$, the molecular weight is 758.07, the molecular weight (isotope) is 757.562157, and the percent composition is C 66.55% H 10.64% N 1.85% O 16.88% P 4.09%. For L-α-phosphatidylcholine, plasmalogen (heart, bovine), the molecular formula is $C_{42}H_{80}NO_7P$, the molecular weight is 742.07, the molecular weight (isotope) is 741.567242, and the percent composition is C 67.98% H 10.87% N 1.89% O 15.09% P 4.17%. For L-α-phosphatidylcholine, ether (heart, bovine), the molecular formula is $C_{42}H_{82}NO_7P$, the molecular weight is 744.09, the molecular weight (isotope) is 743.582893, and the percent composition is C 67.80% H 11.11% N 1.88% O 15.05% P 4.16%.

Lecithin (a.k.a., Phosphatidylcholine):

A glycerophospholipid, which is usually the most abundant phospholipid in animal and plants. It is a key building block of membrane bilayers, and is also the principal phospholipid circulating in the plasma. Phosphatidylcholine is a neutral or zwitterionic phospholipid over a pH range from strongly acid to strongly alkaline Phosphatidylcholine contains two fatty acid side chains, which may have variable chemical structures in nature and as modified synthetically. The chemical structures of four representative naturally occurring phosphatidylcholine molecules are shown in FIG. 9.

As used herein, the term "lecithin" includes both naturally occurring lecithins and any modified synthetic lecithin that has structural similarity to naturally occurring lecithin. For example, the fatty acids of synthetic lecithins may include the following:

| Carbon Number | 1-Acyl | 2-Acyl |
| --- | --- | --- |
| 14:0-16:0 | Myristoyl | Palmitoyl |
| 14:0-18:0 | Myristoyl | Stearoyl |
| 16:0-14:0 | Palmitoyl | Myristoyl |
| 16:0-18:0 | Palmitoyl | Stearoyl |
| 16:0-18:1 | Palmitoyl | Oleoyl |
| 16:0-18:2 | Palmitoyl | Linoleoyl |
| 16:0-20:4 | Palmitoyl | Arachidonoyl |
| 16:0-22:6 | Palmitoyl | Docosahexaenoyl |
| 18:0-14:0 | Stearoyl | Myristoyl |
| 18:0-16:0 | Stearoyl | Palmitoyl |
| 18:0-18:1 | Stearoyl | Oleoyl |
| 18:0-18:2 | Stearoyl | Linoleoyl |
| 18:0-20:4 | Stearoyl | Arachidonoyl |
| 18:0-22:6 | Stearoyl | Docosahexaenoyl |
| 18:1-14:0 | Oleoyl | Myristoyl |
| 18:1-16:0 | Oleoyl | Palmitoyl |
| 18:1-18:0 | Oleoyl | Stearoyl |
| 14:1-14:1 | Myristoleoyl | Myristoleoyl |
| 14:1-14:1 | Myristelaidoyl | Myristelaidoyl |
| 16:1-16:1 | Palmitoleoyl | Palmitoleoyl |
| 16:1-16:1 | Palmitelaidoyl | Palmitelaidoyl |
| 18:1-18:1 | Petroselinoyl | Petroselinoyl |
| 18:1-18:1 | Oleoyl | Oleoyl |
| 18:1-18:1 | Elaidoyl | Elaidoyl |
| 18:2-18:2 | Linoleoyl | Linoleoyl |
| 18:3-18:3 | Linolenoyl | Linolenoyl |
| 20:1-20:1 | Eicosenoyl | Eicosenoyl |
| 20:4-20:4 | Arachidonoyl | Arachidonoyl |
| 22:1-22:1 | Erucoyl | Erucoyl |
| 22:6-22:6 | DHA | DHA |
| 24:1-24:1 | Nervonoyl | Nervonoyl |

Linking Group:

A chemical arm between two compounds, for instance a compound and a label (e.g., an analyte and a label). To accomplish the requisite chemical structure, each of the reactants must contain a reactive group. Representative combinations of such groups are amino with carboxyl to form amide linkages; carboxy with hydroxy to form ester linkages or amino with alkyl halides to form alkylamino linkages; thiols with thiols to form disulfides; or thiols with maleimides or alkylhalides to form thioethers. Hydroxyl, carboxyl, amino and other functionalities, where not present in the native compound, may be introduced by known methods.

Likewise, a wide variety of linking groups may be employed. The structure of the linkage should be a stable covalent linkage formed to attach two compounds to each other (e.g., the label to the analyte). In some cases the linking group may be designed to be either hydrophilic or hydrophobic in order to enhance the desired binding characteristics, for instance of the modified ligand and its cognate receptor. The covalent linkages should be stable relative to the solution conditions to which linked compounds are subjected. Examples of linking groups will be from 1-20 carbons and 0-10 heteroatoms (NH, O, S) and may be branched or straight chain. Without limiting the foregoing, it should be obvious that only combinations of atoms that are chemically compatible comprise the linking group. For example, amide, ester, thioether, thiol ester, keto, hydroxyl, carboxyl, ether groups in combinations with carbon-carbon bonds are particular examples of chemically compatible linking groups.

Operable or Contiguous Contact:

Two solid components are in operable contact when they are in contact, either directly or indirectly, in such a manner that an aqueous liquid can flow from one of the two components to the other substantially uninterruptedly, by capillarity or otherwise. Direct or contiguous contact means that the two elements are in physical contact, such as edge-to-edge or front-to-back. When two components are in direct contact, they may overlap with an overlap of about 0.5 to about 3 mm. However, the components can be placed with abutting edges. "Indirect contact" means that the two elements are not in physical contact, but are bridged by one or more conductors. Operable contact can also be referred to as "fluid transmitting" or "fluid continuous" contact.

Oxidized Cardiolipin (or Modified Cardiolipin):

Cardiolipin that has been chemically modified as described herein. For example, oxidized cardiolipin is a mixed population of chemically related molecules where at least one of the four fatty acid chains in non-oxidized cardiolipin have been oxidatively cleaved to produce a terminal carboxyl group. In some embodiments, oxidized cardiolipin has a chemical structure shown in FIG. 3.

Reducing Agent:

Any reducing agent that reduces a β-ketone group resulting from cardiolipin oxidation to the corresponding β-hydroxyl without effecting substantial degradation of other oxidized cardiolipin functional groups, such as the fatty acid ester groups and/or the phosphate esters. A person of ordinary skill in the art can select suitable reducing agents from, for example, those taught by Larock, *Comprehensive Organic Transformations,* 2nd Edition, New York: John Wiley & Sons, 1999. Particular examples of reducing agents include sodium bisulfite, dimethyl sulfide, sodium cyanoborohydride ($NaBH_3CN$), sodium borohydride ($NaBH_4$), sodium triacetoxyborohydride ($NaBH(OAc)_3$), morpholine borane, potassium triisopropoxyborohydride, t-butyl amine borane, dimethylamine borane, pyridine borane, triethylamine borane, trimethylamine borane.

Sample Application Area:

An area where a fluid sample is introduced to an immunochromatographic test strip, such as an immunochromatographic test strip present in a lateral flow device. In one example, the sample may be introduced to the sample application area by external application, as with a dropper or other applicator. In another example, the sample application area may be directly immersed in the sample, such as when a test strip is dipped into a container holding a sample. In yet another example, the sample may be poured or expressed onto the sample application area.

Solid Support (or Substrate):

Any material which is insoluble, or can be made insoluble by a subsequent reaction. Numerous and varied solid supports are known to those in the art and include, without limitation, nitrocellulose, the walls of wells of a multi-well plate, test tubes, polystyrene beads, magnetic beads, membranes, microparticles (such as latex particles), and sheep (or other animal) red blood cells. Any suitable porous material with sufficient porosity to allow access by detector reagents and a suitable surface affinity to immobilize capture reagents (e.g., oxidized cardiolipin or oxidized cardiolipin-attachment molecule complexes) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

The surface of a solid support may be activated by chemical processes that cause covalent linkage of an agent (e.g., a capture reagent) to the support. However, any other suitable method may be used for immobilizing an agent (e.g., a capture reagent) to a solid support including, without limitation, ionic interactions, hydrophobic interactions, covalent interactions and the like. The particular forces that result in immobilization of an agent on a solid phase are not important for the methods and devices described herein.

A solid phase can be chosen for its intrinsic ability to attract and immobilize an agent, such as a capture reagent. Alternatively, the solid phase can possess a factor that has the ability to attract and immobilize an agent, such as a capture reagent. The factor can include a charged substance that is oppositely charged with respect to, for example, the capture reagent itself or to a charged substance conjugated to the capture reagent. In another embodiment, a specific binding member may be immobilized upon the solid phase to immobilize its binding partner (e.g., a capture reagent). In this example, therefore, the specific binding member enables the indirect binding of the capture reagent to a solid phase material.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

Specific Binding Partner (or Binding Partner):

A member of a pair of molecules that interact by means of specific, noncovalent interactions that depend on the three-dimensional structures of the molecules involved. Typical pairs of specific binding partners include antigen/antibody, hapten/antibody, hormone/receptor, nucleic acid strand/complementary nucleic acid strand, substrate/enzyme, inhibitor/enzyme, carbohydrate/lectin, biotin/(strept)avidin, and virus/cellular receptor.

The phrase "specifically binds to an analyte" or "specifically immunoreactive with," when referring to an antibody, refers to a binding reaction which is determinative of the presence of the analyte in the presence of a heterogeneous population of molecules such as proteins and other biologic molecules. Thus, under designated immunoassay conditions, the specified antibodies bind to a particular analyte and do not bind in a significant amount to other analytes present in the sample. A variety of immunoassay formats may be used to select antibodies specifically immunoreactive with a particular analyte. For example, ELISA immunoassays are routinely used to select antibodies specifically immunoreactive with a protein. See Harlow and Lane, *Antibodies, A Laboratory Manual*, CSHP, New York (1988), for a description of immunoassay formats and conditions that can be used to determine specific immunoreactivity.

Subject:

Living multi-cellular organisms, including vertebrate organisms, a category that includes both human and non-human mammals. In one example, a subject is a human subject having or suspected of having syphilis or an anti-cardiolipin autoimmune disease, such as lupus.

Treponemal Antigen (TA):

An antigen containing at least one antigenic determinant that specifically binds anti-*T. pallidum* antibodies. Numerous treponemal antigens have been described in the art; see, for example, U.S. Pat. Nos. 6,479,248; 6,248,331; 5,681,934; 5,578,456; 4,868,118; and 4,740,467, each of which is incorporated herein by reference. For instance, polypeptides of at least the following apparent molecular weights have been described as *T. pallidum* antigens: 16-20 kDa, 18 kDa, 18-23 kDa, 25 kDa, 35 kDa, 37 kDa, 37-46 kDa, 38 kDa, 39 kDa, 41 kDa, 43 kDa, 44 kDa, 46 kDa, 47 kDa, 58 kDa, 150 kDa; and 180 kDa (for more particular detail, see U.S. Pat. No. 4,846,118). Methods of detecting TAs are known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Cardiolipin

Cardiolipin is diphosphatidyl glycerol (specifically, 1,3-diphosphatidylglycerol), which, as shown below, has a backbone consisting of three molecules of glycerol joined by two phosphodiester bridges:

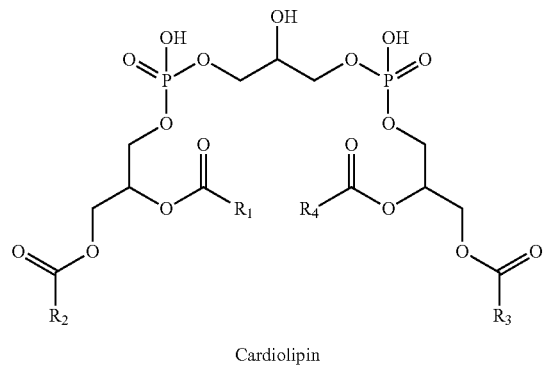

Cardiolipin

The four hydroxyl groups of cardiolipin's external glycerol moieties are each esterified with a saturated or unsaturated fatty acid chain (typically from 14 to 18 carbons in length). As used herein, the term "cardiolipin" contemplates 1,3-diphosphatidylglycerol having any distribution of fatty acid side chains; provided that at least one fatty acid side chain has at least one C=C double bond. Thus, the four fatty acid side chains of cardiolipin can independently vary in length (e.g., from about 14 to about 25 carbons, from about 14 to about 22 carbons, from about 14 to about 20 carbons, from about 14 to about 18 carbons, or from about 14 to about 16 carbons) and/or degree of saturation (e.g., from completely saturated to having about 6 double bonds, from completely saturated to having about 4 double bonds, or from completely saturated to having about 2 double bonds). Exemplary fatty acid side chains of cardiolipin independently include myristoyl (14:0); palmitoyl (16:0); stearoyl (18:0); oleoyl (18:1); myristoleoyl (14:1); palmitoleoyl (16:1); petroselinoyl (18:1); linoleoyl (18:2); linolenoyl (18:3); eicosenoyl (20:1); arachidonoyl (20:4); erucoyl (22:1); DHA (22:6); or nervonoyl (24:1).

In some embodiments, cardiolipin is a naturally occurring form. Naturally occurring cardiolipin is commercially available from a number of sources, for example, Sigma Aldrich, Avanti Polar Lipids (Alabaster, Ala.), and Lee Laboratories (Grayson, Ga.). It also can be derived, for example, by solvent extraction of beef heart muscle tissue, by a precipitation method, or by high pressure column chromatography. The fatty acid composition of naturally occurring cardiolipin is generally distributed according to a wide variety of natural occurring fatty acids such as palmitoyl (16:0); stearoyl (18:0); oleoyl (18:1); and linoleoyl (18:2). The most abundant fatty acid molecular species in naturally occurring forms of cardiolipin are linoleic acid at 90%, followed by oleic acid at 5%, and palmitric acid at 1%.

In other embodiments, cardiolipin is a non-naturally occurring form (also referred to as "synthetic cardiolipin"). Non-limiting examples of synthetic cardiolipin include, for example, tetraoleoyl cardiolipin, bis(dipalmitoyl D,L-α-glycerylphosphoryl)-1,3 glycerol benzyl ether disodium salt, bis(dipalmitoyl D,L-α-glycerylphosphoryl)-1,5 pentanediol disodium salt, bis(dipalmitoyl D,L-α-glycerylphosphoryl)-1,3 propanediol disodium sal, bis(dipalmitoyl D,L-α-glycerylphosphoryl)-1,4 butanediol disodium salt, bis(dipalmitoyl D,L-α-glycerylphosphoryl)-1,2 ethanediol disodium salt, bis (dipalmitoyl D,L-α-glycerylphosphoryl)-methanediol disodium salt, bis(dipalmitoyl D,L-α-glycerylphosphoryl)-1,3 glycerol disodium salt, bis(benzylphosphoryl)-1,3-propanediol disodium salt, or D,L-α-dipalmitoyl bis-phosphatidic acid.

The antigenic epitope of cardiolipin is believed to involve the two phosphate groups and the β-hydroxyl group of the central glycerol moiety. This antigenic epitope is present in both naturally occurring and synthetic cardiolipins. Either or both naturally occurring cardiolipins or synthetic cardiolipins may be oxidized as described herein as long as anti-lipoidal antibodies will specifically bind to the oxidized form.

IV. Oxidation of Cardiolipin

A. Generally

One of ordinary skill in the art will appreciate that oxidative cleavage of the fatty acid side chains of cardiolipin will occur in the presence of oxidizing agents, such as $NaIO_4$ and $KMnO_4$, or $NaIO_4$ and ruthenium tetroxide, or $HIO_4$ and $KMnO_4$ (see, e.g., March, *Advanced Organic Chemistry: Reactions, Mechanisms and Structure*, Second Edition, New York: McGraw Hill Book Company, 1977, page 1095). That is, the double bonds present in the fatty acid side chains would be oxidized ultimately to carboxyl groups, thereby releasing an alkyl carboxylate, such as malonic acid and/or caproic acid (as shown in FIG. 3). In a completely oxidized cardiolipin molecule, all four fatty acid side chains will be cleaved at the first (most proximal) double bond position(s) to produce fatty acid chains each with a terminal carboxyl group (as shown in FIG. 3). Because naturally occurring cardiolipin may be heterogeneous with regard to its fatty acid side chain composition, a completely oxidized cardiolipin preparation will be a mixture of oxidized species reflecting the fatty acid side chain heterogeneity in the non-oxidized molecule. Additional heterogeneity may arise if cardiolipin oxidation is incomplete. In that situation, a mixture of oxidized cardiolipin species where 1, 2 or 3 of the fatty acid side chains are oxidized to carboxylic acid(s) will be produced (see, e.g., FIG. 3 for an example of an oxidized cardiolipin molecule with one terminal carboxyl group illustrative of incomplete oxidation, and another example of an oxidized cardiolipin which has undergone complete oxidation). Any or all of the oxidized cardiolipin species described in this paragraph are contemplated herein as being useful in the described compositions, methods, and devices.

B. Oxidation of Cardiolipin by $NaIO_4$ and $KMnO_4$

One method useful for the oxidation of cardiolipin employs periodate ($IO_4^-$) and/or permanganate ($MnO_4^-$) as the oxidizing agents. Salts of these oxidizing agents include any counterion that provides an electrically neutral compound. The periodate is typically in the form of a periodate salt, such as $NaIO_4$ or $HIO_4$ (periodic acid), and the permanganate is typically in the form of a salt (such as a sodium or potassium salt), for example $KMnO_4$. In one specific embodiment, $NaIO_4$ and $KMnO_4$ are used as oxidizing agents. To practice this oxidation method, cardiolipin obtained from any source may be added to any solvent in which the cardiolipin will substantially dissolve. In view of the hydrophobic nature of cardiolipin, the use of a polar organic solvent, such as t-butanol, ethanol, methanol, propanol, acetone, dimethylformamide, or diethyl ether is preferable. Other non-polar organic solvents may be used to suspend cardiolipin, such as chloroform; however, these non-polar organic solvents are less useful because other components of the oxidation reaction (as described below) are less soluble in these solvents than, for example, a polar organic solvent or an aqueous solvent.

The concentration of the cardiolipin solution may be any useful concentration that, in the upper range, still permits cardiolipin to dissolve in the chosen solvent. One of skill in the art can easily determine the saturation point for cardiolipin in any particular solvent. In examples where t-butanol is the chosen solvent, cardiolipin concentrations may be in the range of about 10 mg/ml to 250 mg/ml, such as about 10 mg/ml, about 25 mg/ml, about 50 mg/ml, about 75 mg/ml, about 100 mg/ml, about 125 mg/ml, about 150 mg/ml, about 200 mg/ml and about 250 mg/ml. If particulates are present after dissolving cardiolipin in the chosen solvent, the solution may, optionally, be clarified by any technique known in the art, such as centrifugation or filtration.

In some embodiments, oxidation of cardiolipin may take place in the absence of oxygen, for example in an argon, helium, or nitrogen atmosphere. A cardiolipin oxidation reaction will occur in an oxygen-containing atmosphere, such as air, or other atmosphere; however, oxidizing molecules contained therein, such as carbonates, may decrease the efficiency of the reaction. Nonetheless, all atmospheres in which the cardiolipin oxidation reaction will occur, regardless of reaction efficiency, are contemplated by this disclosure.

Amounts of oxidizing agents such as $NaIO_4$ and $KMnO_4$, sufficient to oxidatively cleave at least one cardiolipin fatty acid side chain are then added to the suspended cardiolipin with constant stirring. In some examples, the periodate and permanganate (such as $NaIO_4$ and $KMnO_4$) are used in combination to oxidize cardiolipin. In certain of those examples, the periodate (such as $NaIO_4$) is added to the cardiolipin solution prior to the addition of the permanganate (such as $KMnO_4$). The oxidizing agents may be dissolved in any solvent in which they are soluble and that will mix with the cardiolipin solution. For example, $NaIO_4$ and $KMnO_4$ may be dissolved in water.

Where $NaIO_4$ is used in a method to oxidize cardiolipin, the amount of $NaIO_4$ used in the reaction is not critical. Minimally, the amount is such that the reaction takes place in a reasonable time under the particular circumstances. At the other end of the spectrum, a considerable molar excess of $NaIO_4$ may be used in the oxidation reaction. For example, the molar ratio of periodate (such as $NaIO_4$) to cardiolipin can be about 0.1:1 to about 100:1, about 0.5:1 to about 50:1, about 1:1 to about 25:1, about 2:1 to about 15:1, about 2.5:1 to about 10:1, about 3:1 to about 7.5:1, or about 4:1 to about 5:1. In specific embodiments, the molar ratio of sodium m-periodate to cardiolipin is about 4:1 to 5:1, or more specifically about 4.2:1.

Where permanganate (such as $KMnO_4$) is used in a method to oxidize cardiolipin, the amount of permanganate used in the reaction is not critical. Minimally, the amount is such that the reaction takes place in a reasonable time under the particular circumstances. At the other end of the spectrum, a considerable molar excess of permanganate may be used in the oxidation reaction. For example, the molar ratio of permanganate (such as $KMnO_4$) to cardiolipin can be about 0.01:1 to about 100:1, about 0.02:1 to about 50:1, about 0.1:1 to about 25:1, about 0.25:1 to about 15:1, about 0.3:1 to about 10:1, about 0.4:1 to about 7.5:1, about 0.5:1 to about 5:1, about 0.6:1 to about 2:1, or about 0.7:1 to about 1:1. In specific embodiments, the molar ratio of the permanganate (such as $KMnO_4$) to cardiolipin is about 0.5:1 to 1:1, or more specifically about 0.75:1.

The oxidation reaction mixture may take place at any temperature that does not stop the reaction from occurring. Similarly, the reaction may proceed for any amount of time that is sufficient to cause oxidative cleavage of at least one fatty acid side chain of cardiolipin. As one of skill in the art will appreciate, reaction time will depend upon several variables, including reaction temperature, type of solvent, and reactant and product concentrations, each of which variables may be easily optimized with routine experimentation. In one example, the oxidation reaction occurs at room temperature and proceeds for at least 24-48 hours.

The cardiolipin oxidation reaction may be stopped with any reducing agent capable of neutralizing the oxidizing agent(s) present in the reaction and capable of reducing any ketone formed at the β-carbon of the central glycerol moiety to the corresponding β-hydroxyl group. A reducing agent, such as a bisulfite salt (such as, sodium bisulfite), dimethyl sulfide, sodium cyanoborohydride ($NaBH_3CN$), sodium borohydride ($NaBH_4$), sodium triacetoxyborohydride ($NaBH(OAc)_3$), morpholine borane, potassium triisopropoxyborohydride, t-butyl amine borane, dimethylamine borane, pyridine borane, triethylamine borane, or trimethylamine borane, is useful for this purpose. In some specific examples, the reducing agent is a bisulfite salt, and in more particular examples, the reducing agent is sodium bisulfite.

The amount of reducing agent added to the reaction is not critical as long as the oxidizing agents are quenched. If immunogenicity of oxidized cardiolipin is adversely affected by oxidation to a ketone of the β-hydroxyl groups of cardiolipin central glycerol moieties, then an amount of reducing agent is also an amount that will restore β-hydroxyl groups for sufficient immunogenicity of the oxidized cardiolipin. For example, an amount of sodium bisulfite may be added to a cardiolipin oxidation reaction containing $NaIO_4$ and $KMnO_4$ oxidizing agents sufficient to cause the reaction mixture to turn substantially colorless.

If present, aqueous and organic phases in a cardiolipin oxidation reaction may be separated by any method known in the art, for example centrifugation. In one embodiment, a t-butanol phase containing primarily oxidized cardiolipin and a water phase containing primarily alkyl carboxylates may be separated by centrifugation. Oxidized cardiolipin is sufficiently hydrophobic that it may be expected to separate into an organic phase. However, if necessary, an ordinarily skilled artisan may determine which of an aqueous or organic phase (or both) contains oxidized cardiolipin by methods known in the art, such as TLC, HPLC, NMR or gas chromatography.

Optionally, oxidized cardiolipin in solution may be dialyzed into a useful buffer, such as 10 mM phosphate buffer, pH 8.0, and lyophilized to dryness using methods well known in the art.

C. Antigenicity of Oxidized Cardiolipin

Oxidation has been shown to alter the antigenic properties of some phospholipids (see, e.g., U.S. Pat. No. 6,177,282). It is believed that anti-lipoidal antibodies of syphilitic patients bind the two phosphate groups and the β-hydroxyl group of the central glycerol moiety (see, e.g., Castro et al., *Clin. Diagn. Lab. Immunol.*, 7(4):658-661, 2000). Thus, it is beneficial to maintain the configuration of the central glycerol moiety in order to retain cardiolipin antigenicity, for example, to detect anti-lipoidal antibodies in syphilitic sera. The antigenicity of oxidized cardiolipin may be tested by any of a number of widely used techniques (including, e.g., ELISA, dot blot, enzyme immunoassay, fluorescence immunoassay)

and/or as described herein (see, e.g., Example 4). As shown in Example 4 (below), methods of oxidizing cardiolipin described herein maintain cardiolipin antigenicity.

D. Cardiolipin/Lecithin Mixtures

Mixtures of cardiolipin and lecithin may be oxidized by the same methods described above for cardiolipin alone; the only difference being that the starting material is a mixture of cardiolipin and lecithin. In the initial oxidation reaction, cardiolipin and lecithin can be mixed together in a weight ratio (cardiolipin:lecithin) between about 20:1 to about 1:1, or between about 1:1 to about 1:10, or between about 10:1 to about 1:10, or between about 5:1 to about 1:5, or between about 1:1 to about 1:5. In particular examples, the weight ratio of cardiolipin:lecithin includes about 20:1, about 10:1, about 5:1, about 2:1, about 1:1, about 1:2, about 1:3, about 1:5, or about 1:10.

V. Oxidized Cardiolipin Attachment Molecule Complex

Figure 11:
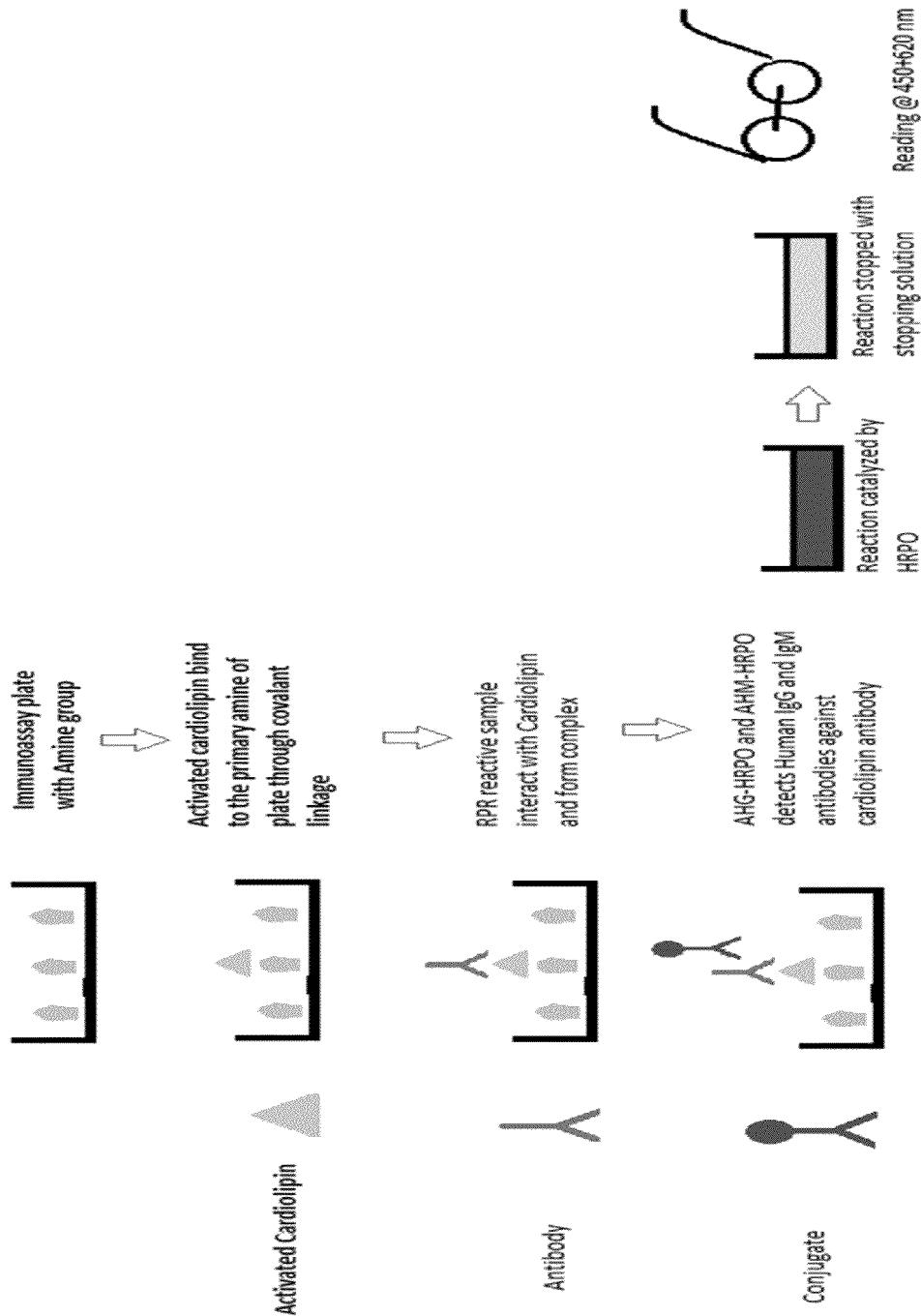
FIG. 11 is a diagram showing how the disclosed oxidized cardiolipin coated multi-well plates disclosed herein can be used to detect anti-cardiolipin antibodies.

In some examples oxidized cardiolipin is attached to the surface of a multi-well plate (or other solid substrate) that includes amine groups. For example, as shown in FIG. 11, immunoassay plates containing amine groups can be used. Such plates are commercially available (for example Nunc Immobilizer Amine 12×8 Strips Cat #436013). As shown in FIG. 11, the oxidized/activated cardiolipin is added to the wells of the plate, the permitting binding of the activated oxidized cardiolipin to the plate through a covalent linkage. A sample containing or suspected of containing cardiolipin antibodies can then be added to the wells: if cardiolipin antibody is present in the sample, it will bind to the cardiolipin present in the wells, forming a complex between the cardiolipin and the antibodies. Bound cardiolipin antibodies can then be detected, for example using labeled anti-human IgG and/or anti-human IgM (such as goat anti-human (AHG) antibodies). In some examples, the label is HRP, and the reaction is stopped with a stopping solution. The HRP can then be reacted to permit its detection at 450 nm.

In other examples, oxidized cardiolipin is attached to the surface of a multi-well plate (or other solid substrate) that does not include amine groups (such as MaxiSorp 96 well Cat #439454), but are instead coated with a protein (such as IgY, BSA, or KLH) to permit attachment of the cardiolipin. Thus, in FIG. 11, instead of using a plate having wells containing amino groups, a plate having wells coated with a carrier protein (or other attachment molecule) can be used. Suitable attachment molecules include proteins, polypeptides or peptides such as albumin, hemocyanin, thyroglobulin and derivatives thereof, particularly bovine serum albumin (BSA) and keyhole limpet hemocyanin (KLH), avidin, streptavidin, and biotin. Other polypeptide-derived or non-polypeptide derived substances are known to those skilled in the art. The oxidized/activated cardiolipin is added to the wells of the plate, the permitting binding of the activated oxidized cardiolipin to the plate through a covalent linkage to the bound carrier proteins. The other steps remain the same.

Oxidized cardiolipin is a relatively small molecule. Thus, it can beneficial to attach oxidized cardiolipin to a solid support using a larger molecule (such as a polypeptide). In certain examples, the larger molecule is more readily attached to a substrate, such as a bibulous substrate of the type that is used in lateral flow or flow-through technology. The derivatized oxidized cardiolipin is more readily adsorbed and localized to a porous substrate (such as a nitrocellulose porous substrate) than the very small cardiolipin or oxidized cardiolipin molecule itself.

Attachment molecules can contain a reactive group to facilitate covalent conjugation to the oxidized cardiolipin. The amine group of amino acids can be used in this manner Attachment molecules lacking such groups can often be reacted with an appropriate chemical to produce reactive groups. Illustrative chemicals that can be used to produce useful reactive groups in an attachment molecule include, without limitation 1-ethyl-3-(3-dimethylamino propyl)carbodiimide (EDC), and N-hydroxysulfosuccinimide (NHS).

The provision of oxidized cardiolipin herein provides at least one reactive carboxyl group, which is not otherwise available in naturally occurring or synthetic cardiolipins. Thus, oxidized cardiolipin may be linked via an oxidation-created reactive group to an attachment molecule by any means known in the art and/or as described herein. Such linkage may be either with or without an additional linking group. Many different methods may be used to produce a linkage between oxidized cardiolipin and an attachment molecule.

Figure 4:
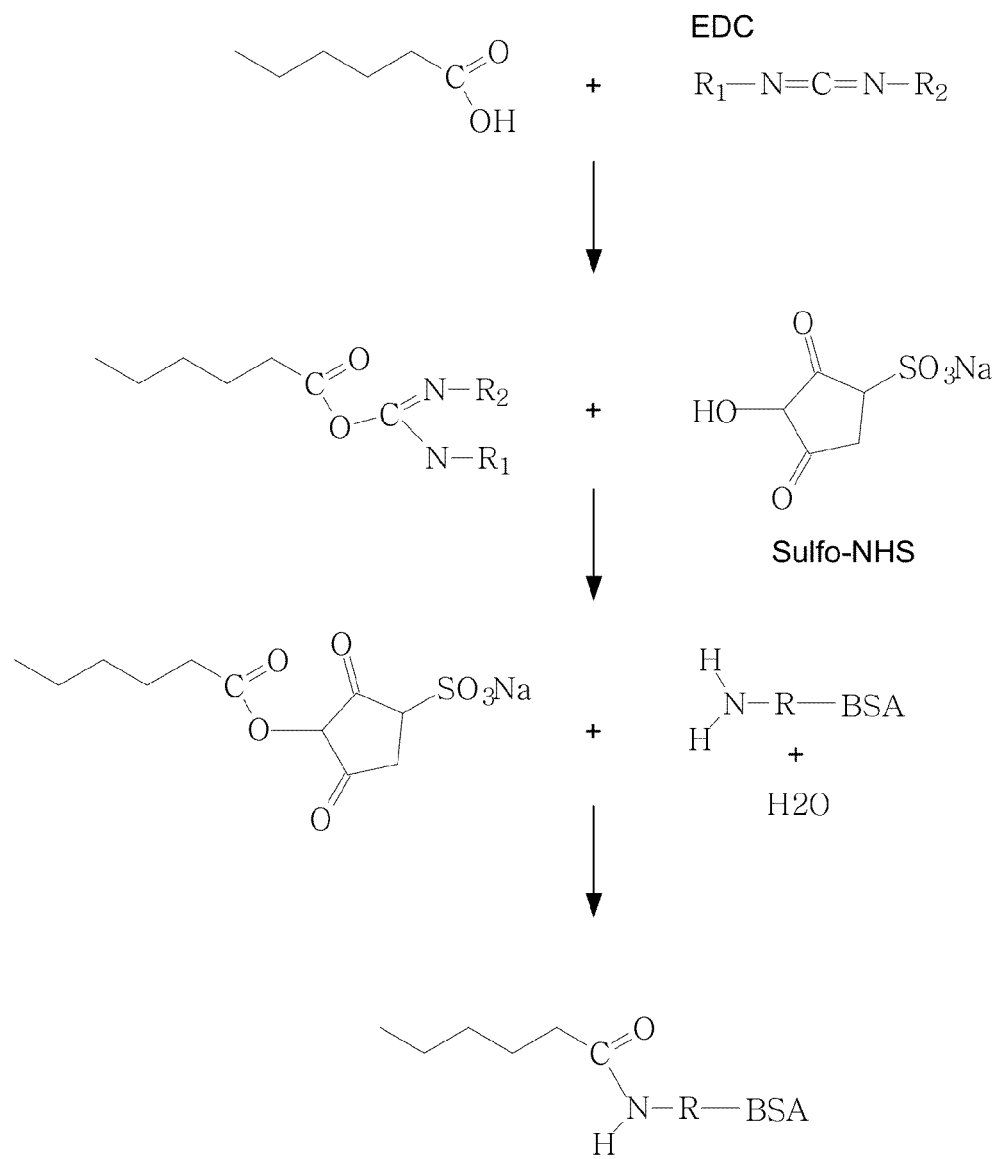
FIG. 4 shows a schematic reaction useful for covalently linking oxidized cardiolipin to amine-containing attachment molecules, such as a protein. In the illustrated example, the attachment molecule is BSA.

One example method that may be used to link oxidized cardiolipin to an amine-containing attachment molecule (e.g., a protein, such as BSA, synthetic protein MAPS, IgY, strepavidin, avidin or KLH) is shown schematically in FIG. 4. The reaction in FIG. 4 illustrates that a carboxyl group created by oxidative cleavage of a cardiolipin fatty acid side chain, as described herein, may be modified to an amine-reactive NHS ester using EDC in combination with NHS (or Sulfo-NHS, as shown in FIG. 4). The oxidized cardiolipin NHS ester will then react with amine groups present in an attachment molecule, such as BSA as shown in FIG. 4, to form an amide linkage between oxidized cardiolipin and the attachment molecule.

Some embodiments of the methods and devices herein make use of oxidized cardiolipin or oxidized cardiolipin-attachment molecule complex immobilized on solid phases. Any conventional method of immobilizing a substance on a solid surface is contemplated in this disclosure.

Suitable methods for immobilizing oxidized cardiolipin or oxidized cardiolipin-attachment molecule complex on solid phases include ionic, hydrophobic, covalent interactions and the like. The solid phase (see, e.g., Section II) can be chosen for its intrinsic ability to attract and immobilize oxidized cardiolipin or oxidized cardiolipin-attachment molecule complex. Alternatively, the solid phase can possess a factor that has the ability to attract and immobilize oxidized cardiolipin or oxidized cardiolipin-attachment molecule complex. The factor can include, for example, a charged substance that is oppositely charged with respect to oxidized cardiolipin or oxidized cardiolipin-attachment molecule complex, or, for example, a charged substance that is oppositely charged with respect to a charged substance conjugated to oxidized cardiolipin or oxidized cardiolipin-attachment molecule complex. In one example, the solid phase includes an amine group. As yet another alternative, the factor can be any specific binding partner, for example, avidin or streptavidin, which is immobilized upon the solid phase and which has the ability to immobilize oxidized cardiolipin or oxidized cardiolipin-attachment molecule complex, for example, biotinylated oxidized cardiolipin, through a specific binding reaction.

In some embodiments of methods and devices herein, oxidized cardiolipin or oxidized cardiolipin-attachment molecule complex may serve as a detector reagent, and thus will be conjugated to a label. Any molecule or composition that is detectable by spectroscopic, photochemical, biochemical, immunochemical, electrical, optical or chemical means may serve as a label. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, co-factors, ligands, chemiluminescent or fluorescent agents, protein-adsorbed silver particles, protein-adsorbed iron particles, protein-adsorbed copper particles, protein-adsorbed selenium particles, protein-adsorbed sulfur particles, protein-adsorbed tellurium particles, protein-adsorbed carbon particles, and protein-coupled dye sacs.

The attachment of a compound to a label can be through covalent bonds, adsorption processes, hydrophobic and/or electrostatic bonds, as in chelates and the like, or combinations of these bonds and interactions, and/or may involve a linking group. Methods for labeling and guidance in the choice of labels appropriate for various purposes are discussed, for example, in Sambrook et al., *Molecular Cloning: A Laboratory Manual*, CSHL, New York, 1989 and Ausubel et al., *Current Protocols in Molecular Biology*, Greene Publ. Assoc. and Wiley-Intersciences, 1998.

In some embodiments of methods and devices, colloidal gold conjugates of oxidized cardiolipin or colloidal gold conjugates of oxidized cardiolipin-attachment molecule complexes are envisaged.

VI. Immunoassay Devices

The provided method to oxidize cardiolipin and prepare cardiolipin-attachment molecule conjugates, which can be immobilized on a solid support (such as a well of a multi-well plate, or a microporous membrane, like nitrocellulose, nylon or PVDF) enables solid-surface-based immunoassays (such as, EIA, ELISA, flow-through devices, dipsticks, and lateral flow devices) for the detection of cardiolipin-binding analytes (such as anti-lipoidal antibodies in biological samples from *T. pallidum*-infected subjects). In some examples, a disclosed immunoassay permits detection of the presence (or absence) of anti-lipoidal antibodies (such as IgG and IgM,) in a biological sample for diagnosis of syphilis. IgG and IgM anti-lipoidal antibodies can be detected qualitatively or quantitatively.

A. Representative Immunoassay Device Formats and Related Information

Immunoassay devices permit the performance of relatively inexpensive, disposable, assays for the identification of the presence (or absence) of an analyte in a liquid sample. In one example devices are formatted as freestanding dipsticks (e.g., test strips) or as devices having some sort of housing. In another example devices are formatted as a multi-well plate, such as a 96-well ELISA plate. In some examples, an immunoassay device can be used with as little as about 200 µl of liquid sample, and detection of an analyte in the sample can (but need not) be complete within 1-2 hours. In clinical assays, the sample may be urine, blood, serum, saliva, or other body fluids. In nonclinical tests, the sample may be a small volume of solution prepared from soil, dust, plants, or food.

Immunoassay devices have been developed for identification or monitoring of physiological and pathological conditions (e.g., infectious diseases, pregnancy, cancer, endocrine disorders) using different biological samples (e.g., urine, serum, plasma, blood, saliva), and for analysis of environmental samples (e.g., natural fluids and industrial plant effluents) for instance for contamination. Many of these tests are based on the highly specific interactions between specific binding pairs. Examples of such binding pairs include antigen/antibody, hapten/antibody, lectin/carbohydrate, apoprotein/cofactor and biotin/(strept)avidin. Furthermore, many of these tests involve devices (e.g., solid phase, lateral flow test strips, flow-through tests) with one or more of the members of a binding pair attached to a mobile or immobile solid phase material such as a multi-well plate, latex beads, glass fibers, glass beads, cellulose strips or nitrocellulose membranes (U.S. Pat. Nos. 4,703,017; 4,743,560; 5,073,484).

One category of immunoassay is the "sandwich" assay. In general, sandwich immunoassay procedures include contacting the sample that may contain the analyte to be assayed, for example, anti-lipoidal antibody, with an antigen recognized by the analyte, for example, oxidized cardiolipin, and in some examples also a detector reagent (such as one linked to a label or another detectable reagent, such as dyed latex, a colloidal metal sol, or a radioisotope). In one example the detector reagent is protein A or a labeled anti-human secondary antibody (such as a goat, rabbit, or mouse anti-human secondary antibody, labeled with, e.g., an enzyme, colloidal gold, etc.). The presence of the oxidized cardiolipin-anti-lipoidal antibody complex is indicated if the label is detected, and is not indicated if the label is not detected (e.g., above a threshold level). This technique can be used to obtain quantitative or semi-quantitative results. Examples of sandwich immunoassays performed on test strips are described in U.S. Pat. Nos. 4,168,146 and 4,366,241.

Solid phase immunoassay devices (such as a multi-well plate, such as an ELISA plate) provide sensitive detection of analytes in biological fluid samples. Solid phase immunoassay devices incorporate a solid support to which one member of a ligand-receptor pair, usually an antibody, antigen, or hapten, is bound. Common forms of solid supports include plates, tubes, or beads of polystyrene, nylon, nitrocellulose, cellulose acetate, glass fibers, and other porous polymers.

In general, a fluid sample (or a sample suspended in a fluid) is introduced into wells of a multi-well plate containing conjugated or bound oxidized cardiolipin (and in some examples also conjugated or bound TAs, which may be in the same or different wells as the oxidized cardiolipin). A sample is collected or obtained using methods well known to those skilled in the art. The sample containing or suspected of containing anti-lipoidal (and in some examples also anti-treponemal) antibodies to be detected may be obtained from any biological source. Examples of biological sources include blood serum, blood plasma, urine, spinal fluid, saliva, fermentation fluid, lymph fluid, tissue culture fluid and ascites fluid of a human or animal. The sample may be diluted, purified, concentrated, filtered, dissolved, suspended or otherwise manipulated prior to immunoassay to optimize the immunoassay results. The sample is incubated with the oxidized cardiolipin under conditions sufficient for any anti-lipoidal antibodies in the sample to bind to the oxidized cardiolipin, to form a complex. The complex between an analyte (such as an anti-lipoidal antibody) and a capture reagent (such as oxidized cardiolipin) can be detected using a detector reagent, such as anti-human antibodies added to the wells of the multi-well plate.

The detector reagent may be a single reagent or a series of reagents that collectively serve the detection purpose. In some examples, a detector reagent is a labeled binding partner specific for the analyte (such as, gold-conjugated Protein A for an antibody analyte, or gold-labeled anti-human Ab (such as goat-anti-human IgG and/or IgM) for a human antibody analyte, or gold-labeled oxidized cardiolipin for an anti-lipoidal antibody analyte). In other instances, a detector reagent collectively includes an unlabeled first binding partner specific for the analyte and a labeled second binding partner specific for the first binding partner and so forth. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

B. Flow-Through Device Construction and Design

A flow-through device involves a capture reagent (such as oxidized cardiolipin-attachment molecule complex) immobilized on a solid support, such as a membrane (such as, nitrocellulose, nylon, or PVDF). In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize nonspecific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as an anti-lipoidal antibody) can specifically bind to the immobilized capture reagent (such as oxidized cardiolipin-attachment molecule complex). Where detection of an analyte-capture reagent complex is desired, a detector reagent (such as labeled Protein A, labeled Protein G, labeled anti-human IgG, or labeled cardiolipin) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

C. Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; and 6,368,876; EP 0810436; and WO 92/12428; WO 94/01775; WO 95/16207.

Many lateral flow devices are one-step lateral flow assays in which a biological fluid is placed in a sample area on a bibulous strip (though, non-bibulous materials can be used, and rendered bibulous, e.g., by applying a surfactant to the material), and allowed to migrate along the strip until the liquid comes into contact with a specific binding partner that interacts with an analyte in the liquid. Once the analyte interacts with the binding partner, a signal (such as a fluorescent or otherwise visible dye) indicates that the interaction has occurred. Multiple discrete binding partners can be placed on the strip (for example in parallel lines) to detect multiple analytes in the liquid. The test strips can also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810.

Figure 6:
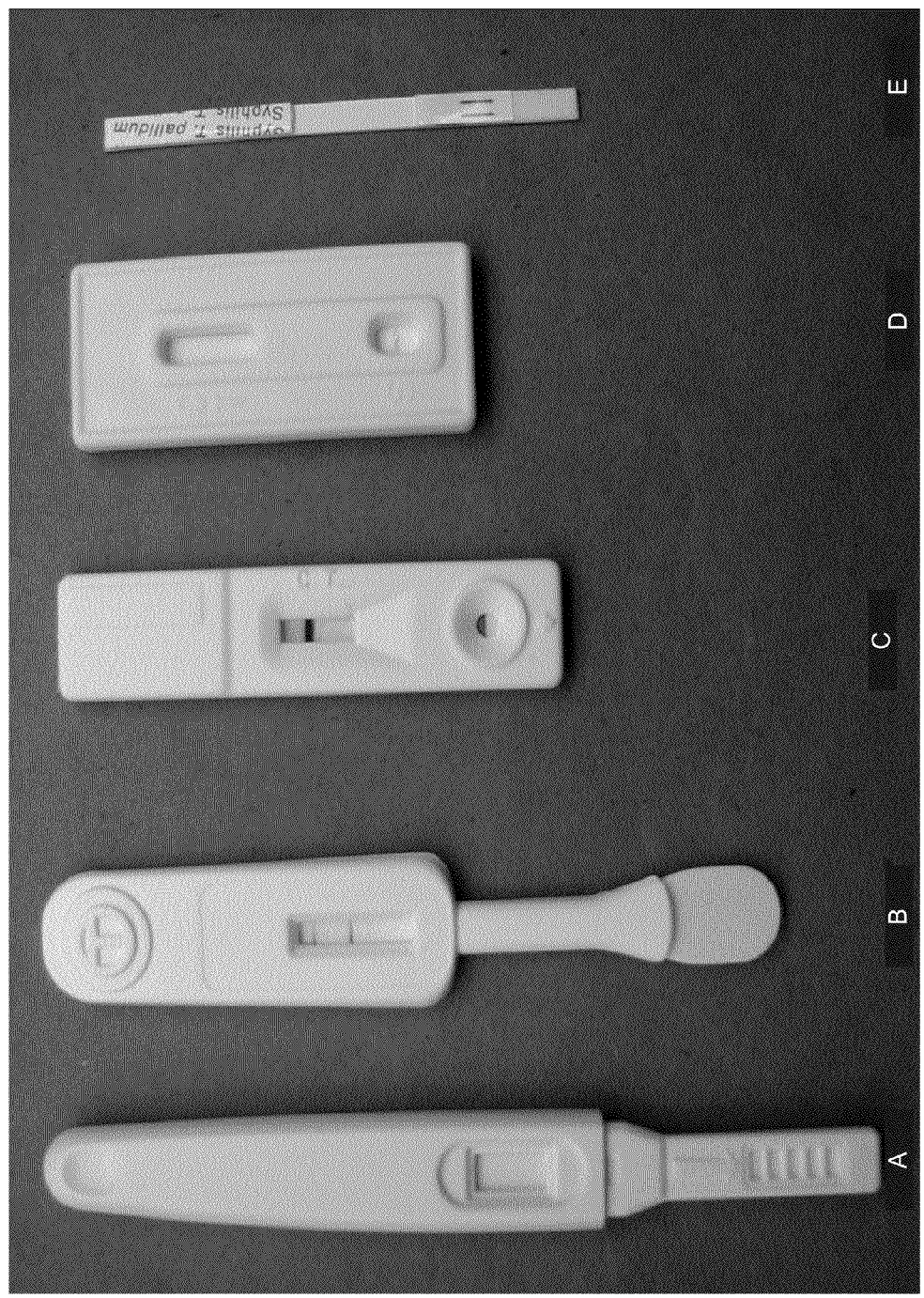
FIG. 6 shows a digital image of five different physical embodiments of lateral flow devices that could be used with the disclosed methods. The device embodiments shown in (A), (B) and (E) are configured so that each may be dipped into, or partially submerged in, the sample or a sample-containing solution. The device embodiments shown in (C) and (D) are configured so as to receive a volume of the sample (or a sample-containing solution) dropwise into a sample introduction port.

Lateral flow devices have a wide variety of physical formats. Any physical format that supports and/or houses the basic components of a lateral flow device in the proper function relationship is contemplated by this disclosure. FIG. 6 shows several examples of lateral flow devices. These examples demonstrate some of the physical embodiments that may be useful in the construction of a lateral flow device.

Figure 7:
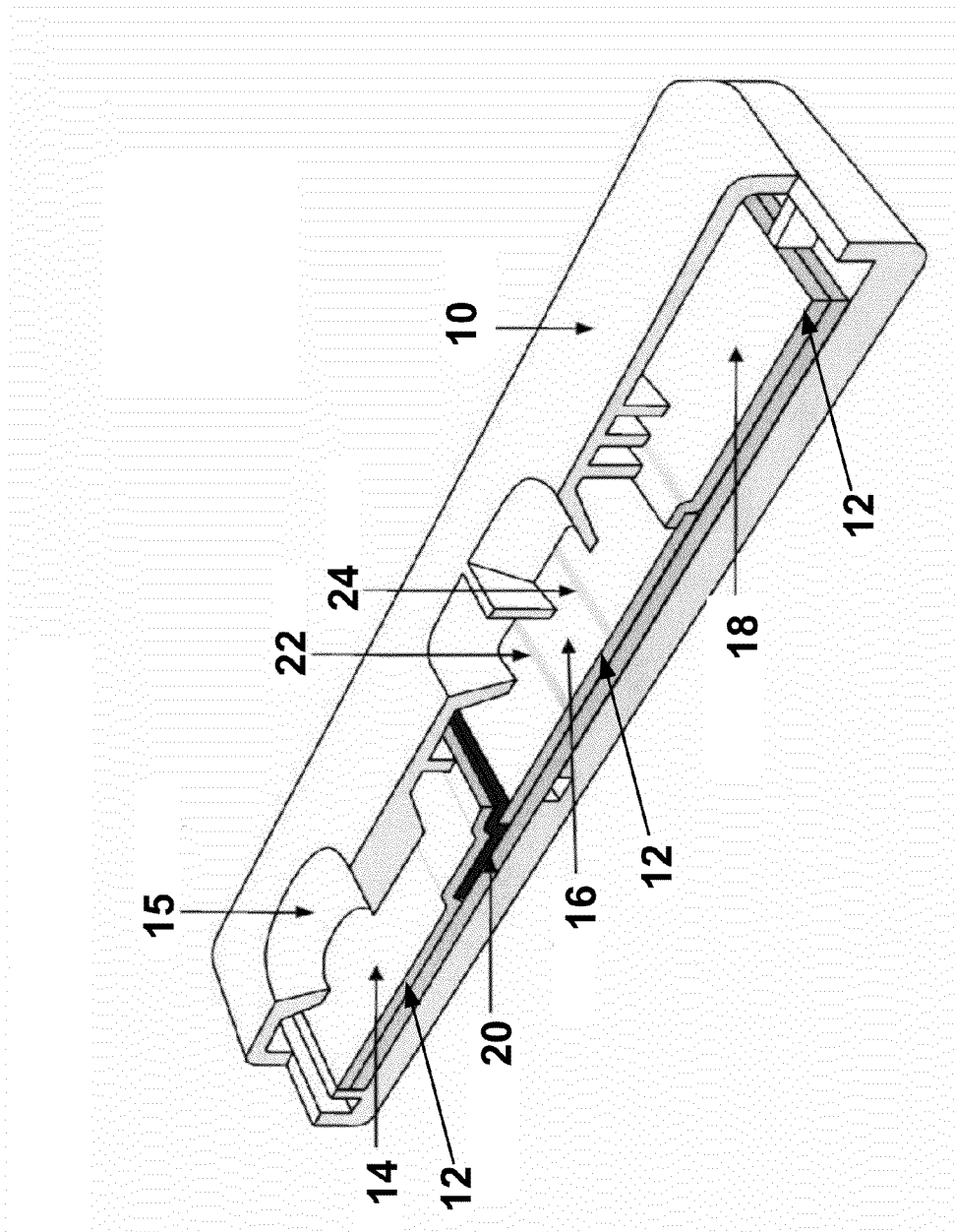
FIG. 7 is a perspective view of a physical embodiment of a lateral flow device, with a portion of the housing broken away to show the basic components of the device and their relationship to each other.

The basic components of a particular embodiment of a lateral flow device are illustrated in FIG. 7, which shows a particular embodiment in which an elongated housing 10 contains a bibulous lateral flow strip 12 that extends substantially the entire length of housing 10. Lateral flow strip 12 is divided into a proximal sample application pad 14 positioned below a sample introduction port 15, an intermediate test result membrane 16, and a distal absorbent pad 18. Flow strip 12 is interrupted by a conjugate pad 20 that contains labeled conjugate (such as gold-conjugated Protein A, gold-conjugated Protein G, gold-conjugated anti-human Ab). A flow path along strip 12 passes from proximal pad 14, through conjugate pad 20, into test result membrane 16, for eventual collection in absorbent pad 18. Selective binding agents (such as an anchor antibody-lipoidal antigen complex) are positioned on a proximal test line 22 in test result membrane 16. A control line 24 is provided in test result membrane 16 slightly distal to test line 22.

In operation of the particular embodiment of a lateral flow device illustrated in FIG. 7, a fluid sample containing an analyte of interest, such as an anti-lipoidal antibody, is applied to the sample pad 14 through the sample introduction port 15. In some examples, the sample may be applied to the sample introduction port 15 dropwise or, less preferably, by dipping the end of the device containing the sample introduction port 15 into the sample. In other examples where a sample is whole blood, an optional developer fluid is added to the blood sample to cause hemolysis of the red blood cells and, in some cases, to make an appropriate dilution of the whole blood sample. From the sample pad 14, the sample passes, for instance by capillary action, to the conjugate pad 20. In the conjugate pad 20, the analyte of interest may bind (or be bound by) a mobilized or mobilizable detector reagent. For example, an anti-lipoidal antibody analyte may bind to a labeled (e.g., gold-conjugated) Protein A or gold-conjugated cardiolipin detector reagent contained in the conjugate pad. The analyte complexed with the detector reagent may subsequently flow to the test result membrane 16 where the complex may further interact with an analyte-specific binding partner (such as oxidized cardiolipin-attachment molecule complex), which is immobilized at the proximal test line 22. In some examples, an anti-lipoidal antibody complexed with a detector reagent (such as, gold-conjugated cardiolipin, labeled (e.g., gold-conjugated) Protein A, labeled (e.g., gold-conjugated) Protein G, labeled (e.g., gold-conjugated) anti-human Ab) may further bind to unlabeled, oxidized cardiolipin-attachment molecule complexes immobilized at the proximal test line 22. The formation of the immunocomplex between anti-lipoidal antibody, labeled (e.g., gold-conjugated) detector reagent, and immobilized oxidized cardiolipin-attachment molecule complex can be detected by the appearance of a visible line at the proximal test line 22, which results from the accumulation of the label (e.g., gold) in the localized region of the proximal test line 22. The control line 24 may contain an immobilized, detector-reagent-specific binding partner, which can bind the detector reagent in the presence or absence of the analyte. Such binding at the control line 24 indicates proper performance of the test, even in the absence of the analyte of interest.

In another embodiment of a lateral flow device, there may be a second test line located parallel or perpendicular (or in any other spatial relationship) to test line 22 in test result membrane 16. The operation of this particular embodiment is similar to that described in the immediately preceding paragraph with the additional considerations that (i) a second detector reagent specific for a second analyte, such as an anti-*T. pallidum* antibody or *T. pallidum* organism or antigen, may also be contained in the conjugate pad, and (ii) the second test line will contain a second specific binding partner having affinity for a second analyte in the sample. For example, the second test line may contain immobilized treponemal antigens that will specifically bind anti-*T. pallidum* antibodies present in the sample or contain immobilized anti-*T. pallidum* antibodies that will specifically bind *T. pallidum* antigens or organisms present in the sample.

Some of the materials that may be useful for the components of a lateral flow device are shown in Table 1. However, one of skill in the art will recognize that the particular materials used in a particular lateral flow device will depend on a number of variables, including, for example, the analyte to be detected, the sample volume, the desired flow rate and others, and can routinely select the useful materials accordingly.

TABLE 1

| Component | Useful Material |
| --- | --- |
| Sample Pad | Glass fiber |
|  | Woven fibers |
|  | Screen |
|  | Non-woven fibers |
|  | Cellulosic filters |
|  | Paper |
| Conjugate Pad | Glass fiber |
|  | Polyester |
|  | Paper |
|  | Surface modified polypropylene |
| Membrane | Nitrocellulose (including pure nitrocellulose and modified nitrocellulose) |
|  | Nitrocellulose direct cast on polyester support |
|  | Polyvinylidene fluoride |
|  | Nylon |
| Absorbent Pad | Cellulosic filters |
|  | Paper |

1. Sample Pad

The sample pad (such as sample pad 14 in FIG. 7) is an optional component of a lateral flow device that initially receives the sample, and may serve to remove particulates from the sample. Among the various materials that may be used to construct a sample pad (see Table 1), a cellulose sample pad may be beneficial if a large bed volume (e.g., 250 µl/cm$^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose, nylon and PVDF), and considerations for applying a capture reagent to such membranes have been discussed previously.

3. Conjugate Pad

The conjugate pad (such as conjugate pad 20 in FIG. 7) serves to, among other things, hold a detector reagent. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application. In the particular disclosed embodiment, the detector reagent in conjugate pad 20 is gold-conjugated oxidized cardiolipin, labeled Protein A, labeled Protein G, or labeled anti-human IgG.

4. Absorbent Pad

The use of an absorbent pad 18 in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, see, for example, Table 1. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

D. Antigen-Coated Microtiter Plates

Other exemplary solid-surface-based immunoassays are various forms of immunoabsorbent assay, such as enzyme-linked immunoabsorbent assay (or ELISA). In one example, the solid support to which oxidized cardiolipin is attached is the well(s) of a multi-well plate. In some examples, the multi-well plate includes some wells with immobilized oxidized cardiolipin, and other wells with immobilized anti-treponemal antibodies or immobilized treponemal antigen. In some examples, the plate is composed of polystyrene, or other suitable material. The wells can be flat, C-shaped, or round bottom. In some examples the multi-well plate is a 6-, 12-, 24-, 48-, 96-, 384- or 1536-well plate.

The wells of the plates include an amine group or a protein(s) to which the oxidized cardiolipin can be attached.

These assays typically involve antigen (e.g., oxidized cardiolipin) applied in the wells of a multi-well plate. In this assay, a test sample (e.g., serum or blood) potentially containing an analyte of interest (e.g., anti-lipoidal antibody and in some examples also anti-treponemal antibody) is placed in the wells of multi-well plate that contain immobilized oxidized cardiolipin. The analyte specifically binds the immobilized oxidized cardiolipin; then, unbound materials are washed away leaving primarily the analyte-oxidized cardiolipicomplex bound to the plate. This complex can be detected in a variety of manners, as has been described in detail above. One advantage of the multi-well plate format is that multiple samples can be tested simultaneously (together with controls) each in one or more different wells of the same plate; thus, permitting high-throughput analysis of numerous samples.

E. Antigen Combinations

The immunoassays and/or immunoassay devices discussed herein (e.g., ELISA, dipstick, flow-through device or lateral flow device) can be, in some embodiments, formatted to detect multiple analytes by the addition of capture reagents specific for the other analytes of interest (e.g., treponemal antigens). For example, certain wells of a microtiter plate can include capture reagents specific for the other analytes of interest (such as wells containing oxidized cardiolipin, wells containing TAs or treponemal antibodies, or wells containing both oxidized cardiolipin and TAs or treponemal antibodies). Some immunoassay devices can include secondary, tertiary or more capture areas containing capture reagents specific for the other analytes of interest.

Particular embodiments involve immunoassay devices that concurrently detect anti-lipoidal antibody and treponemes or anti-treponemal antibodies in fluid samples (such as, human serum). Such combination devices further include a treponemal capture area involving (a) an immobilized treponemal antigen capable of being specifically bound by an anti-*T. pallidum* antibody, or (b) an immobilized anti-*T. pallidum* antibody that specifically binds a mobile treponemal antigen. As used herein, a "treponemal antigen" is an antigen containing at least one antigenic determinant that specifically binds anti-*T. pallidum* antibodies. Numerous treponemal antigens have been described; see, for example, U.S. Pat. Nos. 6,479,248; 6,248,331; 5,681,934; 5,578,456; 4,868,118; and 4,740,467. For instance, polypeptides of at least the following apparent molecular weights have been described as *T. pallidum* antigens: 16-20 kDa, 18 kDa, 18-23 kDa, 25 kDa, 35 kDa, 37 kDa, 37-46 kDa, 38 kDa, 39 kDa, 41 kDa, 43 kDa, 44 kDa, 46 kDa, 47 kDa, 58 kDa, 150 kDa; and 180 kDa (for more particular detail, see U.S. Pat. No. 4,846,118).

Treponemal antigens and anti-*T. pallidum* antibodies are polypeptides; thus, when used as capture reagents, these molecules can be directly adhered to a solid support (such as, polystyrene, nitrocellulose, nylon or PVDF, such as the wells of a multi-well plate). Nonetheless, it is contemplated that treponemal antigens or anti-*T. pallidum* antibodies can be immobilized (directly or indirectly) on a solid support by any available method.

A detector reagent can be used to detect the formation of a complex between a treponemal capture reagent and treponeme-specific analyte (such as, a treponeme, a treponemal antigen, or an anti-treponemal antibody). In some embodiments, a detector reagent (such as an anti-human Ab) can specifically detect a bound treponeme-specific analyte (e.g., a human anti-treponemal antibody) and a bound anti-lipoidal antibody analyte (e.g., a human anti-lipoidal antibody). In other instances, two separate detector reagents for specific detection of a bound treponeme-specific analyte (e.g., anti-treponemal antibody or treponemal antigen) or a bound anti-lipoidal antibody analyte are used.

The operation of an immunoassay device useful for performing concurrent treponemal and non-treponemal tests is substantially similar to devices described elsewhere in this specification.

Other immunoassay and immunoassay devices embodiments involve combinations of oxidized cardiolipin and other antigens specific for anti-lipoidal antibody; for example, immobilized lipoidal antigen comprising cardiolipin, lecithin and cholesterol Immobilization of lipoidal antigen is described in detail in PCT/US2006/024117, which is incorporated herein in its entirety by reference. In one example, a lipoidal antigen comprising cardiolipin (e.g., naturally occurring or synthetic cardiolipin), lecithin and cholesterol is contacted with a population of Fab fragments specific for the lipoidal antigen to provide a lipoidal antigen-Fab complex, which complex is readily attachable to a solid support in combination with oxidized cardiolipin-containing antigen.

VII. Kits

Disclosed herein are kits for use in detecting anti-lipoidal antibodies in a sample (such as, a biological sample). Such kits can also be used, for example, in the diagnosis of diseases in which the presence of anti-lipoidal antibodies is symptomatic of the disease (such as, syphilis or lupus). Certain embodiments of the disclosed kits are generally portable and provide a simple, rapid, and/or cost-effective way to detect anti-lipoidal antibodies and/or diagnose disease (such as syphilis).

Kits include one or more solid supports having immobilized thereon oxidized cardiolipin, such as multi-well plates, which can be present in a package or wrapper (such as, a sealed or sealable plastic, paper, or metallic wrapper), or other container. In some examples, kit components will be enclosed in a single packaging unit, such as a box or other container, which packaging unit may have compartments into which one or more components of the kit can be placed. In other examples, a kit includes one or more containers, for instance vials, tubes, and the like that can retain or contain, for example, one or more biological samples to be tested, positive and/or negative control samples or solutions (such as, a positive control serum containing anti-lipoidal or treponemal antibodies), diluents (such as, casein buffers, phosphate buffers, or saline buffers), detector reagents (e.g., labeled anti-human IgG or IgM), substrate reagents for visualization of detector reagent enzymes (such as, 5-bromo-4-chloro-3-indolyl phosphate, nitroblue tetrazolium in dimethyl formamide, TMB), stop solution (e.g., 2 N sulfuric acid), wash solutions (such as, Tris buffers, saline buffer, or distilled water), or combinations thereof.

In some examples the kit includes syringes, finger-prick devices, alcohol swabs, gauze squares, cotton balls, bandages, latex gloves, incubation trays with variable numbers of troughs, adhesive plate sealers, data reporting sheets, which may be useful for handling, collecting and/or processing a biological sample. Kits may also optionally contain implements useful for introducing samples into a sample chamber of an immunoassay device, including, for example, droppers, Dispo-pipettes, capillary tubes, rubber bulbs (e.g., for capillary tubes), and the like. Still other kit embodiments may include disposal means for discarding a used immunoassay device and/or other items used with the device (such as patient samples, etc.). Such disposal means can include, containers that are capable of containing leakage from discarded materials, such as plastic, metal or other impermeable bags, boxes or containers.

In some examples, a kit includes instructions for the use of an immunoassay device or oxidized cardiolipin-coated plate. The instructions may provide direction on how to apply sample to the test device or plate, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify analyte (e.g., non-treponemal IgG or IgM) using the test device, such as a standard curve relating intensity of signal or number of signal lines to an amount of analyte therefore present in the sample.

In one specific example, a kit includes one or more ELISA plates with wells containing oxidized cardiolipin, a negative control (such as human serum non-reactive to cardiolipin antigen), a positive control (such as human serum containing antibody to cardiolipin), a sample diluent (such as casein buffer with phosphate buffered saline and detergent with preservative), a wash solution (such as phosphate buffered saline solution with detergent and preservative), labeled anti-human IgG, labeled anti-human IgM, a buffer to dilute antibodies, and optionally a solution to detect the label (such as TMB-substrate solution), and optionally a stop solution (such as 2N sulfuric acid).

VII. Methods of Detecting Cardiolipin Antibodies

Disclosed herein are methods of using the disclosed solid supports to detect non-treponemal antibodies in a sample. Such methods in some examples are automated. The disclosed methods can be used for screening, for example to determine if a subject has syphilis or has been infected with *T. palladium*. In some examples, such a method can replace traditional VDRL and RPR assays. In some examples, this method is used to screen a large number of samples simultaneously or contemporaneously. The results can be objective by setting a numerical cut-off value for positive or negative samples. Such methods can be used as a confirmatory test, to diagnose a recent syphilis infection, to monitor efficacy of syphilis treatment, to determine the stage of syphilis infection, or combinations thereof.

In some examples, the method detects of an anti-lipoidal antibody/oxidized complex quantitatively or qualitatively. Thus, in some examples, the method includes detecting non-treponemal (e.g., cardiolipin) IgA, IgG and/or IgM antibodies, qualitatively or quantitatively. In some examples, the methods can be used to quantitatively determine an amount of anti-lipoidal IgG antibody and/or anti-lipoidal IgM antibody in a sample.

Thus, in some examples, such methods permit diagnosis of syphilis. For example detection of an anti-lipoidal antibody/oxidized complex indicates that the patient has been infected with *T. palladium*, and a diagnosis of syphilis can be made.

In some examples, the methods permit monitoring the efficacy of syphilis treatment. In some examples, detection of reduced amounts of the anti-lipoidal antibody/oxidized complex (such as a reduction in anti-lipoidal IgG and/or IgM antibody) following a syphilis treatment indicates that the treatment is effective (such as a reduction of at least 10%, at least 20%, at least 50%, at least 75% or at least 90% relative to an amount prior to starting the therapy or shortly following the start of therapy). In other examples, detection of unchanged or increased amounts of the anti-lipoidal antibody/oxidized complex (such as unchanged or increased amounts of anti-lipoidal IgG and/or IgM antibody) following a syphilis treatment indicates that the treatment is not effective (such as an increase of at least 10%, at least 20%, at least 50%, at least 75% or at least 90% relative to an amount prior to starting the therapy or shortly following the start of therapy).

In some examples, the methods permit for a determination of the stage of syphilis infection (such as monitoring the progression of the disease or the efficacy of treatment) by measuring separately the nontreponemal IgM and IgG antibody content in the sera of a patient with syphilis by means of the optical density values derived by the EIA test). For example, detection of an anti-lipoidal IgM antibody/oxidized complex can indicate recent syphilis infection.

As shown in FIG. 11, a sample that may contain cardiolipin is added to a multi-well plate (or other solid substrate) containing the immobilized oxidized/activated cardiolipin. The sample can be used directly, or for example diluted before use. If non-treponemal (e.g., cardiolipin) antibodies are present in the sample, it will bind to the cardiolipin present in the wells, forming a complex between the oxidized cardiolipin and the cardiolipin antibodies. The plate can be washed one or more times to remove unbound materials.

Bound cardiolipin antibodies can then be detected. In one example, labeled anti-human antibodies, such as anti-human IgG and/or anti-human IgM (such as goat anti-human (AHG) antibodies) are added to the wells of the plate to detect the complexes. Although goat-anti-human antibodies are shown, one skilled in the art will appreciate that other anti-human antibodies can be used, such as rabbit, mouse, or rat antibodies. The plate can be washed one or more times to remove unbound anti-human antibodies. In some examples, the label on the anti-human antibodies is HRP, and the reaction is stopped with a stopping solution. The HRP can then be reacted to permit its detection at 450 nm. However, one skilled in the art will appreciate that other labels besides HRP can be used.

Labeled anti-human antibodies are commercially available, for example from Thermo Scientific Pierce Antibodies (goat anti-human IgM-HRP catalog #31415 and goat anti-human IgG-HRP catalog #31414), Abcam (mouse anti-human IgM-HRP catalog #ab99737 and #ab99744 and mouse anti-human IgG-HRP catalog #ab99765 and mouse anti-human IgG biotin catalog #ab99766), and Neoclone (mouse anti-human IgM-HRP catalog #N0027 and mouse anti-human IgG-HRP catalog #N0025).

The anti-cardiolipin IgG and IgM antibodies can detected together, or separately. For example, if IgG and IgM are to be detected together, labeled anti-human IgG and labeled anti-human IgM antibodies can be added together to well, and the labels detected. in contrast, if IgG and IgM are to be detected separately, for example to determine an amount of cardiolipin IgG and/or IgM, anti-human IgG and labeled anti-human IgM antibodies can be added to different wells of a single multi-well plate (or to separate plates), and the labels detected.

In another example, bound cardiolipin antibodies are detected using a double-antigen sandwich assay. For example, the complex between the oxidized cardiolipin and the cardiolipin antibodies can be detected by using labeled cardiolipin. Labeled cardiolipin, such as biotinylated cardiolipin, can be added to the wells of the plate to detect the complexes. The plate can be washed one or more times to remove unbound labeled cardiolipin. In some examples, the label on the labeled cardiolipin is biotin, and the method further includes adding to the wells of the plate labeled streptavidin. The plate can be washed one or more times to remove unbound labeled streptavidin. In one example, the label on the streptavidin is HRP. The reaction can then be stopped with a stopping solution. The HRP can then be reacted to permit its detection at 450 nm. However, one skilled in the art will appreciate that other labels besides HRP can be used.

In some examples, the method includes detecting non-treponemal (e.g., cardiolipin) antibodies (e.g., IgG and/or IgM), for example quantitatively. In some examples, the detected OD value represents the concentration of antibody present, which can eliminate the need to determine the titer of antibody. For example, the method can include detecting cardiolipin IgM antibodies quantitatively. Such a method can be used as a confirmatory test, for example to confirm the results of a qualitative assay. Detection of cardiolipin IgM antibodies permits detection or diagnosis of a recent *T. palladium* infection, and can be used to monitor the efficacy of treatment. For example, levels of cardiolipin IgM antibodies in some examples decrease following treatment, such as a decrease of at least 25%, at least 50%, at least 75%, at least 90%, or at least 95% as compared to an amount prior to treatment. Detection of cardiolipin IgM antibodies can also be used to detect or diagnose congenital syphilis.

In some examples, the method includes detecting cardiolipin IgG antibodies quantitatively. Such a method can be used as a confirmatory test, for example to confirm the results of a qualitative assay. Detection of cardiolipin IgG antibodies can be used to monitor the efficacy of treatment. For examples, levels of IgG antibodies in some examples decrease following treatment, such as a decrease of at least 25%, at least 50%, at least 75%, at least 90%, or at least 95% as compared to an amount prior to treatment. Detection of IgG antibodies can also be used to determine the stages of syphilis.

Figure 12:
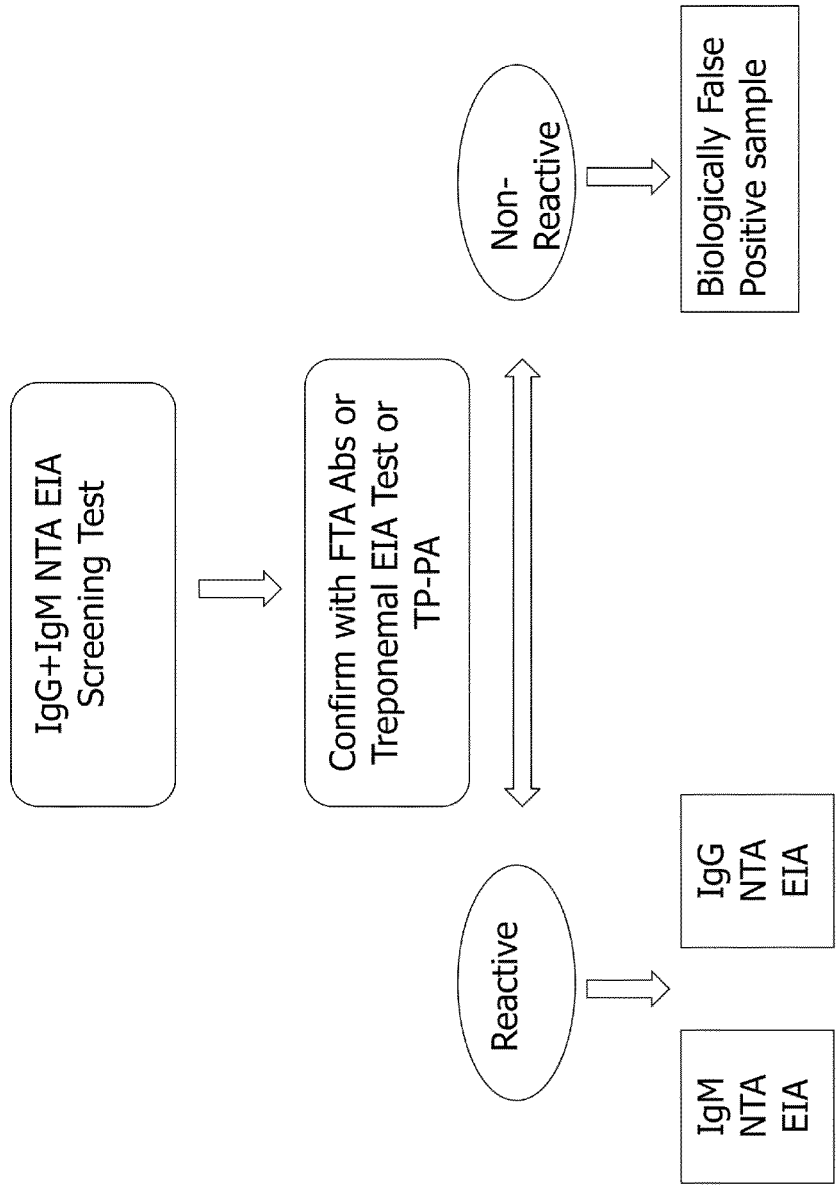
FIG. 12 is a flow diagram showing an exemplary algorithm for analyzing a sample for non-treponemal antigens (NTAs) using the multi-well ELISA plates herein disclosed.

As shown in FIG. 12, the disclosed methods can be used to analyze a sample for the presence of non-treponemal antibodies, such as cardiolipin IgG and IgM antibodies. For example, the method can include analyzing the sample for the presence of non-treponemal (NTA) antibodies. The method can further include analyzing the sample for the presence of treponemal (TA) antibodies. If the sample is positive for NTA and TA antibodies, the sample can be further analyzed to determine if the NTA antibodies are cardiolipin IgG and/or IgM antibodies (for example quantitatively).

The following examples are provided to illustrate certain particular features and/or embodiments. These examples should not be construed to limit the disclosure to the particular features or embodiments described.

EXAMPLE 1

Oxidation of Cardiolipin

This example describes the oxidation of double bonds in the unsaturated fatty acids of unmodified cardiolipin to carboxyl groups.

Approximately 100 mg of lyophilized cardiolipin (Avanti Polar Lipids (Alabaster, Ala.)) was dissolved in 2 mls of t-butanol and placed in a vial under an argon atmosphere. Sixty (60) mg of sodium m-periodate ($NaIO_4$) was dissolved in 600 μl of distilled water and added dropwise to the cardiolipin suspension with constant stirring. Promptly thereafter, 8 mg of potassium permanganate ($KMnO_4$), dissolved in 400 μl of distilled water, was added dropwise to the $NaIO_4$ reaction mixture with constant stirring. The mixture changed color (FIG. 1B) and was allowed to mix for 24-48 hours at room temperature.

The degree of cardiolipin oxidation was qualitatively determined by thin layer chromatography (TLC). Approximately 10 ml of a chloroform:methanol:ammonium hydroxide solution (61.9:30.9:7.1 by volume) was placed in a 100 ml beaker. A folded filter paper was placed inside the beaker and was allowed to become saturated with the solvent.

One (1) μl of the $NaIO_4/KMnO_4$ reaction mixture and 1 μl of a 20 mg/ml cardiolipin t-butanol (control) solution were placed 1 cm from the end of a 7.5 cm×2.5 cm strip of TLC silica gel. The strip was placed against the filter paper in the beaker, and the solvent was allowed to migrate to the top of the strip.

After removing the strip from the solvent, it was allowed to evaporate to dryness. Thereafter, the strip was wetted by brief submersion in 50 ml of 5% ethanol containing at least 10 ml of molybdenum blue (Spray Reagent; Alltech; Part No. 18213). The strip was heat dried with the aid of a hair dryer to develop the stain.

Figure 1:
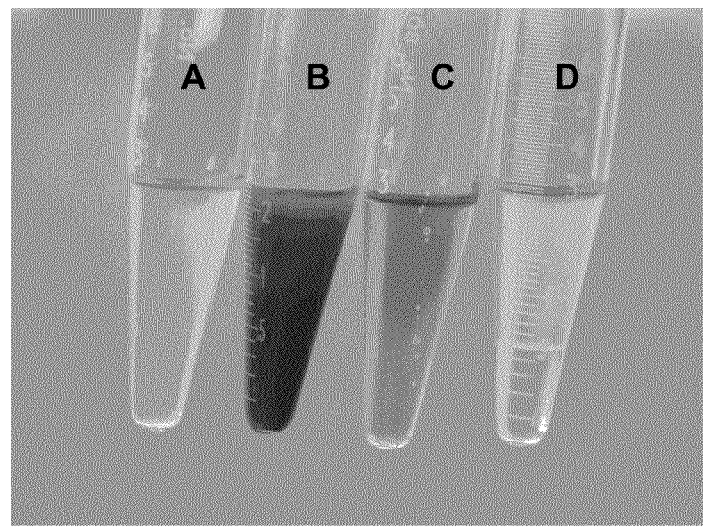
FIG. 1 shows digital images of steps in the oxidation of cardiolipin. (A) Unmodified cardiolipin in t-butanol; (B) cardiolipin reaction mixture after the addition of sodium m-periodate and potassium permanganate; (C) cardiolipin reaction mixture after the addition of sodium bisulfite; and (D) two-phase solution obtained after centrifugation of mixture (C), wherein several oxidized forms of cardiolipin are predominantly found in the upper, t-butanol phase.

Upon completion of cardiolipin oxidation, the $NaIO_4/KMnO_4$ reaction mixture reaction was stopped by adding 80 mg of sodium bisulfate in 200 μl in distilled water with constant stirring. The colored mixture then turned colorless (compare FIG. 1B and FIG. 1C). The stopped reaction mixture was centrifuged at 1000×g for 5 minutes. After centrifugation there were two visible phases (FIG. 1D).

Optionally, the supernatant t-butanol phase was placed in an evaporation round flask and dried under vacuum. Alternatively, the t-butanol phase may be dialyzed against 10 mM phosphate buffer, pH 8.0, or other buffer, to replace the alcohol solvent with a solution that is suitable for the next-intended use of the oxidized cardiolipin contained therein, for example, for use in immunochromatographic assays, or, for example, for conjugation to an attachment molecule.

Figure 2:
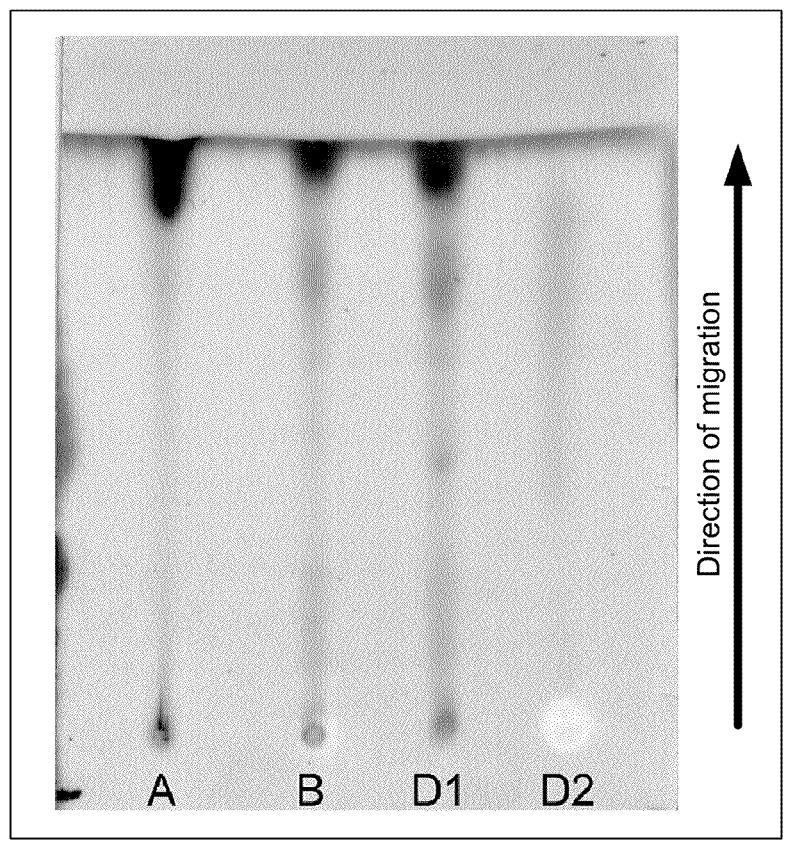
FIG. 2 shows digital images of thin-layer chromatographs of cardiolipin preparations. (A) Unmodified cardiolipin in t-butanol (see FIG. 1A); (B) an oxidized cardiolipin preparation; (D1) the upper, t-butanol phase following a cardiolipin oxidation reaction (see FIG. 1D); and (D2) the lower, aqueous phase following a cardiolipin oxidation reaction (see FIG. 1D). The direction of migration of each sample is shown by an arrow.

As shown in FIG. 2, unmodified cardiolipin migrates primarily to the top of a TLC strip, as indicated in lane A by the dark spot furthest from the point of origin. Cardiolipin naturally comprises a heterogeneous population of molecules, as described in Section IV. Because linoic acid makes up approximately 90% of the fatty acid side chains in cardiolipin, predominantly linoic-acid-containing cardiolipin molecules (and closely related cardiolipin forms) are likely represented by the dark spot in FIG. 2, lane A. Lesser represented cardiolipin forms likely have differing mobilities and may account for the slight smear observed in lane A in the direction of migration.

As described previously, oxidation of cardiolipin oxidizes alkenes, cleaves the fatty acid side chains, and introduces carboxyl groups into one or more of the fatty acid side chains. Carboxyl groups present in oxidized cardiolipin interact more strongly with the silica substrate of a TLC strip, which retards the migration of oxidized cardiolipin forms along the strip. Hence, in oxidized cardiolipin preparations (see FIG. 2, lanes B and D1), the smear in the direction of migration becomes more pronounced (compare lane A with lanes B and D1). In addition, oxidative cleavage of the fatty acid side chains produces alkyl carboxylates, which have little mobility on a TLC strip under these conditions. As shown in FIG. 2, lanes B and D2, the carboxylates are thought to be represented by a white spot (due to dye exclusion) coextensive with the point of origin. Following cardiolipin oxidation as described in this example, oxidized forms of cardiolipin were found predominantly in the t-butanol phase (shown in FIG. 2, lane D1), while alkyl carboxylates were found predominantly in the aqueous phase (see FIG. 2, lane D2).

As judged by reactivity with syphilitic serum (see, e.g., Example 4), the upper t-butanol phase ("alcohol phase") (see FIG. 2, lane D1) contained oxidized cardiolipin species, while the lower aqueous phase (see FIG. 2, lane D2) was believed to contain mostly a mixture of malonic acid and caproic acid byproducts based on TLC results.

EXAMPLE 2

Activation of Oxidized Cardiolipin and Conjugation with Attachment Molecules This example demonstrates several methods of conjugating oxidized cardiolipin with BSA or KLH using EDC and NHS.

A. Method One

After complete evaporation of the t-butanol phase described in Example 1, the dry oxidized cardiolipin preparation was suspended in 2 ml of N,N-formamide to a concentration of approximately 25 mg/ml. Ten (10) mg of EDC and 10 mg of NHS were dissolved in 1 ml of distilled water. The EDC/NHS solution was then added to the formamide solution containing oxidized cardiolipin. The resultant mixture was stirred for 1 hour at room temperature. As one of skill in the art will recognize, EDC and NHS will convert carboxyl groups in oxidized cardiolipin to amine-reactive NHS esters.

Up to a 40-fold molar excess of BSA or KLH was added to the EDC/NHS/oxidized cardiolipin mixture, and the mixture was stirred for one hour at room temperature. Preferably, about 1 ml of a 5 mg/ml KLH or BSA solution was added. As the amount of BSA or KLH in the reaction mixture is increased (e.g., to 10 mg/ml or greater), the more likely it becomes that the protein component will crosslink to itself, which will cause a precipitate to appear. In this event, it may be necessary to separate the precipitate by centrifugation and discard it.

The reaction mixture was clarified, as needed, and then dialyzed against two, one-liter changes of 10 mM phosphate buffer, pH. 8.0. The preparation was concentrated by membrane filtration (Centricon filter; Millipore) to approximately 10 mg/ml oxidized cardiolipin. The oxidized cardiolipin solution may be stored at 2-8° C. or –20° C. until needed.

B. Method Two

After complete evaporation of the t-butanol phase, as described in Example 1, the dry oxidized cardiolipin preparation was suspended in 2 ml of N,N-formamide to a concentration of approximately 25 mg/ml. This formamide mixture was then dialyzed against two, one-liter changes of 10 mM phosphate buffer, pH. 8.0 prior to the addition of the EDC/NHS solution, as described in Method One in this example. The steps following addition of the EDC/NHS solution are the same as those described in Method One.

C. Method Three

An oxidized cardiolipin preparation was prepared by dialyzing the t-butanol phase described in Example 1 against 10 mM phosphate buffer, pH 8.0, followed by lyophilization to dryness. For use in a subsequent reaction, the lyophilized oxidized cardiolipin was reconstituted in water to approximately 25 mg/ml. Then, 10 mg of EDC and 10 mg of NHS dissolved in 1 ml of distilled water was added to the oxidized cardiolipin solution with stirring for 1 hour at room temperature. The steps following addition of the EDC/NHS solution are the same as those described in Method One.

EXAMPLE 3

Biotinylation of Oxidized Cardiolipin

This example describes the biotinylation of oxidized cardiolipin.

Ten (10) mg of oxidized cardiolipin (see Example 1) was dissolved in one ml of 100 mM N-morpholinoethane sulfonic acid (MES). One hundred (100) µl of 20 mg/ml biotin-PEO-amine was added to the oxidized cardiolipin solution. Immediately thereafter, 25 µl of a freshly prepared 1 mg/ml EDC solution was added to the biotin/cardiolipin mixture, and the solution was mixed for 2 hours at room temperature. The reaction mixture was then dialyzed against two changes of 10 mM phosphate buffer, pH 8.0. The biotinylated product was concentrated by lyophilization and can thereafter be reconstituted with distilled water to a desired concentration, for example, 10 mg/ml.

EXAMPLE 4

Antigenicity of Cardiolipin Preparations

This example demonstrates that oxidized cardiolipin as prepared in Example 1 retains antigenicity when tested against syphilitic serum using two immunoassays.

A. RPR Inhibition Test

One hundred (100) µl of syphilitic serum (lot 50 L) was mixed with 50 µl of the oxidized cardiolipin-BSA or -KLH preparations (approximately 2.5-5 mg/ml) described in Table 2. If an oxidized cardiolipin preparation retains antigenicity, anti-lipoidal antibodies present in the serum will specifically bind to the oxidized cardiolipin preparation, which will act to reduce the number of available anti-lipoidal antibody binding sites. In other words, the serum will be "stripped" of some or all of the anti-lipoidal antibody binding sites. Serum that has been stripped of anti-lipoidal antibody binding sites will be less reactive when tested in the conventional RPR test.

TABLE 2

Oxidized Cardiolipin Preparations

| Cardiolipin Prep. No. | Hrs. Oxidation | Conjugate Type | Method of Preparation (see Example 2) |
| --- | --- | --- | --- |
| 1 | 48 | Oxidized cardiolipin-BSA | Method One |
| 2 | | Duplicate of Preparation 1 | |
| 3 | 48 | Oxidized cardiolipin-KLH | Method One |
| 4 | | Duplicate of Preparation 3 | |
| 5 | 24 | Oxidized cardiolipin-BSA | Method Three |
| 6 | 24 | Oxidized cardiolipin-KLH | Method Three |
| 7 | 24 | Oxidized cardiolipin-BSA | Method One |
| 8 | | Duplicate of Preparation 7. | |
| 9 | 24 | Oxidized cardiolipin-KLH | Method One |
| 10 | | Duplicate of Preparation 9 | |
| 11 | 24 | Oxidized cardiolipin-BSA conjugate | Method Two |
| 12 | 24 | Oxidized cardiolipin-KLH | Method Two |

The stripped (and control) serum was tested in an RPR test in accordance with Chapter 10 of the *Manual of Tests for Syphilis*, 9th Edition, Washington, D.C.: American Public Health Association, 1998.

As shown in Table 3, control syphilitic serum, to which 50 µl of 5 mg/ml unconjugated BSA was added, reacted with the RPR test antigen at a 1:8 serum dilution. Incubation of the syphilitic serum with each of the cardiolipin preparations 1-12 (described in Table 2) inhibited the reactivity of the serum with the RPR test antigen by at least two-fold. This result indicates that each of the cardiolipin preparations reacted to some extent with the anti-lipoidal antibodies present in the test syphilitic serum, and thereby inhibited the stripped serum from reacting with the RPT test antigen. For example, preincubation of the syphilitic test serum with cardiolipin preparations 2, 11, and 12 completely inhibited the reactivity of the serum in the RPR test.

TABLE 3

RPR Inhibition Test Results

| Cardiolipin Preparation* Used for Serum Preincubation | Serum (Lot 50L) Dilution | | | | | |
|---|---|---|---|---|---|---|
| | 1:1 | 1:2 | 1:4 | 1:8 | 1:16 | 1:32 |
| None (i.e., Control) | R | R | R$_{(-)}$ | Rm | N | N |
| Preparation 1 | Rm | N | N | N | N | N |
| Preparation 2 | N | N | N | N | N | N |
| Preparation 3 | Rm$_{(-)}$ | N | N | N | N | N |
| Preparation 4 | Rm$_{(-)}$ | N | N | N | N | N |
| Preparation 5 | Rm$_{(-)}$ | N | N | N | N | N |
| Preparation 6 | Rm$_{(-)}$ | N | N | N | N | N |
| Preparation 7 | Rm$_{(-)}$ | N | N | N | N | N |
| Preparation 8 | Rm | Rm$_{(-)}$ | N | N | N | N |
| Preparation 9 | Rm | Rm$_{(-)}$ | N | N | N | N |
| Preparation 10 | Rm | Rm$_{(-)}$ | N | N | N | N |
| Preparation 11 | N | N | N | N | N | N |
| Preparation 12 | N | N | N | N | N | N |

Figure 5:
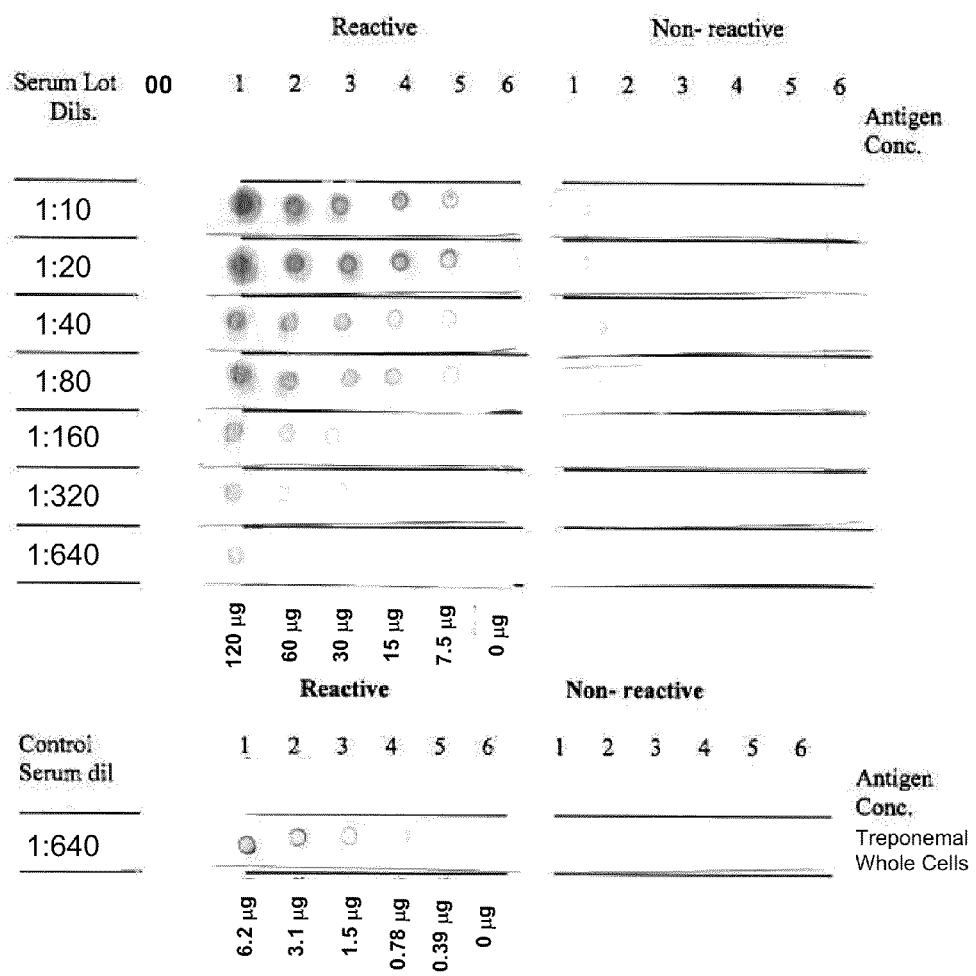
FIG. 5 shows a digital image of a dot blot assay used to determine the antigenicity of an oxidized cardiolipin-BSA conjugate ("Preparation 5" in Table 2).

*See Table 2 for description of cardiolipin preparations
R = strong positive reaction
R$_{(-)}$ = positive reaction
Rm = weak reaction
Rm$_{(-)}$ = very weak reaction
N = negative reaction B. Immuno-Blot Test Dot blot assays were performed using the Immun-Blot® Assay Kit (BioRad) with a goat anti-human IgG alkaline-phosphatase conjugate in accordance with the manufacturer's instructions. As shown in FIG. 5, oxidized cardiolipin-BSA preparation 5 (see Table 2) reacted with syphilitic serum (Lot 00) over a wide range of antigen (7.5-120 µg) and antibody (1:10-1:640 dilution) concentrations. In comparison, preparation 5 did not react at all with normal, human serum (i.e., non-syphilitic serum) over the same ranges of antigen and antibody concentrations.

FIG. 5 also shows that serum Lot 00 (1:640 dilution) reacts with a whole cell *T. pallidum* preparation, which confirms that the serum donor had been infected with *T. pallidum*.

EXAMPLE 5

Preparation of Oxidized Cardiolipin Gold Conjugate

This example demonstrates the conjugation of oxidized cardiolipin-BSA or -KLH with colloidal gold, and determination of useful conditions for the preparation of such gold conjugates. This colloidal gold preparation can be used as the conjugate in a lateral flow strip, such as the lateral flow strip described in association with FIG. 7.

A. Determination of a Useful pH for Oxidized Cardiolipin/ Colloidal Gold Conjugation Reaction Approximately 25 ml of 10 mM phosphate buffer was placed in a 50-ml beaker, and adjusted to pH 5.0 with 0.2 M phosphoric acid. Two 0.5-ml aliquots of the buffer at pH 5.0 were transferred to two 12×75 mm test tubes, one labeled "test" and the other labeled "control." Then, the pH of the phosphate buffer remaining in the beaker was sequentially adjusted to 5.5, 6.0, 6.5, 7.0, 7.5, 8.0, 8.5, 9.0, 9.5, and 10.0 using 0.2 M potassium carbonate. At each pH, two 0.5-ml aliquots were transferred to a "test" and "control" test tube as described for the pH 5.0 sample.

Six (6) µL of a 5 mg/ml cardiolipin-BSA preparation or a 5 mg/ml cardiolipin-KLH preparation (30 µg), prepared as described in Example 2, was added to each of the "test" and "control" tubes, and mixed well.

Approximately 25 ml of 40-nm colloidal gold (1% solution) (British Biocell International, London, England) was placed in a separate 50-ml beaker, and a series of "control" and "test" colloidal gold samples at pH 5.0, 5.5, 6.0, 6.5, 7.0, 7.5, 8.0, 8.5, 9.0, 9.5, and 10.0 were produced as described above.

One (1) ml of colloidal gold at each pH was added to the "test" and "control" cardiolipin solutions having the corresponding pH. The gold/cardiolipin solutions were mixed well, and incubated for 20 minutes at room temperature. Then, 200 µL 2 M NaCl was added to the set of tubes labeled "test" and 200 µL of distilled water was added to the set of tubes labeled "control." The contents of both sets of tubes were allowed to incubate for 30 minutes at room temperature.

The optical density at 580 nm (OD$_{580}$) of each "test" sample was read against the corresponding "control" sample. The pH of the sample with the lowest OD$_{580}$ was determined to be a favorable pH for formation of a gold conjugate of the oxidized cardiolipin-BSA or -KLH preparation.

Colloidal gold particles have a negatively charged surface due to the layer of negative ions adsorbed onto the gold particle surface during the manufacturing process. Proteins, such as BSA or KLH in oxidized cardiolipin-BSA or -KLH preparations, will be attracted to negatively charged gold particles through ionic, hydrophobic, and dative interactions. These interactions underlie the formation of colloidal gold-protein conjugates. At the pI of a protein conjugated to a gold particle (i.e., the pH where the protein has a net zero charge), the conjugate will be the most stable.

The addition of NaCl to unconjugated colloidal gold particles will disrupt the layer of negatively charged ions adsorbed to the gold's surface. As a result, the gold particle will dissociate and ultimately release gold ions (i.e., Au$^+$) into solution. The free gold ions may be measured at OD$_{580}$. In contrast, a protein-gold conjugate (e.g., oxidized cardiolipin-BSA-gold conjugate or oxidized cardiolipin-KLH-gold conjugate) is resistant to disruption by NaCl at the pI of the protein component of the conjugate (e.g., the pI of oxidized cardiolipin-BSA or the pI of oxidized cardiolipin-KLH). Hence, in this example, the pH of the sample with the lowest OD$_{580}$ is selected.

Because the molar ratio of cardiolipin to attachment molecule in each oxidized cardiolipin-attachment molecule (e.g., oxidized cardiolipin-BSA or oxidized cardiolipin-KLH) preparation may differ, the pI of each such preparation may also differ. Thus, it is beneficial to determine the useful pH, as described in this example, for each oxidized cardiolipin-attachment molecule preparation made.

B. Determination of a Useful Cardiolipin-BSA or Cardiolipin-KLH Concentration for a Colloidal Gold Conjugation Reaction One hundred (100) µl of distilled water was added to each in a series of eleven 12×75 mm test tubes. Then, 1 µl, 2 µl, 5 µl, 7 µl, 10 µl, 15 µl, 25 µl, 50 µl, 75 µl or 100 µl of a 1 mg/ml solution of either cardiolipin-BSA or cardiolipin-KLH was added to a corresponding tube in the series. The eleventh tube in the series served as a control. Each tube was mixed well, and allowed to incubate at room temperature for 5 minutes. At this point, the solution in each tube was red in color. Five hundred (500) µl of a 10% NaCl solution was then added to each tube with shaking, and the tubes were again incubated at room temperature for 5 minutes. The color of the solution of each tube was observed by eye with some turning from red to blue after the addition of NaCl. The minimum amount of cardiolipin-attachment molecule useful for stabilizing the gold conjugate was determined to be the lowest concentration of cardiolipin-attachment molecule in a blue-colored solution after NaCl addition.

Higher concentrations of oxidized cardiolipin-attachment molecule complex, though useful, are less preferred because excess oxidized cardiolipin-attachment molecule complexes may form weaker associations with the gold particles, for example, by layering upon a layer of cardiolipin-attachment molecule complexes that previously associated with the gold particles.

Similarly, lower concentrations of oxidized cardiolipin-attachment molecule complex may be useful, but are less preferred because unconjugated gold particles may provide background "noise" in other applications of the gold-conjugated cardiolipin-attachment complexes. Alternatively, unconjugated gold particles may be separated from gold-conjugated cardiolipin-attachment molecule complexes using methods commonly known in the art, such as centrifugation or filtration.

C. Cardiolipin-BSA or Cardiolipin-KLH Gold-Conjugate Minipreps.

For a particular oxidized cardiolipin-BSA or -KLH preparation, determine a useful pH and a useful oxidized cardiolipin-BSA or oxidized cardiolipin-KLH concentration as described above. If the useful pH is pH 8.0 or higher, then add 5 ml of 10 mM borate buffer to the amount of lyophilized oxidized cardiolipin-attachment molecule complex necessary to achieve the useful concentration; then, adjust the pH to the useful pH. If the useful pH is pH 8.0 or lower, add 5 ml of 10 mM phosphate buffer to the amount of lyophilized oxidized cardiolipin-attachment molecule complex necessary to achieve the useful concentration; then, adjust the pH to the useful pH. Next, add 10 ml of 40-nm colloidal gold (1% solution adjusted to the useful pH), and mix well. Incubate the mixture for 20 minutes at room temperature. Then, add 1.6 ml of 10% BSA to a final concentration of 1% BSA, and incubate for an additional 20 minutes at room temperature. Centrifuge the reaction mixture at 6500×g for 10 minutes, and remove the supernatant. Resuspend the pellet in 0.5 ml of resuspension buffer (150 mM NaCl, 20 mM Trizma base, 10% sucrose, 5% Trehalose, 0.1% BSA, 0.05% sodium azide). The resuspended pellet containing gold conjugated oxidized cardiolipin-BSA or -KLH may be used for a variety of purposes, including without limitation as a detector reagent for anti-lipoidal antibodies in a lateral flow device.

EXAMPLE 6

Attachment of Cardiolipin-Attachment Molecule Complexes to Nitrocellulose

This example describes a representative method for attaching cardiolipin-protein complexes to a solid surface, in this case, nitrocellulose.

For a particular oxidized cardiolipin-BSA or -KLH preparation, determine a useful pH as described previously. Resuspend lyophilized oxidized cardiolipin-BSA or -KLH complex in either 10 mM sodium acetate buffer (for useful pH values between 4.0-5.6) or 10 mM phosphate buffer (for useful pH values between 7.0-9.0). Adjust the solution to the useful pH, with 2 M acetic acid for pH values between 4.0-5.6 or with 1 M mono- or di-sodium phosphate for pH values between 7.0-9.0. Ethanol (0.5%) may optionally be added to the oxidized cardiolipin solution to improve reagent application by lowering the viscosity of the solution. Then, apply the oxidized cardiolipin-BSA or -KLH solution to nitrocellulose using a Matrix 1600 reagent dispensing module (Kinematic Automation, Twain Harte, Calif.) in accordance with the manufacturer's directions.

After application of the oxidized cardiolipin-BSA or -KLH preparation to nitrocellulose, the membrane should be dried for 30 minutes at 37° C. followed by 2 hours in a vacuum dessicator prior to use, for example, in a lateral flow device.

EXAMPLE 7

Detection of Anti-Lipoidal Antibodies in Human Serum with an Oxidized Cardiolipin-Protein Conjugate Capture Reagent This example demonstrates that anti-lipoidal antibodies in syphilitic serum may be detected using oxidized cardiolipin-protein conjugate capture reagent, which is immobilized in a nitrocellulose membrane, in concert with a mobile oxidized cardiolipin-protein-gold conjugate detector reagent.

One (1) µl of preparations 1-17 (as described in Table 2) were each applied to separate nitrocellulose membranes as described in Example 6, and set aside. A colloidal gold conjugate was prepared as described in Example 5 using oxidized cardiolipin preparation 6 (see Table 2).

Syphilitic serum (Lot 00) or non-reactive (normal, human) serum was diluted 1:10 and placed in an appropriate number of separate wells of a 40-well microtitre plate. Three (3) µl of gold-conjugated preparation 6 (for use as a detector reagent) was then added to each well. Nitrocellulose strips containing each of the immobilized preparations 1 through 17 (see Table 2) were then placed into wells containing the antibody and detector reagent solutions. The solution in the wells flowed up the strip by capillary action. Each immobilized oxidized cardiolipin preparation was tested against both syphilitic and non-reactive (i.e., control) serum.

As shown in Table 4, many of the oxidized cardiolipin preparations immobilized in or on nitrocellulose showed a positive reaction, which is indicative of a "sandwich" complex between the immobilized oxidized cardiolipin capture reagent, at least one anti-lipoidal antibody, and the oxidized cardiolipin gold conjugate detector reagent. Reactivity was measured on a scale of 0 (Neg) to 4+ with 4+ indicating the strongest signal observed on the nitrocellulose strip.

TABLE 4

| Cardiolipin Preparation | Reactive Serum Lot 00 | Non-Reactive Serum |
|---|---|---|
| 1 | 2+ | Neg |
| 2 | +/− | +/− |
| 3 | 1+ | Neg |
| 4 | 1+ | Neg |
| 5 | 4+ | Neg |
| 6 | 2+ | Neg |
| 7 | 1+ | +/− |
| 8 | 1+ | Neg |
| 9 | +/− | +/− |
| 10 | +/− | +/− |
| 11 | 2+ | Neg |
| 12 | 1+ | Neg |

EXAMPLE 8

Oxidation of Mixtures of Cardiolipin and Lecithin

This example describes the oxidation of mixtures of cardiolipin and lecithin, and demonstrates that oxidized mixtures of cardiolipin and lecithin perform at least as well as oxidized cardiolipin alone in the assays described in Examples 4-7.

Figure 8:
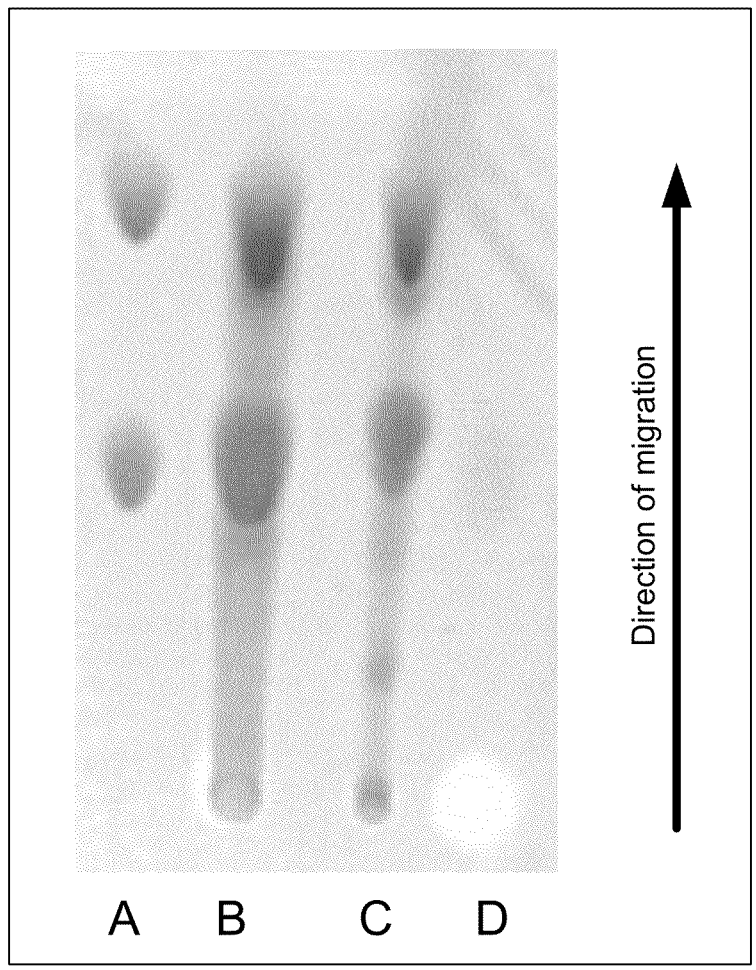
FIG. 8 shows a digital image of a thin-layer chromatograph of an oxidized cardiolipin-lecithin mixture. (A) A mixture of unmodified cardiolipin and unmodified lecithin in t-butanol; (B) an oxidized cardiolipin/lecithin mixture; (C) the upper, t-butanol phase following the oxidation of a cardiolipin/lecithin mixture; and (D) the lower, aqueous phase following the oxidation of a cardiolipin/lecithin mixture. The direction of migration of each sample is shown by an arrow.

Cardiolipin and lecithin were mixed together in ratios of 1:1, 1:3, and 1:5 cardiolipin to lecithin by weight. The mixtures were then oxidized as described in Example 1. As shown in FIG. 8, lane A, a mixture of unmodified cardiolipin and unmodified lecithin resolves into two spots on a TLC strip. Unmodified cardiolipin migrates to the top of the TLC strip, as indicated by the dark spot furthest from the point of origin (see also, FIG. 2, lane A). Unmodified lecithin migrates somewhat more slowly on the TLC place and is shown as the dark spot approximately halfway between the cardiolipin and the point of origin.

As described previously, oxidation under the conditions of Example 1 oxidizes alkenes, cleaves the fatty acid side chains, and introduces carboxyl groups into one or more of the fatty acid side chains of cardiolipin and lecithin. Carboxyl groups present in oxidized molecules interact more strongly with the silica substrate of a TLC strip, which retards the migration of the oxidized forms along the strip. Hence, in oxidized mixtures of cardiolipin and lecithin, a pronounced smear in the direction of migration is observed (see FIG. 8, lanes B and C). In addition, oxidative cleavage of the fatty acid side chains produces alkyl carboxylates, which have little mobility on a TLC strip under these conditions. As especially evident in FIG. 8, lane D, the carboxylates are thought to be represented by a white spot (due to dye exclusion), which is coextensive with the point of origin. Following oxidation of cardiolipin/lecithin mixtures as described in this example, oxidized forms of cardiolipin were found predominantly in the t-butanol phase (shown in FIG. 8, lane C), while alkyl carboxylates were found predominantly in the aqueous phase (see FIG. 8, lane D).

A. BSA and KLH Conjugation of Oxidized Cardiolipin/Lecithin Mixtures

Oxidized mixtures of cardiolipin and lecithin were conjugated to either BSA or KLH, as described in Method 3 of Example 2. The BSA- or KLH-conjugated cardiolipin/lecithin preparations are described in Table 5.

TABLE 5

Cardiolipin/Lecithin Mixtures

| Cardiolipin (CL) Lecithin (L) Prep. No. | CL:L Ratio (by weight) | Attachment Molecule | Amount of Attachment Molecule Per Reaction (mg) |
|---|---|---|---|
| C/L 1 | 1:1 | BSA | 5 |
| C/L 2 | 1:1 | BSA | 2 |
| C/L 3 | 1:1 | KLH | 2 |
| C/L 4 | 1:1 | KLH | 1 |
| C/L 5 | 1:3 | BSA | 5 |
| C/L 6 | 1:3 | BSA | 2 |
| C/L 7 | 1:3 | KLH | 2 |
| C/L 8 | 1:3 | KLH | 1 |
| C/L 9 | 1:5 | BSA | 5 |
| C/L 10 | 1:5 | BSA | 2 |
| C/L 11 | 1:5 | KLH | 2 |
| C/L 12 | 1:5 | KLH | 1 |

B. RPR Inhibition Test of Oxidized Cardiolipin/Lecithin Mixtures

The antigenicities of the cardiolipin/lecithin preparations described in Table 5 were tested in the RPR Inhibition Test, as described in Example 3. As shown in Table 6, each of the cardiolipin/lecithin preparations completely inhibited the reactivity of syphilitic serum in the traditional RPR test.

TABLE 6

RPR Inhibition Test Results for Cardiolipin/Lecithin Mixtures

| Cardiolipin/Lecithin Prep. Used for Serum Preincubation | Serum (Lot 50L) Dilution | | | | | |
|---|---|---|---|---|---|---|
| | 1:1 | 1:2 | 1:4 | 1:8 | 1:16 | 1:32 |
| None (i.e., Control) | R | R | $R_{(-)}$ | Rm | N | N |
| C/L 1 | N | N | N | N | N | N |
| C/L 2 | N | N | N | N | N | N |
| C/L 3 | N | N | N | N | N | N |
| C/L 4 | N | N | N | N | N | N |
| C/L 5 | N | N | N | N | N | N |
| C/L 6 | N | N | N | N | N | N |
| C/L 7 | N | N | N | N | N | N |
| C/L 8 | N | N | N | N | N | N |
| C/L 9 | N | N | N | N | N | N |
| C/L 10 | N | N | N | N | N | N |
| C/L 11 | N | N | N | N | N | N |
| C/L 12 | N | N | N | N | N | N |

R = strong positive reaction
$R_{(-)}$ = positive reaction
Rm = weak reaction
$Rm_{(-)}$ = very weak reaction
N = negative reaction This result demonstrates that the oxidized cardiolipin/lecithin mixtures very efficiently strip (i.e., remove) anti-lipoidal antibodies from the syphilitic serum, so that such serum is non-reactive in the traditional RPR test.

C. Immunodot Testing of Oxidized Cardiolipin/Lecithin Mixtures

Figure 10:
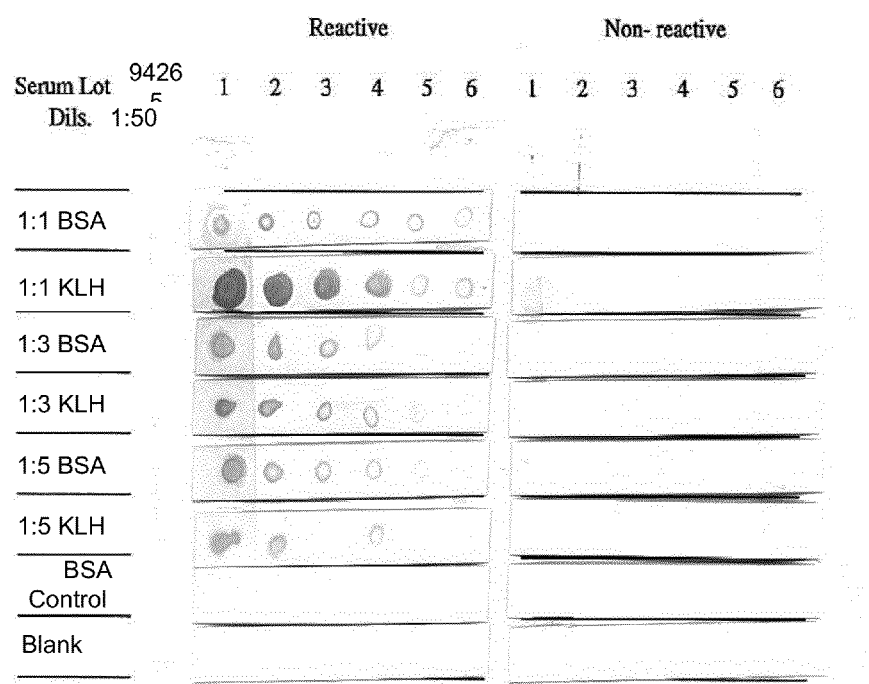
FIG. 10 shows a digital image of a dot blot assay used to determine the antigenicity of six oxidized cardiolipin/lecithin-BSA or -KLH conjugates. The amounts of the respective antigens applied to each dot in the assay are given in the table below the blot.

Dot blot assays were performed using the Immun-Blot® Assay Kit (BioRad) with a goat anti-human IgG alkaline-phosphatase conjugate in accordance with the manufacturer's instructions. As shown in FIG. 10, oxidized cardiolipin/lecithin mixtures in the range 375 ng to 21 µg per dot reacted with syphilitic serum (Lot 94265; 1:50 dilution). In comparison, none of the tested amounts of the oxidized cardiolipin/lecithin preparations showed any significant reaction with normal, human serum (i.e., non-syphilitic serum).

The preparations where cardiolipin and lecithin were oxidized in a 1:1 ratio (by weight) and then conjugated to either BSA or KLH (i.e., 1:1 BSA and 1:1 KLH) were most reactive with syphilitic serum. As little as 375 ng of the 1:1 BSA preparation and 656 ng of the 1:1 KLH preparation bound to human antibodies present in the syphilitic serum in this assay.

EXAMPLE 9

Detection of Anti-Lipoidal Antibodies in Human Serum with Protein-A or Anti-Human Antibody Capture Reagent This example demonstrates that anti-lipoidal antibodies present in human serum may be detected using protein-A or anti-human antibody capture reagent, which is immobilized in a nitrocellulose membrane, in concert with a mobile oxidized cardiolipin-protein-gold conjugate detector reagent.

Whole blood will be collected from a human subject thought to be at risk for a condition that gives rise to serum levels of anti-lipoidal antibodies. Such conditions include, for example, *T. pallidum* infection (i.e., syphilis) or lupus. Serum will be separated from the whole blood by methods well known in the art. The serum may be diluted, for example, with normal saline or other solutions that will not denature or otherwise affect the specific binding of anti-lipoidal antibodies present in the serum or otherwise interfere with the described method.

The serum sample will be applied to a nitrocellulose strip containing a mobile or mobilizable, labeled oxidized cardiolipin-protein conjugate detector reagent. Such conjugate may be, for example, gold-labeled oxidized cardiolipin-BSA, or gold-labeled oxidized cardiolipin-KLH conjugate, or a gold-labeled, BSA-conjugated mixture of oxidized cardiolipin and oxidized lecithin, or a gold-labeled, KLH-conjugated mixture of oxidized cardiolipin and oxidized lecithin.

Anti-lipoidal antibodies present in the serum sample will bind to the cardiolipin of the detector reagent and flow (such as by capillary action, or by lateral flow forces) to a portion of the nitrocellulose strip where a protein-A or anti-human antibody capture reagent is immobilized. The anti-lipoidal antibody complexed with the cardiolipin detector reagent will be captured by the protein A or anti-human antibody capture reagent. Accumulation of detector reagent complexes in this manner will result in a detectable signal (for example, a visible signal) on the nitrocellulose in the area where the capture reagent is immobilized.

The appearance of a detectable signal as described will indicate that anti-lipoidal antibodies are present in the serum sample, and may be useful in the diagnosis of certain conditions, such as syphilis or lupus.

EXAMPLE 10

Detection of Anti-Lipoidal Antibodies in Human Serum with Enzyme-Linked Immunoassay This example demonstrates that anti-lipoidal antibodies present in human serum may be detected by using oxidized cardiolipin conjugated to BSA or KLH as a capture reagent, which is immobilized in a microtiter plate for the performance of an enzyme-linked immunoassay. Alternatives to BSA and KLH include synthetic protein MAPS, IgY, streptavidin, and avidin. The wells of a 96-well microtiter plate were coated with 100 µl (10 µg/ml) of a solution containing 10 µg/ml oxidized cardiolipin-BSA or oxidized cardiolipin-KLH complex. The solution was allowed to dry overnight at 37° C. The wells were then blocked for 2 hours at room temperature with at least 200 µl 1% casein in Tris phosphate buffered saline (TPBS) pH 7.2. The wells were washed once with 200 µl of TPBS. Then, 100 µl of human serum (either control or from *T. pallidum*-infected individual) diluted 1:20, 1:40, 1:80 or 1:160 in 1% casein TPBS was added to each well. The microtiter plate was incubated at room temperature for 60 minutes; followed by three washes with 200 µl TBST. One hundred (100) µl of goat anti-human antibody conjugated to horseradish peroxidase (HRP) diluted 1:3000 in 1% casein TPBS was added to each well at room temperature for 45 minutes. The microtiter plate was washed three times with TPBS prior to the addition of 100 µl per well of TMB substrate. In the presence of HRP, the TMB substrate changes color. The HRP enzyme-substrate reaction was stopped by the addition of 2M sulfuric acid. The solution in each well was read spectrophotometrically at 450 nm.

As shown in Tables 7 and 8, anti-lipoidal antibodies present in human syphilitic sera ("Reactive") bound to oxidized cardiolipin-BSA or -KLH complexes immobilized in the wells of the microtiter plate. However, there was no significant binding of control ("Nonreactive") serum to the same immobilized antigen.

TABLE 7

Enzyme-Linked Immunoassay with Oxidized Cardiolipin-BSA Antigen

| Serum dilution | Reactive | Reactive | Nonreactive | Nonreactive |
|---|---|---|---|---|
| 1:20 | 1.938 | 1.712 | 0.103 | 0.066 |
| 1:40 | 0.569 | 0.769 | 0.004 | 0.005 |
| 1:80 | 0.348 | 0.495 | 0.018 | 0.020 |
| No sera | 0.032 | 0.031 | 0.029 | 0.033 |

Duplicate tests (results shown) were performed for each data point. The syphilitic serum used for this data set has a titer of 1:64 as determined by the RPR test.

TABLE 8

Enzyme-Linked Immunoassay with Oxidized Cardiolipin-BSA Antigen

| Serum dilution | Reactive | Reactive | Nonreactive | Nonreactive |
|---|---|---|---|---|
| 1:20 | 1.970 | 1.700 | 0.071 | 0.062 |
| 1:40 | 0.825 | 0.842 | 0.045 | 0.039 |
| 1:80 | 0.552 | 0.479 | 0.031 | 0.027 |
| 1:160 | 0.281 | 0.245 | 0.022 | 0.022 |
| No sera | 0.046 | 0.034 | 0.021 | 0.019 |

Duplicate tests (results shown) were performed for each data point. The syphilitic serum used for this data set has a titer of 1:128 as determined by the RPR test.

EXAMPLE 11

Covalent Attachment of Oxidized Cardiolipin to ELISA Plates

This example describes methods used to attach oxidized cardiolipin to ELISA plates, which were amine coated or not.

Oxidized cardiolipin was prepared as described in Example 1.

Coating of Functionalized Amine Plates with Oxidized Cardiolipin:

Nunc Amine Plates (Nunc Immobilizer Amino 12×8 Stripes, Thermo Fisher Scientific, Cat#436013) were incubated with oxidized cardiolipin. The oxidized cardiolipin was lyophilized powder, which was dissolved completely in 10 mM phosphate buffer, pH 5.6. The oxidized cardiolipin solution was sonicated for 5 minutes in a sonicator bath. EDC (Sigma, Cat#E6383-5G) and Sulfo-NHS (Thermoscientific, Cat#24510) in amounts identical to the oxidized cardiolipin (e.g., 10 mg each of EDC, Sulfo-NHS and oxidized cardiolipin) were each dissolved in sterile distilled water (Cell gro, Meditech, Inc, Cat#25-055-CM). Both the EDC and Sulfo-NHS solutions were added to the oxidized cardiolipin solution. The resulting solution was sonicated for 5 minutes in sonicator bath, and then mixed using a magnetic stirrer for 15 minutes. The plates were coated with concentrations of either 0.15 to 0.625 mg/m and 100 µl/was applied to each well of the Nunc amine plate, and incubated overnight at 37° C. The solution was removed from the wells, and the wells washed twice with PBST (1×PBS+0.05% Tween-20 (10% Tween-20 solution, Biorad, Cat#161-0781). 300 µl/well of blocker casein solution with 0.05% Tween-20 (Thermo scientific, Cat#37532) was added to each well and incubated at 37° C. for 2 hours. The plate was then washed twice with PBST and allowed to completely dry (e.g., overnight at room temperature).

Coating of Multi-well Plates with Oxidized Cardiolipin using Proteins.

Several methods were used to conjugate oxidized cardiolipin with BSA, IgY or KLH using EDC and NHS. 100 µl of a 40 µg/ml solution of BSA, IgY or KLH in 50 mM carbonate buffer, pH 9.5 was applied to the wells of Thermo Scientific™ Nunc™-96 well Microplate, Maxisorp ELISA plates. A lyophilized powder of oxidized cardiolipin was dissolved in 1 ml of 10 mM Phosphate Buffer, pH 5.6, resulting in a 10 mg/ml concentration. The oxidized cardiolipin solution was sonicated for 10 min in sonicator bath. 0.2 mL of sterile deionized water was added to 10 mg EDC. 0.2 mL of sterile deionized water was added to 10 mg msulfo NHS powder. Both the EDC and NHS solutions were added to the oxidized cardiolipin solution, and the resulting mixture sonicated for 10 min in sonicator bath. The solution was subsequently mixed for 15 minutes on a magnetic stirrer. The stock solution of cardiolipin was diluted to a coating concentration ranging from 0.125 to 0.620 mg/mL 100 µl/well of coating solution was added to a BSA-, IgY- or KLH-coated Maxisorp plate, and incubated at 37° C. for 2 hours. The plate was washed with PBST and blocked with 1% CTBST solution (Blocker Casein Solution with 0.05% Tween-20) for 2 hours at 37° C. The plate was washed twice with PBST before use.

EXAMPLE 12

Examination of Well-to-Well Variation

This example describes experiments used to demonstrate the minimal amount of well-to-well variation observed with a 96-well ELISA plate.

Plates made by coating functionalized amine plates with oxidized cardiolipin or using proteins (see Example 11) were tested against a panel of syphilis sera characterized by Rapid Plasma Reagin (RPR) titer. A 1:20 dilution of each sample was made by adding 200 µl of 1% CTBS+10 µl sample on a microtiter plate. 100 µl of the diluted serum was placed into the corresponding well of another microtiter plate and incubated at 37° C. for 30 minutes. Plates were washed five times with PBST. 100 µl of conjugate was added to the corresponding wells and incubated for one hour at 37° C. The conjugate is an equal mixture of 1;10,000 dilution of Goat-Anti human IgG (Fab'2)-Horseradish Peroxidase (Thermo Scientific, Cat #31414) and Goat-Anti human IgM (Fc 5µ)-Horseradish Peroxidase (Thermo Scientific, Cat#31415) in 1% casein, TBST. Plates were washed five times with PBST. 100 µl of TMB was added to each well and incubated for 10 minutes at room temperature. 100 µl of 2 N sulfuric acid solution was added to stop the reaction. The plates were read at 450 and 620 nm in an ELISA reader.

As shown in Table 9, there is minimal well-to-well variability. A standard deviation of less than 0.099 and a coefficient of variation (CV) less than 10 are acceptable.

TABLE 9

Results demonstrating minimal well-to-well variability.

| RPR Titer | Number of Repeats at Absorbance 450 nm | | | | | | | | | | AVEG | STDEV | CV % |
|---|---|---|---|---|---|---|---|---|---|---|---|---|---|
| | 1 | 2 | 3 | 4 | 5 | 6 | 7 | 8 | 9 | 10 | | | |
| R1 | 0.265 | 0.294 | 0.274 | 0.299 | 0.335 | 0.327 | 0.3 | 0.299 | 0.297 | 0.299 | 0.299 | 0.021 | 6.96 |
| R2 | 0.283 | 0.328 | 0.311 | 0.32 | 0.329 | 0.333 | 0.31 | 0.308 | 0.324 | 0.318 | 0.316 | 0.015 | 4.59 |
| R4 | 0.53 | 0.52 | 0.495 | 0.574 | 0.583 | 0.487 | 0.575 | 0.546 | 0.577 | 0.504 | 0.539 | 0.037 | 6.85 |
| R8 | 0.719 | 0.745 | 0.737 | 0.739 | 0.752 | 0.67 | 0.811 | 0.712 | 0.74 | 0.733 | 0.736 | 0.035 | 4.80 |
| R16 | 0.812 | 0.836 | 0.76 | 0.882 | 0.857 | 0.867 | 0.865 | 0.85 | 0.904 | 0.856 | 0.849 | 0.040 | 4.69 |
| R32 | 1.149 | 1.186 | 1.145 | 1.03 | 1.177 | 1.118 | 1.144 | 1.08 | 1.181 | 1.155 | 1.137 | 0.049 | 4.31 |
| R64 | 1.324 | 1.441 | 1.426 | 1.311 | 1.363 | 1.272 | 1.437 | 1.36 | 1.497 | 1.411 | 1.384 | 0.070 | 5.04 |
| R128 | 2.246 | 2.251 | 2.071 | 2.38 | 2.141 | 2.04 | 2.231 | 2.184 | 2.182 | 2.17 | 2.190 | 0.097 | 4.42 |

EXAMPLE 13

Sensitivity and Specificity of the Non-Treponemal Assay

This example describes experiments used to demonstrate the sensitivity and specificity of the assay.

Plates made by coating functionalized amine plates with oxidized cardiolipin or using proteins (see Example 11) were tested against a panel of syphilis sera characterized by RPR titer. 545 RPR reactive samples and 461 non-RPR reactive samples were analyzed. A 1:20 dilution of each sample was made by adding 200 µl of 1% CTBS+10 µl sample in a microtiter plate. 100 µl of the diluted serum was placed into the corresponding well of another microtiter plate and incubated at 37° C. for 30 minutes and incubated for one hour at 37° C. The plates were washed five times with PBST. 100 µl of conjugate was added to the corresponding wells. The conjugate is an equal mixture of 1;10,000 dilution of Goat-Anti human IgG (Fab'2)-Horseradish Peroxidase (Thermo Scientific, Cat #31414) and Goat-Anti human IgM (Fc 5µ)-Horseradish Peroxidase (Thermo Scientific, Cat#31415) in 1% casein, TBST. Plates were washed five times with PBST. 100 µl of TMB was added to each well and incubated for 10 minutes at room temperature. 100 µl of 2 N sulfuric acid solution was added to stop the reaction. The plates were read at 450 and 620 nm in an ELISA reader.

A cut-off value of OD 0.250 was used. That is, an OD value above 0.250 is considered as a positive reaction and an OD value below 0.250 is a negative reaction. As shown in Table 10, the 545 RPR reactive samples were grouped based on the previously determined RPR titer (from a low of R1 to a high of R1024). For each group (RTR titer), the number of samples that were positive with the disclosed non-treponemal EIA assay was determined (EIA+), and shown as a % of the total for each goru (%). The mean OD for each group is also shown. The cumulative sensitivity is also shown for all 454 samples. Thus, Table 10 shows that there is a correlation between the RPR titer and the OD calculated using the disclosed assay. The sensitivity ranged from a low of about 93% for low titers, and 100% for higher titers.

TABLE 10

Sensitivity of non-treponemal EIA in reference to RPR titer.

| RPR titer | Number analyzed | EIA+ | % | Mean OD | Cumulative Sensitivty % |
|---|---|---|---|---|---|
| R1 | 150 | 96 | 64 | 0.410 | 93.3 |
| R2 | 95 | 72 | 75.8 | 0.466 | 96.2 |
| R4 | 59 | 54 | 91.5 | 0.594 | 98.5 |
| R8 | 57 | 54 | 94.7 | 0.752 | 99.3 |
| R16 | 40 | 40 | 100 | 1.172 | 100 |
| R32 | 58 | 58 | 100 | 1.773 | 100 |
| R64 | 41 | 41 | 100 | 2.104 | 100 |
| R128 | 27 | 27 | 100 | 2.340 | 100 |
| R256 | 11 | 11 | 100 | 2.689 | 100 |
| R512 | 5 | 5 | 100 | 2.800 | 100 |
| R1024 | 2 | 2 | 100 | 3.059 | 100 |

A cut-off value of OD 0.250 was used. That is, an OD value above 0.250 is considered as a positive reaction and an OD value below 0.250 is a negative reaction. As shown in Table 11, all 126 RPR nonreactive/TPPA negative samples were positive with the disclosed non-treponemal EIA assay (biologically false positive samples). Thus, the disclosed assay is more sensitive at detecting biologically false positive samples than the RPR assay. In addition, the disclosed assay can have a specificity of 100%, as the 194 RPR nonreactive/TPPA negative samples were also negative with the disclosed non-treponemal EIA assay (negative samples). In addition, Table 12 shows that the disclosed non-treponemal EIA assay can detect positive samples that were missed by the RPR assay (of the 141 samples negative for RPR/TPPA positive, 62 were positive using the disclosed assay). Thus, the disclosed assay can detect syphilis (non-treponemal) positive samples that the RPR assay cannot.

TABLE 11

Specificity of nontreponemal EIA in reference to RPR

| Sample Category | RPR Neg | TPPA EIA | % | Mean OD | Specificity |
|---|---|---|---|---|---|
| Negative samples (RPR Neg., TPPA Neg. EIA neg.) | 194 | 194 | 100 | 0.136 | 100% |
| Biologically False Positive samples (RPR Neg, TPPA Neg., & EIA Positive) | 126 | 126 | x | 0.387 | x |
| RPR Neg, TPPA Pos. and EIA Pos. | 141 | 62 | 43.97 | 0.370 | x |

Figure 13:
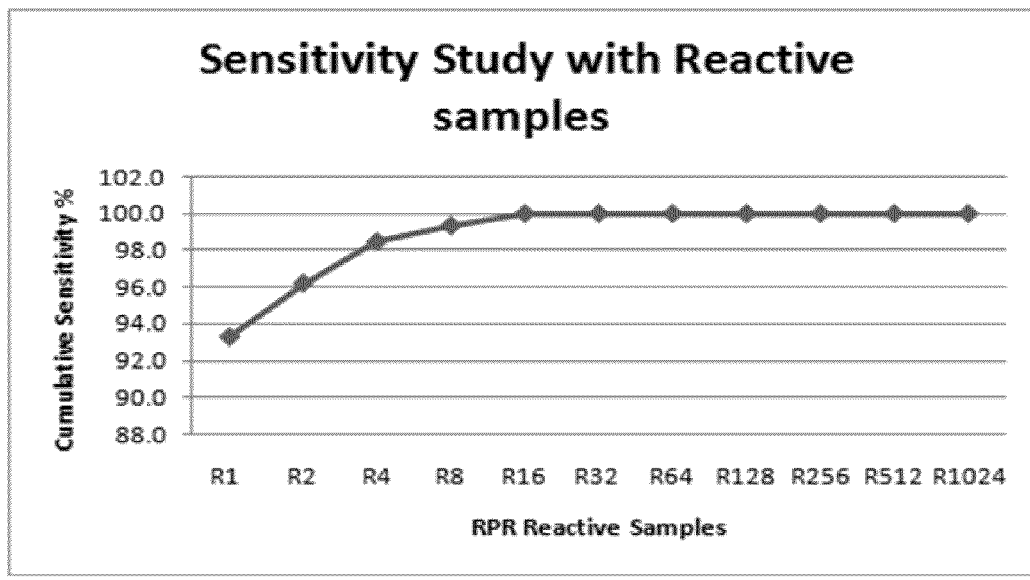
FIG. 13 is a graph showing the cumulative sensitivity of the disclosed assay.
Figure 14:
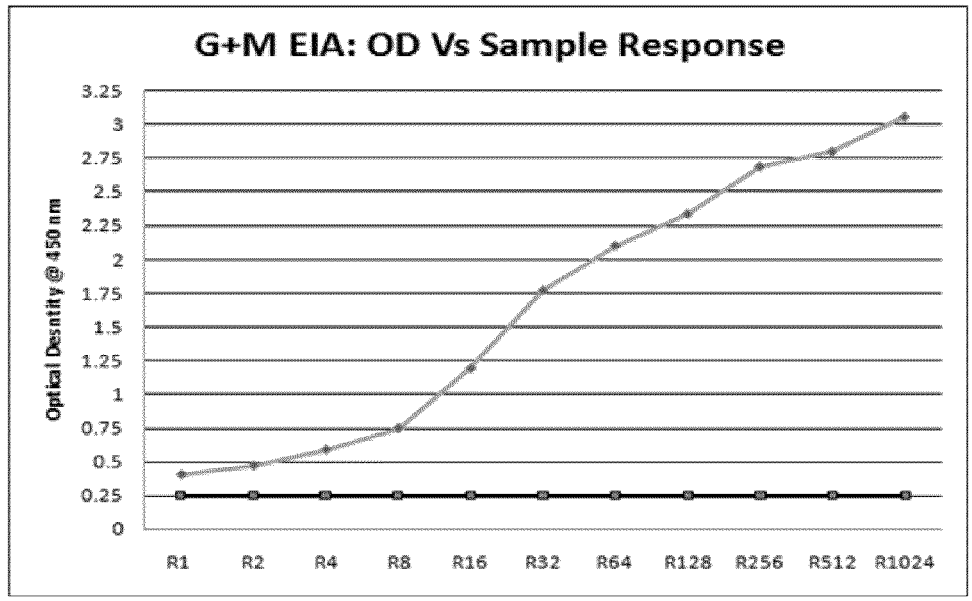
FIG. 14 is a graph showing the correlation between the cardiolipin RPR titer and the optical density of the disclosed nontreponemal screening EIA assay. The lower the antibody titer RPR reactive 1:1 (R1) the closer to the x axis. The greater the RPR titer 1:1024 (R1024) the greater the OD value.

The proof of concept of the technology was evaluated by testing 1006 stored serum samples using RPR as the comparator assay. The specificity was determined to be 100% and the sensitivity varied from 93.3% to 100% according to the RPR antibody titer (Tables 10 and 11). A summary is shown in FIG. 13. FIG. 14 shows the correlation between the cardiolipin RPR titer and the optical density of the new nontreponemal screening EIA assay. The lower the antibody titer RPR reactive 1:1 (R1) the closer to the x axis. The greater the RPR titer 1:1024 (R1024) the greater the OD value.

Table 12 shows the results of the nontreponemal EIA assay (Results) as compared to the RPR assay (RPR) and the treponemal assay (TP-PA) using serum samples with various stages of syphilis. OD value greater that 0.250 is considered reactive. R means reactive. The results shows that all of the samples were reactive using the disclosed assay.

TABLE 12

Serum panel characterized by stages of syphilis (cut-off 0.250)

| Sample ID | RPR | TP-PA | EIA OD | OD/CO | Results |
|---|---|---|---|---|---|
| Primary Untreated | | | | | |
| 2072 | R16 | R | 0.976 | 3.90 | R |
| 2070 | R16 | R | 0.980 | 3.92 | R |
| 2082 | R16 | R | 0.506 | 2.02 | R |
| 2083 | R16 | R | 0.933 | 3.73 | R |
| 2183 | R16 | R | 0.620 | 2.48 | R |
| 2899 | R8 | R | 0.338 | 1.35 | R |
| 2890 | R2 | R | 0.359 | 1.44 | R |
| Primary Treated | | | | | |
| 4-005-81 | R8 | R | 0.282 | 1.13 | R |
| 4-006-81 | R512 | R | 2.987 | 11.95 | R |
| 4-007-84 | R64 | R | 1.471 | 5.88 | R |
| 4-012-81 | R8 | R | 0.397 | 1.59 | R |
| 4-013-82 | R128 | R | 0.492 | 1.97 | R |
| Secondary Untreated | | | | | |
| 2066 | R32 | R | 0.351 | 1.40 | R |
| 2079 | R32 | R | 0.467 | 1.87 | R |
| 2897 | R38 | R | 0.678 | 2.71 | R |
| Secondary Treated | | | | | |
| 6-006-81 | R16 | R | 0.652 | 2.61 | R |
| 6-007-81 | R16 | R | 0.507 | 2.03 | R |
| 6-013-85 | R4 | R | 0.366 | 1.46 | R |
| 6-015-81 | R16 | R | 0.634 | 2.54 | R |
| 6-024-69 | R32 | R | 0.741 | 2.96 | R |
| Latent Untreated | | | | | |
| 15-8-5C | R16 | R | 0.282 | 1.13 | R |
| 15-8-5 | R16 | R | 0.393 | 1.57 | R |
| 15-8-4C | R32 | R | 0.315 | 1.26 | R |
| 15-8-4B | R32 | R | 0.302 | 1.21 | R |
| 15-8-4A | R32 | R | 0.314 | 1.26 | R |
| 15-8-3A | R128 | R | 0.270 | 1.08 | R |
| 15-8-2C | R2 | R | 0.261 | 1.04 | R |
| 15-8-2 | R128 | R | 2.088 | 8.35 | R |
| 15-8-1 | R512 | R | 1.505 | 6.02 | R |
| 8-014-82 | R2 | R | 0.289 | 1.16 | R |
| 8-013-82 | R256 | R | 0.924 | 3.70 | R |
| 15-8-8A | R64 | R | 0.597 | 2.39 | R |
| 15-8-8 | R64 | R | 0.856 | 3.42 | R |
| Latent Treated | | | | | |
| 15-8-8B | R16 | R | 0.435 | 1.74 | R |
| 15-8-14 | R32 | R | 0.413 | 1.65 | R |

EXAMPLE 14

Double Antigen System: Two Step Conjugate System

This example describes methods and results using a double antigen (cardiolipin) assay.

In this example, oxidized cardiolipin is attached to a plate as described in Example 11 (150 µg/µl of cardiolipin per well). The serum sample is then added to the plate, and cardiolipin antibodies in the sample are allowed to bind to the oxidized cardiolipin attached to the plate. Subsequently, cardiolipin-biotin-streptavidin-HRP is added, which will bind to the bound cardiolipin antibodies, if present. The HRP is then detected, wherein the presence of detectable HRP indicates the presence of cardiolipin antibodies in the sample, while the absence of detectable HRP above a cut-off value indicates the absence of cardiolipin antibodies in the sample.

Preparation of Cardiolipin-Biotin-Streptavidin-HRP20 Conjugate:

A cardiolipin-biotin conjugate was made as described on Example 3. Briefly, a conjugate was prepared by adding 620.5

μg of cardiolipin-biotin to 0.2 mg of streptavidin-poly-HRP20 conjugate (Fitzgerald, Acton, Mass., Cat#65R-S103PHRP) and mixed at room temperature for two hours. The solution was dialyzed again in an Amicon® Ultracel™ ultrafiltration disk with a 10 kDa membrane (Millpore catalog #PLGC04310 or PLGC06210), with a minimum of two buffer changes. The conjugate was collected from the membrane and concentrated to 0.25 mL by using Centricon (MWCO 10 KDa). To the concentrated conjugate, and equal volume of glycerol (total 50%) was added. The resulting conjugated was stored at −20° C.

Analysis of Sample:

Samples were diluted 1:2 to 1:64 in sample diluent (see Example 12) and 100 μl added to each well of a multi-well plate coated with oxidized cardiolipin (see Example 11). The samples were incubated for 30 minutes at 37° C. The contents of the wells were discarded, and the plate washed five times with 350 μl of wash solution (PBST). 100 μl of cardiolipin-biotin-streptavidin-HRP20 was placed into each well and incubated for 30 minutes at 37° C. The contents of the wells were discarded, and the plate washed five times with 350 μl of wash solution. 100 μl of TMB substrate solution was placed into each well incubated for 15 minutes at room temperature in dark. 100 μl of stop solution was added to each well and incubated for 5 minutes at room temperature. Optical density at 450 nm was determined and the results calculated.

As shown in Table 13, the double antigen system can be used to detect non-treponemal antigens. Table 13 shows the analysis of a sample analyzed three times.

TABLE 13

Results of Double-Antigen System

| | Abs at 450 | | |
|---|---|---|---|
| Dilution | 3.118 | 3.11 | 3.216 |
| 1:2 | 1.486 | 1.357 | 1.504 |
| 1:4 | 0.443 | 0.441 | 0.479 |
| 1:8 | 0.217 | 0.19 | 0.231 |
| 1:16 | 0.119 | 0.124 | 0.17 |
| 1:32 | 0.102 | 0.086 | 0.112 |
| 1:64 | 0.079 | 0.08 | 0.108 |
| Neg. pool sample | 0.077 | 0.079 | 0.081 |

EXAMPLE 15

Single Tests for Nontreponemal IgG and IgM

This example describes methods that can be used to detect nontreponemal IgG or IgM in a sample. Such methods can be used to determine the nontreponemal antibody response at all stages of syphilis.

In some examples, an IgM EIA test can be used as a confirmatory test, used to diagnose a recent syphilis infection, used to monitor efficacy of syphilis treatment, for congenital syphilis, or combinations thereof. In some examples, an IgG EIA test can be used as a confirmatory test, used to determine the stages of syphilis infection, used to monitor efficacy of syphilis treatment, or combinations thereof.

Figure 15:
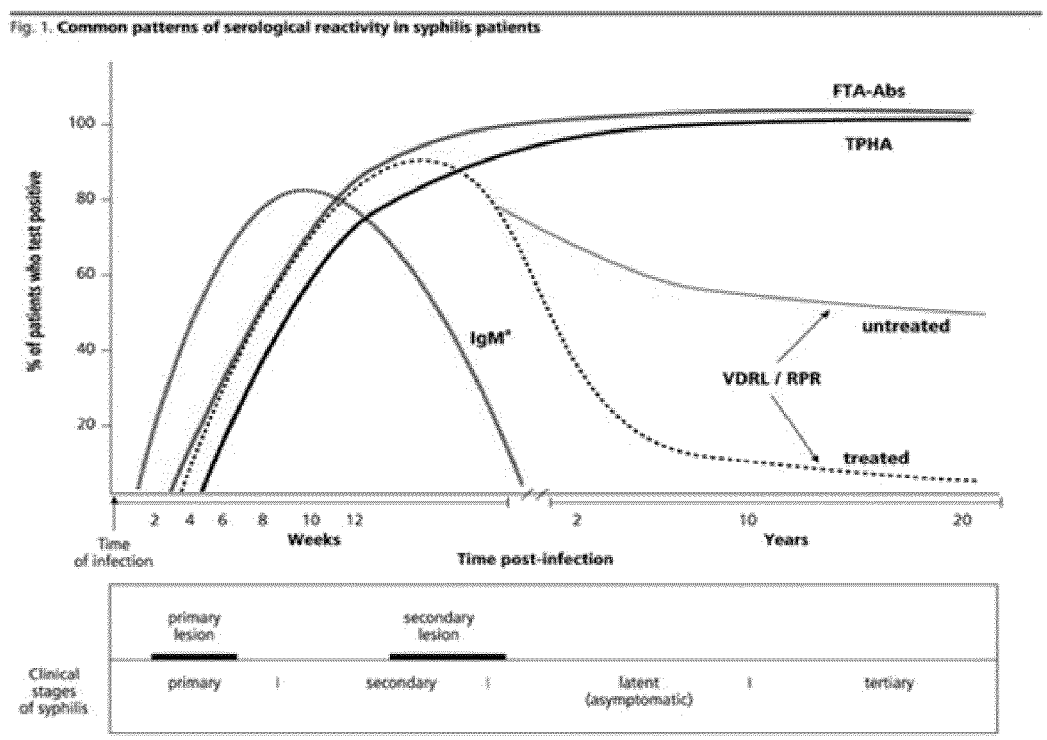
FIG. 15 shows the common patterns of serological reactivity in syphilis patents.

In some examples, the determined OD value of nontreponemal IgM and IgG can be used as a semi-quantitative comparison to RPR titer. For example, primary, secondary or latent, treated or untreated cases of syphilis can be differentiated on the basis of IgG and IgM antibody concentration. The appearance or reduction of the IgM and IgG antibody content after treatment or time can be monitored. In addition, the significance of IgG and IgM nontreponemal antibodies in the progression and management of syphilis can be determined FIG. 15 shows the common patterns of serological reactivity in syphilis patents.

Analysis of Sample:

The ELISA plates were prepared as in Example 11 using a 150 μg/mL of cardiolipin per well. Samples were diluted 1:10 in sample diluent (see Example 12) and 100 μl added to each well of a multi-well plate coated with oxidized cardiolipin. Samples were incubated for 30 minutes at 37° C. The contents of the wells were discarded, and the plate washed five times with 350 μl of wash solution (PBST). 100 μl of Goat Anti-human IgM-HRPO (Pierce#31415) for the IgM test at a 1:15,000 dilution and 100 μl for the Goat Anti-human IgG-HRPO (Pierce#31414 for) the IgG test at 1:10,000 dilution was placed into each corresponding well and incubated for 30 minutes at 37° C. The contents of the wells was discarded, and the plate washed five times with 350 μl of wash solution. 100 μl of TMB substrate solution was placed into each well incubated for 15 minutes at room temperature in dark. 100 μl of a 2N sulfuric acid stop solution was added to each well and incubated for 5 minutes at room temperature. Optical density at 450 nm was determined and the results calculated.

As shown in Table 14, 24 serum samples with known RPR tiers were separately tested with the disclosed nontreponemal EIA IgM and IgG assay. The results were then collated for each RPR titer group (from R1 to 8256) for easier visualization. The cut-off was OD 0.250.

TABLE 14

Nontreponemal EIA IgG and IgM OD value compared to RPR titer

| Sample ID | RPR titer | IgM EIA | IgG EIA |
|---|---|---|---|
| 4352 | R1 | 0.951 | 0.509 |
| 2073 | R1 | 0.388 | 0.338 |
| 2182 | R1 | 0.615 | 0.368 |
| 2072 | R1 | 1.462 | 1.442 |
| 3535 | R1 | 0.952 | 0.606 |
| 2082 | R1 | 0.59 | 0.53 |
| 2081 | R1 | 0.423 | 0.215 |
| 3536 | R1 | 0.647 | 0.368 |
| NT19 | R1 | 1.111 | 0.942 |
| 2067 | R2 | 0.926 | 0.643 |
| 9795 | R4 | 1.008 | 1.087 |
| 2079 | R4 | 1.024 | 0.128 |
| 2080 | R4 | 1.045 | 0.268 |
| 9794 | R8 | 0.908 | 1.126 |
| 8957 | R8 | 0.159 | 0.117 |
| 2183 | R8 | 1.216 | 0.696 |
| 9624 | R16 | 1.718 | 1.922 |
| 9396 | R16 | 1.502 | 2.067 |
| 8938 | R16 | 0.947 | 0.608 |
| 0015L | R16 | 2.42 | 0.647 |
| 8928 | R32 | 1.275 | 1.18 |
| R128 | R128 | 2.403 | 0.64 |
| HS004 | R128 | 2.064 | 2.1 |
| 8666 | R256 | 1.805 | 2.271 |

EXAMPLE 16

Nontreponemal IgG and IgM Calibrators

This example describes methods that can be used to generate IgM and IgG affinity purified calibrators. Such calibrators can be used to calculate the specific antibody content of a serum sample by linear regression and can replace the cardiolipin antibody titer as a measurement of antibody content.

Currently, RPR or VDRL titer determinations are the only available procedures to establish the serological level of nontreponemal antibody reactivity. There are many factors that affect the accuracy of RPR determinations, making the suitability of this test questionable for exact determinations. Under laboratory controlled conditions, RPR is subject to observer interpretation of results specially those with low titer. In developing countries and resource poor settings the variability of RPR results is greatly magnified to the point that data collected for diagnosis and epidemiological studies could be adversely affected. Thus, alternative assays are need.

The calibrators are prepared by affinity purification of non-treponemal IgG and IgM antibodies from syphilitic sera. The protein concentration of each calibrator is determined, then the OD of the calibrators are plotted against their concentrations to establish a calibration curve. By means of a linear regression the OD of the unknown samples are plotted against the standard curve and the concentration of the unknown is determined.

Nontreponemal IgM and IgG antibody content in a sample can be quantified using the calibrators. For example, such an assay can be used to measure the specific antibody content of IgG and IgM expressed in mg, μg or ng/ml to eliminate the need of determining a RPR antibody titer, to follow the progression of the disease and to monitor efficacy of treatment, or combinations thereof.

While this disclosure has been described with an emphasis upon particular embodiments, it will be obvious to those of ordinary skill in the art that variations of the particular embodiments may be used and it is intended that the disclosure may be practiced otherwise than as specifically described herein. Features, characteristics, compounds, chemical moieties, or examples described in conjunction with a particular aspect, embodiment, or example of the disclosure are to be understood to be applicable to any other aspect, embodiment, or example of the disclosure. Accordingly, this disclosure includes all modifications encompassed within the spirit and scope of the disclosure as defined by the following claims.

The invention claimed is:

1. A method for diagnosing syphilis, comprising:
   contacting a biological sample from a subject with a multi-well plate, wherein the multi-well plate comprises oxidized cardiolipin that is immunoreactive with anti-lipoidal antibodies, wherein the oxidized cardiolipin comprises a central glycerol moiety and fatty acid side chains and is generated by a method comprising:
   reacting the cardiolipin with a periodate salt and a permanganate salt to oxidize alkene groups of fatty acid side chains of the cardiolipin to provide terminal carboxyl groups on one or more of the side chains;
   adding a reducing agent to the cardiolipin suspension after reacting the cardiolipin with the periodate salt and the permanganate salt to quench oxidation of the cardiolipin and to reduce a β-ketone formed in the central glycerol moiety to a β-hydroxyl group so as to retain immunogenicity of the central glycerol moiety; and
   activating the carboxyl groups of the oxidized cardiolipin to covalently attach a protein carrier to at least one of the carboxyl groups or to permit attachment of the oxidized cardiolipin to an amine; and
   detecting formation of a complex among an anti-lipoidal IgG, IgA, or IgM antibody in the biological sample and the oxidized cardiolipin on the solid support,
   wherein detection of the complex diagnoses syphilis.

2. The method of claim 1, further comprising:
   contacting the solid support with a labeled anti-human antibody, or
   contacting the solid support with a labeled cardiolipin.

3. The method of claim 2, wherein the labeled anti-human antibody comprises:
   a labeled goat-anti human IgG;
   a labeled goat-anti human IgM;
   or both.

4. The method of claim 3, wherein contacting the multi-well plate with a labeled anti-human antibody comprises:
   contacting the multi-well plate with a mixture of labeled goat-anti human IgG and labeled goat-anti human IgM; or
   contacting a first multi-well plate with labeled goat-anti human IgG can a second multi-well plate with labeled goat-anti human IgM.

5. The method of claim 3, wherein the label is horseradish peroxidase (HRP) and the method further comprises:
   contacting the multi-well plate with tetramethyl benzidine (TMB);
   wherein detecting comprises detecting a signal spectrophotometrically at 450 nm.

6. The method of claim 1, further comprising:
   applying anti-human antibody conjugated to horseradish peroxidase (HRP) to the multi-well plate; and
   applying tetramethyl benzidine (TMB) to the multi-well plate;
   wherein detecting comprises detecting a signal spectrophotometrically at 450 nm.

7. The method of claim 1, further comprising:
   applying biotinylated cardiolipin to the multi-well plate; and
   applying HRP-streptavidin to the multi-well plate;
   wherein detecting comprises detecting a signal spectrophotometrically at 450 nm.

8. A method for diagnosing syphilis, comprising:
   contacting a biological sample from a subject with a multi-well plate, wherein the multi-well plate comprises (1) a treponemal antigen that reacts with antibodies to $T.\ pallidum$ and (2) oxidized cardiolipin that is immunoreactive with anti-lipoidal antibodies, wherein the oxidized cardiolipin comprises a central glycerol moiety and fatty acid side chains and is generated by a method comprising:
   reacting the cardiolipin with a periodate salt and a permanganate salt to oxidize alkene groups of fatty acid side chains of the cardiolipin to provide terminal carboxyl groups on one or more of the side chains;
   adding a reducing agent to the cardiolipin suspension after reacting the cardiolipin with the periodate salt and the permanganate salt to quench oxidation of the cardiolipin and to reduce a β-ketone formed in the central glycerol moiety to a β-hydroxyl group so as to retain immunogenicity of the central glycerol moiety; and
   activating the carboxyl groups of the oxidized cardiolipin to covalently attach a protein carrier to at least one of the carboxyl groups or to permit attachment of the oxidized cardiolipin to an amine;
   detecting formation of a complex among an anti-lipoidal antibody in the biological sample and the oxidized cardiolipin; and
   detecting formation of a complex among an anti-treponemal antibody in the biological sample and the treponemal antigen,
   wherein detection of the complexes diagnoses syphilis.

9. The method of claim 1, wherein the biological sample is a human serum sample.

10. The method of claim 1, wherein the anti-lipoidal antibody is detected quantitatively.

11. The method of claim 1, wherein the multi-well plate comprises an enzyme-linked immunosorbent assay (ELISA) multi-well plate.

12. The method of claim 8, wherein the multi-well plate comprises an enzyme-linked immunosorbent assay (ELISA) multi-well plate.

* * * * *

UNITED STATES PATENT AND TRADEMARK OFFICE
CERTIFICATE OF CORRECTION

PATENT NO.         : 8,778,619 B2
APPLICATION NO.    : 14/079634
DATED              : July 15, 2014
INVENTOR(S)        : Arnold R. Castro et al.

It is certified that error appears in the above-identified patent and that said Letters Patent is hereby corrected as shown below:

In the Claims:

Column 53, line 57, claim 1, "moeity" should be --moiety--.

Column 54, line 54, claim 8, "moeity" should be --moiety--.

Column 54, lines 7, 8, 13, 15-16 and 17, claims 3 and 4, "goat-anti human" should be --goat anti-human--.

Column 54, line 16, claim 4, "can" should be --and--.

Signed and Sealed this
Sixteenth Day of August, 2016

Michelle K. Lee
*Director of the United States Patent and Trademark Office*